US012110326B2

(12) United States Patent
Darce et al.

(10) Patent No.: US 12,110,326 B2
(45) Date of Patent: *Oct. 8, 2024

(54) ANTI-ILT3 ANTIBODIES AND ANTIBODY DRUG CONJUGATES

(71) Applicant: Bluefin BioMedicine, Inc., Beverly, MA (US)

(72) Inventors: Jaime Rene Darce, Arlington, MA (US); Scott Michael Lonning, Westford, MA (US); Nels Eric Pederson, Mansfield, MA (US); Klarisa Rikova, Reading, MA (US); Aleksandr Tkachev, Cambridge, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/585,815

(22) Filed: Jan. 27, 2022

(65) Prior Publication Data

US 2022/0227863 A1 Jul. 21, 2022

Related U.S. Application Data

(63) Continuation of application No. 16/484,238, filed as application No. PCT/US2018/017546 on Feb. 9, 2018, now Pat. No. 11,267,886.

(60) Provisional application No. 62/457,021, filed on Feb. 9, 2017.

(51) Int. Cl.
*C07K 16/28* (2006.01)
*A61K 39/00* (2006.01)
*A61K 47/68* (2017.01)
*A61P 35/00* (2006.01)

(52) U.S. Cl.
CPC ...... *C07K 16/2803* (2013.01); *A61K 47/6849* (2017.08); *A61P 35/00* (2018.01); *C07K 16/2818* (2013.01); *C07K 16/2827* (2013.01); *A61K 2039/507* (2013.01); *C07K 2317/21* (2013.01); *C07K 2317/33* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 11,267,886 B2 | 3/2022 | Darce et al. |
| 2007/0224627 A1 | 9/2007 | Horowitz et al. |
| 2014/0072577 A1 | 3/2014 | Sellman et al. |
| 2015/0139986 A1 | 5/2015 | Ponath et al. |

FOREIGN PATENT DOCUMENTS

WO 2016/144728 A2 9/2016

OTHER PUBLICATIONS

Rabia et al. 2018, Biochem. Eng. J. vol. 137: 365-374.*
Hall, 1992, J. Immunol. vol. 149: 1605-1612.*
Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
International Preliminary Report on Patentability for Application No. PCT/US2018/017546, dated Aug. 22, 2019, 7 pages.
International Search Report and Written Opinion for Application No. PCT/US2018/017546, dated Jun. 25, 2018, 10 pages.
U.S. Appl. No. 16/484,238, filed Aug. 7, 2019, U.S. Pat. No. 11,267,886, Issued.

* cited by examiner

*Primary Examiner* — Amy E Juedes
(74) *Attorney, Agent, or Firm* — McCarter & English, LLP; Marcie B. Clarke

(57) ABSTRACT

Disclosed herein are anti-immunoglobulin-like transcript-3 (ILT3) antibodies and antibody drug conjugates (ADCs), including compositions and methods of using said antibodies and ADCs.

22 Claims, 6 Drawing Sheets
Specification includes a Sequence Listing.

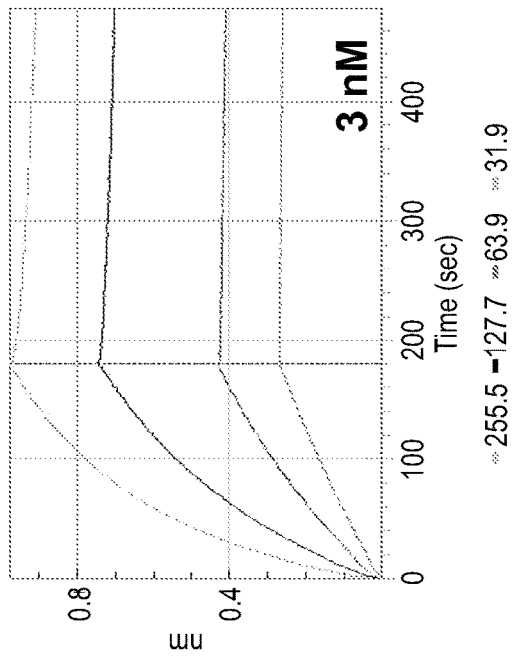
Figure 1A 1E2F12H8
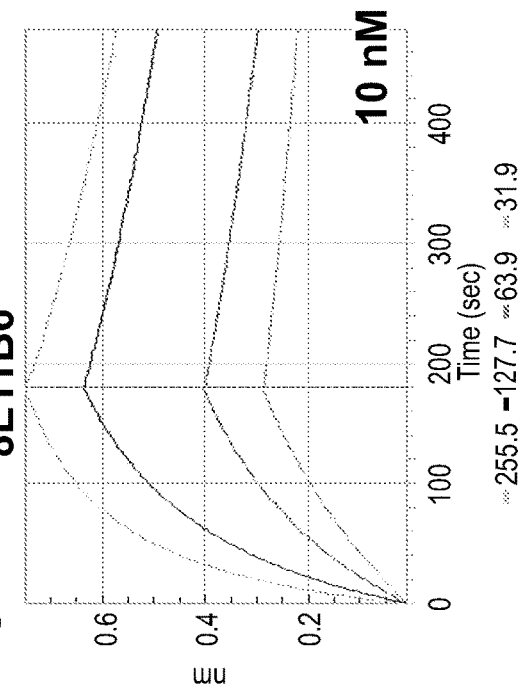
Figure 1B 1E12H10
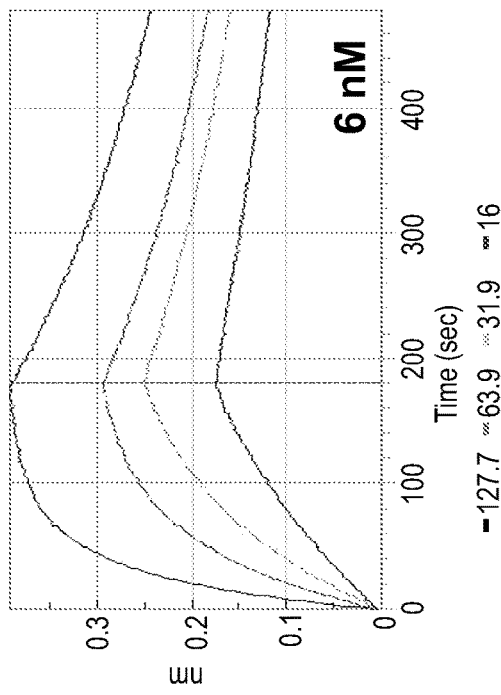
Figure 1C 3C4A3
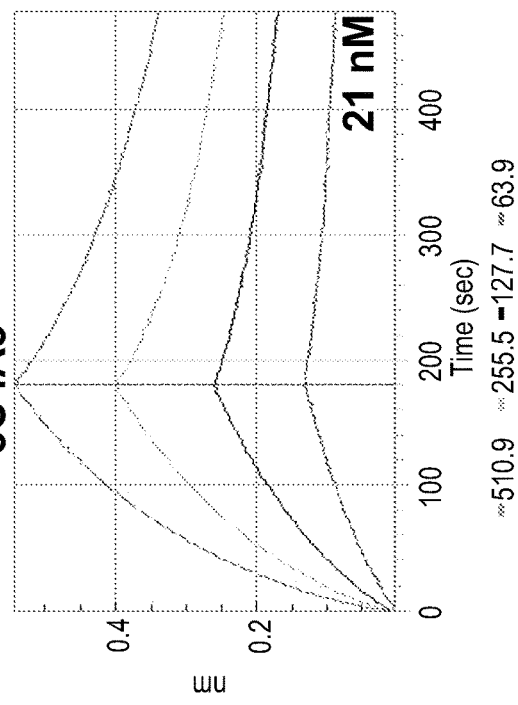
Figure 1D 8E11B6

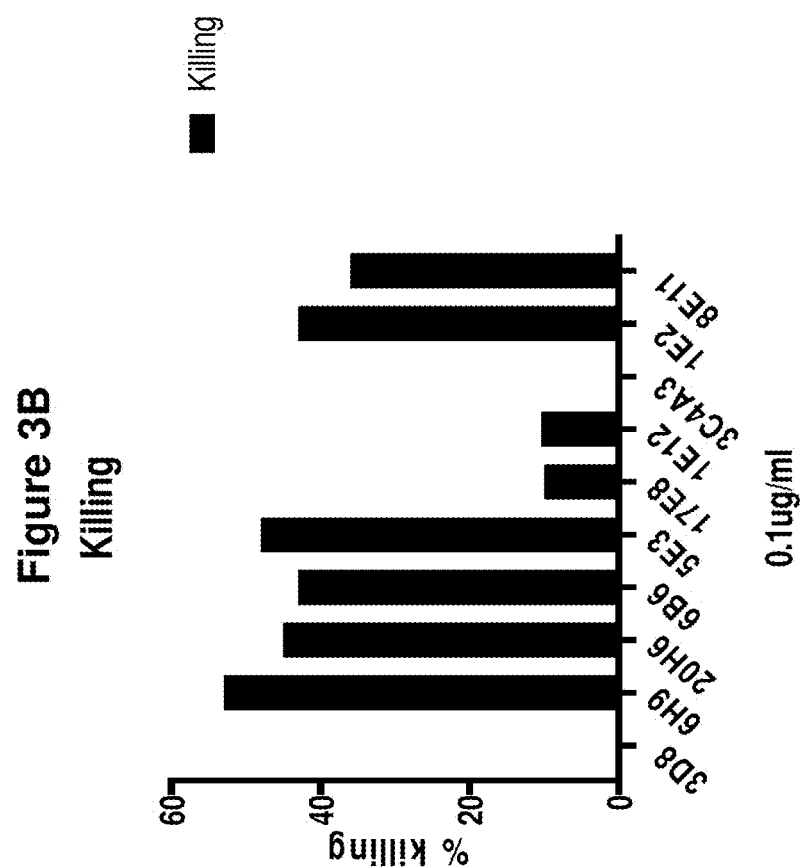
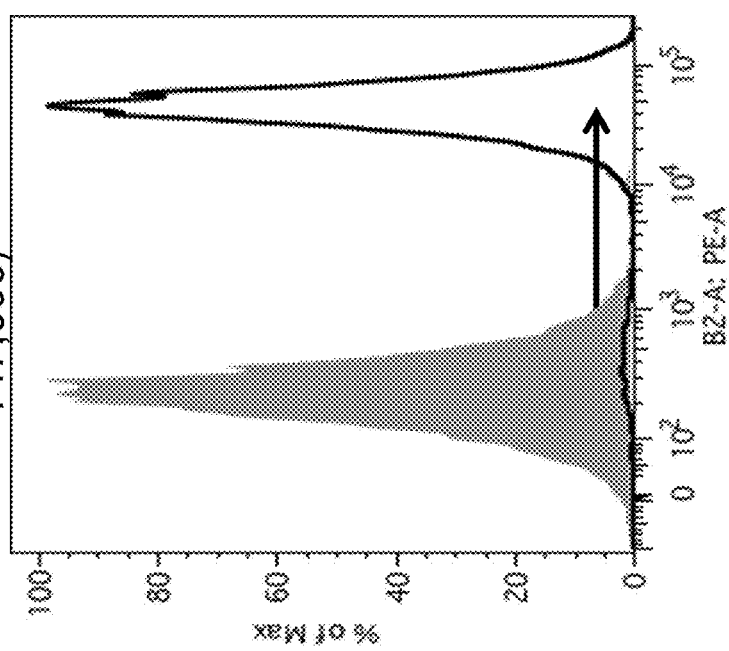

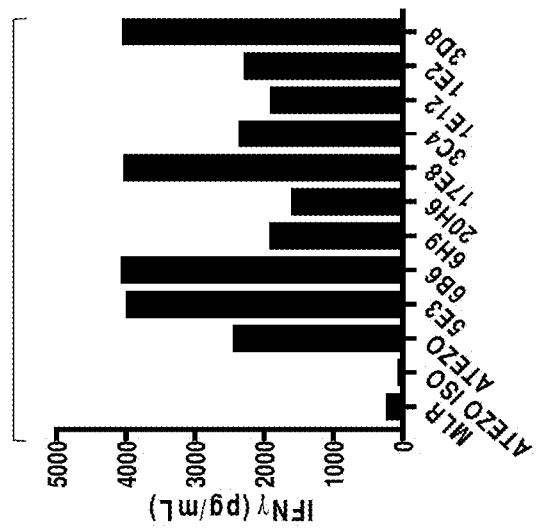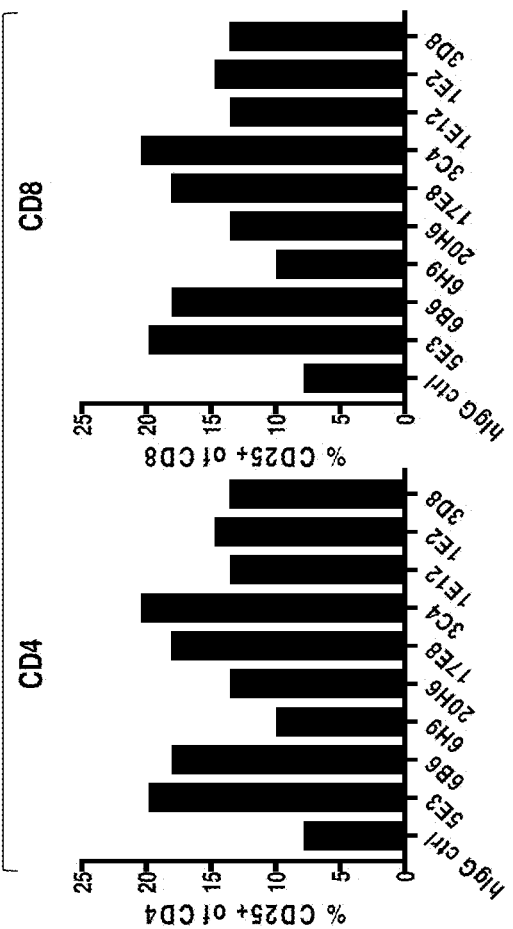

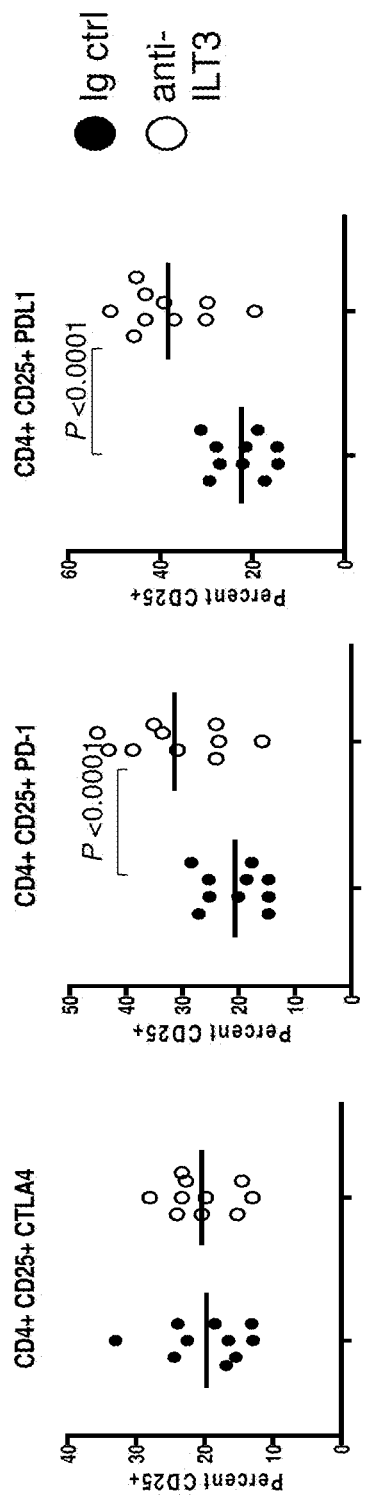
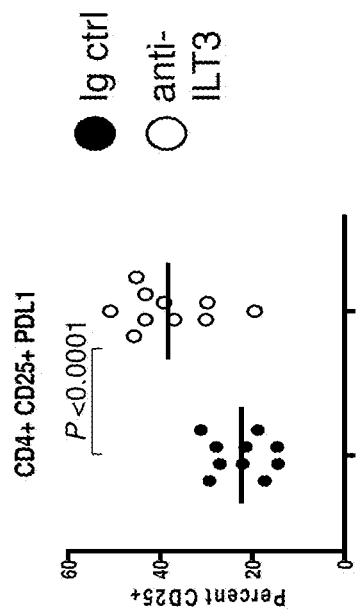
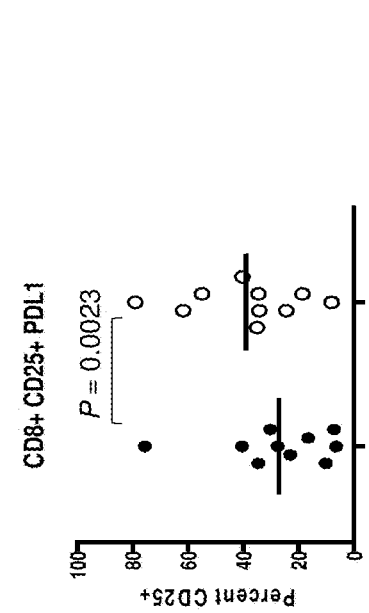
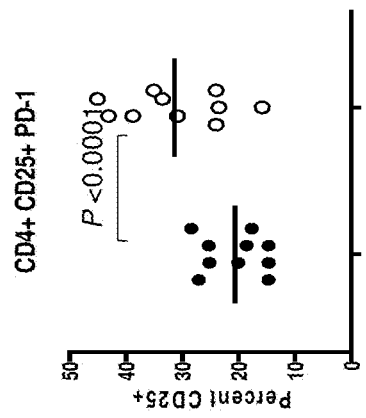
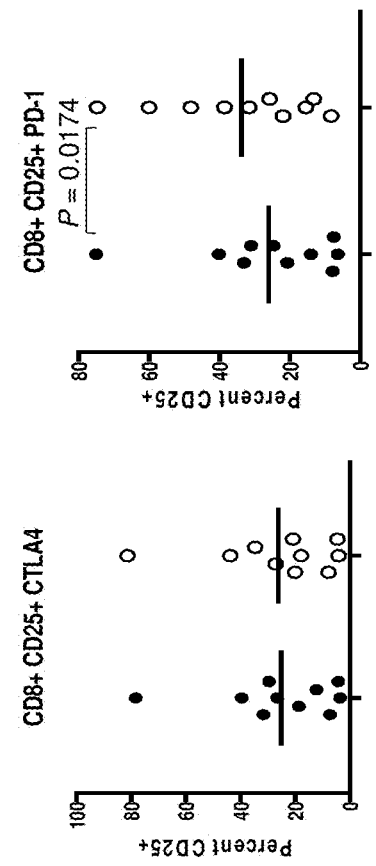

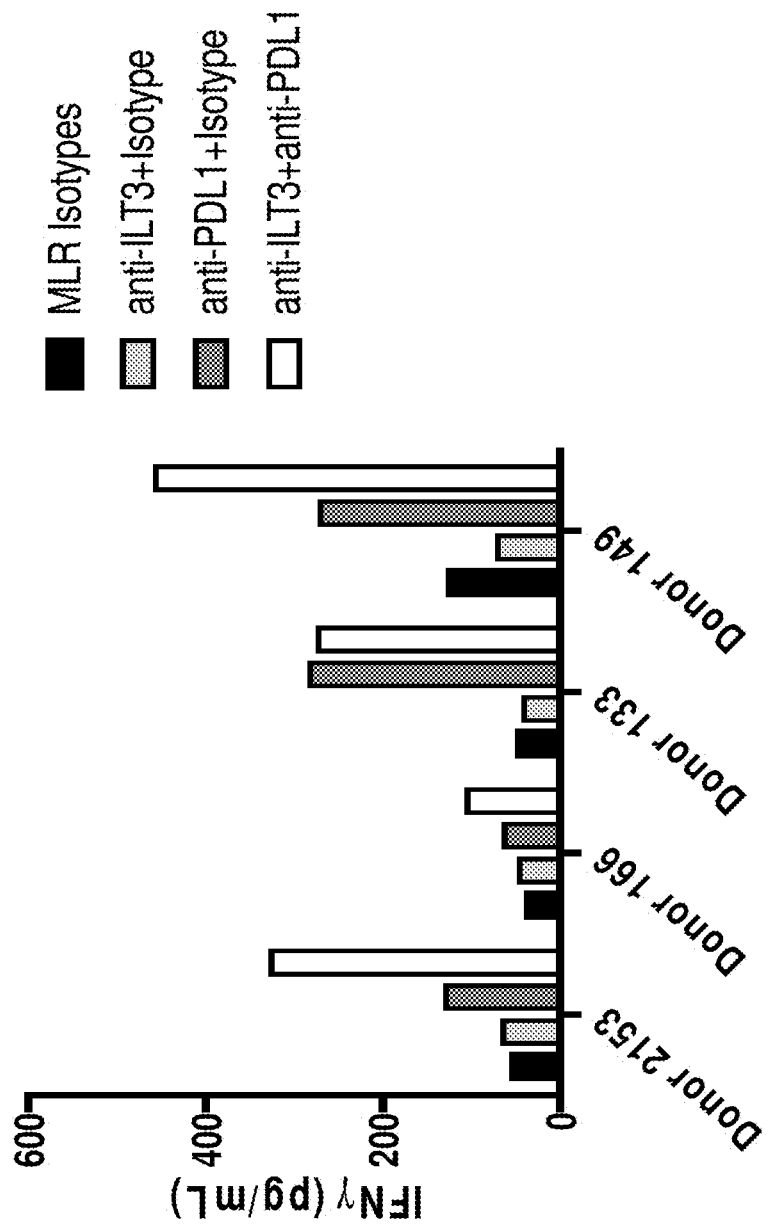

SEQUENCE LISTING

<160> NUMBER OF SEQ ID NOS: 175

<210> SEQ ID NO 1
<211> LENGTH: 119
<212> TYPE: PRT
<213> ORGANISM: Homo sapiens

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Ser Gly Ser Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asp Asp His Gly Asp Phe Phe Asp Tyr Trp Gly Gln Gly
            100                 105                 110

Thr Leu Val Thr Val Ser Ser
        115
```

<210> SEQ ID NO 2
<211> LENGTH: 10
<212> TYPE: PRT
<213> ORGANISM: Homo sapiens

<400> SEQUENCE: 2

```
Gly Phe Thr Phe Ser Ser Tyr Ala Met Ser
1               5                   10
```

<210> SEQ ID NO 3
<211> LENGTH: 17
<212> TYPE: PRT
<213> ORGANISM: Homo sapiens

<400> SEQUENCE: 3

```
Ile Ile Ser Gly Ser Gly Gly Asp Thr Tyr Tyr Ala Asp Ser Val Lys
1               5                   10                  15

Gly
```

<210> SEQ ID NO 4
<211> LENGTH: 10

<212> TYPE: PRT
<213> ORGANISM: Homo sapiens

<400> SEQUENCE: 4

Thr Asp Asp His Gly Asp Phe Phe Asp Tyr
1               5                   10

<210> SEQ ID NO 5
<211> LENGTH: 106
<212> TYPE: PRT
<213> ORGANISM: Homo sapiens

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 6
<211> LENGTH: 11
<212> TYPE: PRT
<213> ORGANISM: Homo sapiens

<400> SEQUENCE: 6

Arg Ala Ser Gln Ser Ile Ser Ser Trp Leu Ala
1               5                   10

<210> SEQ ID NO 7
<211> LENGTH: 7
<212> TYPE: PRT
<213> ORGANISM: Homo sapiens

<400> SEQUENCE: 7

Lys Ala Ser Ser Leu Glu Ser
1               5

<210> SEQ ID NO 8
<211> LENGTH: 8
<212> TYPE: PRT
<213> ORGANISM: Homo sapiens

<400> SEQUENCE: 8

Gln Gln Tyr Asn Ser Tyr Trp Thr
1               5

<210> SEQ ID NO 9
<211> LENGTH: 122
<212> TYPE: PRT
<213> ORGANISM: Homo sapiens

<400> SEQUENCE: 9

Gln Val Gln Leu Val Glu Ser Gly Gly Val Val Gln Pro Gly Arg
1               5                   10                  15

Ser Leu Arg Leu Ser Cys Ala Thr Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Phe Asp Gly Gly Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Phe Cys
            85                  90                  95

Ala Arg Asp Val Ile Ser Met Val Arg Gly Val Pro Phe Asp Tyr Trp
            100                 105                 110

Gly Gln Gly Thr Leu Val Thr Val Ser Ser
        115                 120

<210> SEQ ID NO 10
<211> LENGTH: 10
<212> TYPE: PRT
<213> ORGANISM: Homo sapiens

<400> SEQUENCE: 10

Gly Phe Thr Phe Ser Ser Tyr Gly Met His
1               5                   10

<210> SEQ ID NO 11
<211> LENGTH: 17
<212> TYPE: PRT
<213> ORGANISM: Homo sapiens

<400> SEQUENCE: 11

Leu Ile Trp Phe Asp Gly Gly Asn Gln Tyr Tyr Ala Asp Ser Val Lys
1               5                   10                  15

Gly

<210> SEQ ID NO 12
<211> LENGTH: 13
<212> TYPE: PRT
<213> ORGANISM: Homo sapiens

<400> SEQUENCE: 12

Asp Val Ile Ser Met Val Arg Gly Val Pro Phe Asp Tyr
1               5                   10

<210> SEQ ID NO 13
<211> LENGTH: 111
<212> TYPE: PRT
<213> ORGANISM: Homo sapiens

<400> SEQUENCE: 13

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Gly
            20                  25                  30

Asn Tyr Ala Asn Trp Val Gln Glu Lys Pro Asp His Leu Phe Thr Gly
        35                  40                  45

```
Leu Ile Gly Gly Ile Lys Asn Arg Val Pro Gly Val Pro Ala Arg Phe
     50                  55                  60
Ser Gly Ser Leu Ile Gly Asp Arg Ala Ala Leu Thr Ile Thr Gly Ala
 65                  70                  75                  80
Gln Thr Glu Asp Glu Ala Ile Tyr Phe Cys Ala Leu Trp Tyr Ser Asn
                 85                  90                  95
His Trp Val Phe Gly Gly Gly Thr Lys Leu Thr Val Leu Gly Gln
            100                 105                 110
```

<210> SEQ ID NO 14
<211> LENGTH: 14
<212> TYPE: PRT
<213> ORGANISM: Homo sapiens

<400> SEQUENCE: 14

```
Arg Ser Ser Thr Gly Ala Val Thr Thr Gly Asn Tyr Ala Asn
 1               5                  10
```

<210> SEQ ID NO 15
<211> LENGTH: 7
<212> TYPE: PRT
<213> ORGANISM: Homo sapiens

<400> SEQUENCE: 15

```
Gly Ile Lys Asn Arg Val Pro
 1               5
```

<210> SEQ ID NO 16
<211> LENGTH: 9
<212> TYPE: PRT
<213> ORGANISM: Homo sapiens

<400> SEQUENCE: 16

```
Ala Leu Trp Tyr Ser Asn His Trp Val
 1               5
```

<210> SEQ ID NO 17
<211> LENGTH: 119
<212> TYPE: PRT
<213> ORGANISM: Homo sapiens

<400> SEQUENCE: 17

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ser Val Ile Ser Gly Ser Gly Gly Ser Thr Tyr Tyr Ala Asp Ser Val
     50                  55                  60
Lys Gly Arg Phe Thr Ile Ser Arg Asp Asn Ser Lys Asn Thr Leu Asp
 65                  70                  75                  80
Leu Gln Met Asn Ser Leu Arg Ala Glu Asp Thr Ala Val Tyr Tyr Cys
                 85                  90                  95
Ala Lys Leu Gly Asp Tyr Tyr Tyr Gly Met Asp Val Trp Gly Gln Gly
            100                 105                 110
Thr Thr Val Thr Val Ser Ser
        115
```

<210> SEQ ID NO 18

```
<211> LENGTH: 16
<212> TYPE: PRT
<213> ORGANISM: Homo sapiens

<400> SEQUENCE: 18

Val Ile Ser Gly Ser Gly Gly Ser Thr Tyr Tyr Ala Asp Ser Val Lys
1               5                   10                  15

<210> SEQ ID NO 19
<211> LENGTH: 10
<212> TYPE: PRT
<213> ORGANISM: Homo sapiens

<400> SEQUENCE: 19

Leu Gly Asp Tyr Tyr Tyr Gly Met Asp Val
1               5                   10

<210> SEQ ID NO 20
<211> LENGTH: 112
<212> TYPE: PRT
<213> ORGANISM: Homo sapiens

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ala Pro Trp Thr Phe Gly Gln Gly Thr Lys Leu Glu Ile Lys
            100                 105                 110

<210> SEQ ID NO 21
<211> LENGTH: 16
<212> TYPE: PRT
<213> ORGANISM: Homo sapiens

<400> SEQUENCE: 21

Arg Ser Ser Gln Ser Leu Leu His Ser Asn Gly Tyr Asn Tyr Leu Asp
1               5                   10                  15

<210> SEQ ID NO 22
<211> LENGTH: 7
<212> TYPE: PRT
<213> ORGANISM: Homo sapiens

<400> SEQUENCE: 22

Leu Gly Ser Asn Arg Ala Ser
1               5

<210> SEQ ID NO 23
<211> LENGTH: 9
<212> TYPE: PRT
<213> ORGANISM: Homo sapiens
```

<400> SEQUENCE: 23

Met Gln Ala Leu Gln Ala Pro Trp Thr
1               5

<210> SEQ ID NO 24
<211> LENGTH: 120
<212> TYPE: PRT
<213> ORGANISM: Homo sapiens

<400> SEQUENCE: 24

Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Glu Thr Phe Phe Tyr Val Met Asp Ala Trp Gly Gln
            100                 105                 110

Gly Ala Ser Val Thr Val Ser Ser
        115                 120

<210> SEQ ID NO 25
<211> LENGTH: 17
<212> TYPE: PRT
<213> ORGANISM: Homo sapiens

<400> SEQUENCE: 25

Val Ile Trp Tyr Asp Gly Ser Asn Thr Tyr Tyr Ala Asp Ser Val Lys
1               5                   10                  15

Gly

<210> SEQ ID NO 26
<211> LENGTH: 11
<212> TYPE: PRT
<213> ORGANISM: Homo sapiens

<400> SEQUENCE: 26

Glu Arg Glu Thr Phe Phe Tyr Val Met Asp Ala
1               5                   10

<210> SEQ ID NO 27
<211> LENGTH: 106
<212> TYPE: PRT
<213> ORGANISM: Homo sapiens

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

```
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
 65                  70                  75                  80
Asp Asp Phe Ala Ile Tyr Tyr Cys Gln Gln Phe Asn Arg Phe Ile Thr
                 85                  90                  95
Phe Gly Gln Gly Thr Arg Leu Glu Ile Lys
            100                 105
```

<210> SEQ ID NO 28
<211> LENGTH: 8
<212> TYPE: PRT
<213> ORGANISM: Homo sapiens

<400> SEQUENCE: 28

```
Gln Gln Phe Asn Arg Phe Ile Thr
 1               5
```

<210> SEQ ID NO 29
<211> LENGTH: 122
<212> TYPE: PRT
<213> ORGANISM: Homo sapiens

<400> SEQUENCE: 29

```
Gln Val Gln Leu Val Glu Ser Gly Gly Val Val Gln Pro Gly Arg
 1               5                  10                  15
Ser Leu Arg Leu Ser Cys Ala Ala Ser Gly Phe Thr Phe Ser Asn Tyr
                 20                  25                  30
Gly Met His Trp Val Arg Gln Ala Pro Gly Lys Gly Leu Glu Trp Met
             35                  40                  45
Ala Gly Ile Trp Phe Asp Gly Thr Asn Lys Tyr Tyr Ile Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Asn Leu Arg Ala Glu Asp Thr Ala Val Tyr Tyr Cys
                 85                  90                  95
Ala Arg Asp Val Ile Ser Met Val Arg Gly Val Pro Phe Asp Tyr Trp
            100                 105                 110
Gly Gln Gly Thr Leu Val Thr Val Ser Ser
            115                 120
```

<210> SEQ ID NO 30
<211> LENGTH: 10
<212> TYPE: PRT
<213> ORGANISM: Homo sapiens

<400> SEQUENCE: 30

```
Gly Phe Thr Phe Ser Asn Tyr Gly Met His
 1               5                  10
```

<210> SEQ ID NO 31
<211> LENGTH: 17
<212> TYPE: PRT
<213> ORGANISM: Homo sapiens

<400> SEQUENCE: 31

```
Gly Ile Trp Phe Asp Gly Thr Asn Lys Tyr Tyr Ile Asp Ser Val Lys
 1               5                  10                  15
Gly
```

<210> SEQ ID NO 32
<211> LENGTH: 114
<212> TYPE: PRT
<213> ORGANISM: Homo sapiens

<400> SEQUENCE: 32

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Ile Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ala

<210> SEQ ID NO 33
<211> LENGTH: 14
<212> TYPE: PRT
<213> ORGANISM: Homo sapiens

<400> SEQUENCE: 33

Arg Ser Ser Thr Gly Ala Val Thr Thr Ser Asn Tyr Ala Asn
1               5                   10

<210> SEQ ID NO 34
<211> LENGTH: 7
<212> TYPE: PRT
<213> ORGANISM: Homo sapiens

<400> SEQUENCE: 34

Gly Ile Asn Asn Arg Ala Pro
1               5

<210> SEQ ID NO 35
<211> LENGTH: 122
<212> TYPE: PRT
<213> ORGANISM: Homo sapiens

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Ile His Trp Val Arg Gln Ala Pro Gly Lys Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp Val Ile Ser Met Val Arg Gly Val Pro Phe Asp Tyr Trp
            100                 105                 110

Gly Gln Gly Thr Leu Val Thr Val Ser Ser
        115                 120
```

<210> SEQ ID NO 36
<211> LENGTH: 10
<212> TYPE: PRT
<213> ORGANISM: Homo sapiens

<400> SEQUENCE: 36

```
Gly Phe Thr Phe Ser Thr Tyr Gly Ile His
1               5                   10
```

<210> SEQ ID NO 37
<211> LENGTH: 17
<212> TYPE: PRT
<213> ORGANISM: Homo sapiens

<400> SEQUENCE: 37

```
Val Ile Trp Phe Asp Gly Ser Asn Lys Tyr Tyr Ala Asp Ser Val Lys
1               5                   10                  15

Gly
```

<210> SEQ ID NO 38
<211> LENGTH: 114
<212> TYPE: PRT
<213> ORGANISM: Homo sapiens

<400> SEQUENCE: 38

```
Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Ile Asn Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Val Thr Val Leu Gly Gln Pro
            100                 105                 110

Lys Ala
```

<210> SEQ ID NO 39
<211> LENGTH: 7
<212> TYPE: PRT
<213> ORGANISM: Homo sapiens

<400> SEQUENCE: 39

```
Gly Ile Asn Asn Arg Val Pro
1               5
```

<210> SEQ ID NO 40
<211> LENGTH: 122
<212> TYPE: PRT
<213> ORGANISM: Homo sapiens

```
<400> SEQUENCE: 40

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Ile His Trp Val Arg Gln Ala Pro Gly Lys Gly Leu Glu Trp Val
            35                  40                  45

Ala Val Ile Trp Phe Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Ile Thr Leu Val Arg Gly Val Pro Phe Asp Tyr Trp
            100                 105                 110

Gly Gln Gly Thr Leu Val Thr Val Ser Ser
        115                 120

<210> SEQ ID NO 41
<211> LENGTH: 10
<212> TYPE: PRT
<213> ORGANISM: Homo sapiens

<400> SEQUENCE: 41

Gly Phe Thr Phe Ser Asn Tyr Gly Ile His
1               5                   10

<210> SEQ ID NO 42
<211> LENGTH: 17
<212> TYPE: PRT
<213> ORGANISM: Homo sapiens

<400> SEQUENCE: 42

Val Ile Trp Phe Asp Gly Asn Asn Lys Tyr Tyr Ala Asp Ser Val Lys
1               5                   10                  15

Gly

<210> SEQ ID NO 43
<211> LENGTH: 13
<212> TYPE: PRT
<213> ORGANISM: Homo sapiens

<400> SEQUENCE: 43

Asp Val Ile Thr Leu Val Arg Gly Val Pro Phe Asp Tyr
1               5                   10

<210> SEQ ID NO 44
<211> LENGTH: 113
<212> TYPE: PRT
<213> ORGANISM: Homo sapiens

<400> SEQUENCE: 44

Asp Ala Val Val Thr Gln Glu Ser Ala Leu Thr Thr Ser Pro Gly Glu
1               5                   10                  15

Thr Val Thr Val Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45
```

```
Leu Ile Gly Gly Ile Asn Asn Arg Ala Pro Gly Val Pro Ala Arg Phe
    50                  55                  60
Ser Gly Ser Leu Ile Gly Asp Lys Ala Ala Leu Thr Ile Thr Gly Ala
 65                  70                  75                  80
Gln Thr Glu Asp Glu Ala Ile Tyr Phe Cys Ala Leu Trp Tyr Ser Asn
                 85                  90                  95
His Trp Val Phe Gly Gly Gly Thr Lys Leu Thr Val Leu Gly Gln Pro
            100                 105                 110
Lys

<210> SEQ ID NO 45
<211> LENGTH: 123
<212> TYPE: PRT
<213> ORGANISM: Homo sapiens

<400> SEQUENCE: 45

Gln Val Gln Leu Gln Glu Ala Gly Pro Gly Leu Val Asn Pro Ser Lys
 1               5                  10                  15
Thr Leu Ser Leu Thr Cys Thr Val Ser Gly Gly Ser Ile Ser Ser Tyr
             20                  25                  30
Phe Trp Ser Trp Ile Arg Gln Pro Pro Gly Lys Gly Leu Glu Trp Ile
         35                  40                  45
Gly Tyr Ile Tyr Asn Ser Gly Ser Thr Asn Tyr Asn Pro Ser Leu Gln
     50                  55                  60
Ser Arg Val Thr Ile Ser Val Asp Met Ser Lys Asn His Phe Ser Leu
 65                  70                  75                  80
Lys Leu Ser Ser Val Thr Ala Ala Asp Thr Ala Val Tyr Tyr Cys Ala
                 85                  90                  95
Arg Arg Gly Gly Tyr Tyr Gly Ser Gly Asn Tyr Gly Gly Met Asp Val
            100                 105                 110
Trp Gly Gln Gly Thr Thr Val Thr Val Ser Ser
        115                 120

<210> SEQ ID NO 46
<211> LENGTH: 10
<212> TYPE: PRT
<213> ORGANISM: Homo sapiens

<400> SEQUENCE: 46

Gly Gly Ser Ile Ser Ser Tyr Phe Trp Ser
 1               5                  10

<210> SEQ ID NO 47
<211> LENGTH: 16
<212> TYPE: PRT
<213> ORGANISM: Homo sapiens

<400> SEQUENCE: 47

Tyr Ile Tyr Asn Ser Gly Ser Thr Asn Tyr Asn Pro Ser Leu Gln Ser
 1               5                  10                  15

<210> SEQ ID NO 48
<211> LENGTH: 15
<212> TYPE: PRT
<213> ORGANISM: Homo sapiens

<400> SEQUENCE: 48

Arg Gly Gly Tyr Tyr Gly Ser Gly Asn Tyr Gly Gly Met Asp Val
 1               5                  10                  15
```

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Met
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys
            100                 105

<210> SEQ ID NO 50
<211> LENGTH: 11
<212> TYPE: PRT
<213> ORGANISM: Homo sapiens

<400> SEQUENCE: 50

Arg Ala Ser Gln Gly Ile Ser Asn Tyr Leu Ala
1               5                   10

<210> SEQ ID NO 51
<211> LENGTH: 7
<212> TYPE: PRT
<213> ORGANISM: Homo sapiens

<400> SEQUENCE: 51

Ala Ala Ser Ala Leu Gln Ser
1               5

<210> SEQ ID NO 52
<211> LENGTH: 9
<212> TYPE: PRT
<213> ORGANISM: Homo sapiens

<400> SEQUENCE: 52

Gln Lys Tyr Asp Ser Ala Pro Trp Thr
1               5

<210> SEQ ID NO 53
<211> LENGTH: 121
<212> TYPE: PRT
<213> ORGANISM: Homo sapiens

<400> SEQUENCE: 53

Gln Val Gln Leu Gln Glu Ser Gly Pro Gly Leu Leu Lys Pro Ser Glu
1               5                   10                  15

Thr Leu Ser Leu Thr Cys Thr Val Ser Gly Gly Ser Ile Ser Pro Tyr
            20                  25                  30

Tyr Trp Ser Trp Ile Arg Gln Pro Pro Gly Lys Gly Leu Glu Trp Ile
        35                  40                  45

```
Gly Tyr Ile Tyr Tyr Ser Gly Asn Thr Asn Tyr Asn Pro Ser Leu Gln
            50                  55                  60

Ser Arg Leu Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Gly Tyr Ser Phe Gly Phe Tyr Tyr Gly Leu Asp Val Trp Gly
                100                 105                 110

Gln Gly Thr Thr Val Thr Val Ser Ser
            115                 120

<210> SEQ ID NO 54
<211> LENGTH: 10
<212> TYPE: PRT
<213> ORGANISM: Homo sapiens

<400> SEQUENCE: 54

Gly Gly Ser Ile Ser Pro Tyr Tyr Trp Ser
 1               5                  10

<210> SEQ ID NO 55
<211> LENGTH: 16
<212> TYPE: PRT
<213> ORGANISM: Homo sapiens

<400> SEQUENCE: 55

Tyr Ile Tyr Tyr Ser Gly Asn Thr Asn Tyr Asn Pro Ser Leu Gln Ser
 1               5                  10                  15

<210> SEQ ID NO 56
<211> LENGTH: 13
<212> TYPE: PRT
<213> ORGANISM: Homo sapiens

<400> SEQUENCE: 56

Arg Gly Tyr Ser Phe Gly Phe Tyr Tyr Gly Leu Asp Val
 1               5                  10

<210> SEQ ID NO 57
<211> LENGTH: 107
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ile Tyr
                 20                  25                  30

Leu Ala Trp Tyr Gln Gln Lys Pro Gly Lys Val Pro Asn Leu Leu Ile
             35                  40                  45

Tyr Leu Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Trp
                 85                  90                  95

Thr Phe Gly Gln Gly Thr Lys Leu Glu Ile Lys
                100                 105

<210> SEQ ID NO 58
```

<211> LENGTH: 11
<212> TYPE: PRT
<213> ORGANISM: Homo sapiens

<400> SEQUENCE: 58

Arg Ala Ser Gln Asp Ile Ser Ile Tyr Leu Ala
1               5                   10

<210> SEQ ID NO 59
<211> LENGTH: 7
<212> TYPE: PRT
<213> ORGANISM: Homo sapiens

<400> SEQUENCE: 59

Leu Ala Ser Thr Leu Gln Ser
1               5

<210> SEQ ID NO 60
<211> LENGTH: 9
<212> TYPE: PRT
<213> ORGANISM: Homo sapiens

<400> SEQUENCE: 60

Gln Lys Tyr Asn Ser Ala Pro Trp Thr
1               5

<210> SEQ ID NO 61
<211> LENGTH: 121
<212> TYPE: PRT
<213> ORGANISM: Homo sapiens

<400> SEQUENCE: 61

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Gly Ser Thr Asn Tyr Asn Pro Ser Leu Lys
    50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Tyr Ser Tyr Gly Tyr Tyr Gly Met Asp Val Trp Gly
            100                 105                 110

Gln Gly Thr Thr Val Thr Val Ser Ser
        115                 120

<210> SEQ ID NO 62
<211> LENGTH: 10
<212> TYPE: PRT
<213> ORGANISM: Homo sapiens

<400> SEQUENCE: 62

Gly Gly Ser Ile Ser Ser Tyr Tyr Trp Ser
1               5                   10

<210> SEQ ID NO 63
<211> LENGTH: 16
<212> TYPE: PRT
<213> ORGANISM: Homo sapiens

```
<400> SEQUENCE: 63

Tyr Ile Tyr Tyr Ser Gly Ser Thr Asn Tyr Asn Pro Ser Leu Lys Ser
1               5                   10                  15

<210> SEQ ID NO 64
<211> LENGTH: 13
<212> TYPE: PRT
<213> ORGANISM: Homo sapiens

<400> SEQUENCE: 64

Arg Gly Tyr Ser Tyr Gly Tyr Tyr Gly Met Asp Val
1               5                   10

<210> SEQ ID NO 65
<211> LENGTH: 107
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Ser Pro Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Leu Glu Ile Lys
            100                 105

<210> SEQ ID NO 66
<211> LENGTH: 11
<212> TYPE: PRT
<213> ORGANISM: Homo sapiens

<400> SEQUENCE: 66

Arg Ala Ser Gln Asp Ile Ser Asn Tyr Leu Ala
1               5                   10

<210> SEQ ID NO 67
<211> LENGTH: 7
<212> TYPE: PRT
<213> ORGANISM: Homo sapiens

<400> SEQUENCE: 67

Pro Ala Ser Thr Leu Gln Ser
1               5

<210> SEQ ID NO 68
<211> LENGTH: 123
<212> TYPE: PRT
<213> ORGANISM: Homo sapiens

<400> SEQUENCE: 68

Gln Val Gln Leu Gln Glu Ser Gly Pro Gly Leu Val Asn Pro Ser Lys
1               5                   10                  15
```

```
Thr Leu Ser Leu Thr Cys Thr Val Ser Gly Gly Ser Ile Ser Arg Tyr
            20                  25                  30

Phe Trp Ser Trp Ile Arg Gln Pro Pro Gly Lys Gly Leu Glu Trp Ile
        35                  40                  45

Gly Tyr Ile Tyr Asp Ser Gly Ser Thr Asn Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Arg Gly Gly Tyr Tyr Gly Ser Gly Ser Tyr Gly Gly Met Asp Val
            100                 105                 110

Trp Gly Gln Gly Thr Thr Val Thr Val Ser Ser
            115                 120

<210> SEQ ID NO 69
<211> LENGTH: 10
<212> TYPE: PRT
<213> ORGANISM: Homo sapiens

<400> SEQUENCE: 69

Gly Gly Ser Ile Ser Arg Tyr Phe Trp Ser
1               5                   10

<210> SEQ ID NO 70
<211> LENGTH: 16
<212> TYPE: PRT
<213> ORGANISM: Homo sapiens

<400> SEQUENCE: 70

Tyr Ile Tyr Asp Ser Gly Ser Thr Asn Tyr Asn Pro Ser Leu Lys Ser
1               5                   10                  15

<210> SEQ ID NO 71
<211> LENGTH: 15
<212> TYPE: PRT
<213> ORGANISM: Homo sapiens

<400> SEQUENCE: 71

Arg Gly Gly Tyr Tyr Gly Ser Gly Ser Tyr Gly Gly Met Asp Val
1               5                   10                  15

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ile Pro Lys Leu Leu Ile
        35                  40                  45

Ser Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95
```

```
Thr Phe Gly Gln Gly Thr Lys Val Glu Ile Lys
            100                 105
```

<210> SEQ ID NO 73
<211> LENGTH: 7
<212> TYPE: PRT
<213> ORGANISM: Homo sapiens

<400> SEQUENCE: 73

```
Ala Ala Ser Thr Leu Gln Ser
1               5
```

<210> SEQ ID NO 74
<211> LENGTH: 121
<212> TYPE: PRT
<213> ORGANISM: Homo sapiens

<400> SEQUENCE: 74

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Asn Trp Ile Arg Gln Pro Pro Gly Lys Gly Leu Glu Trp Ile
        35                  40                  45

Gly Tyr Ile His Tyr Ser Gly Gly Thr Asn Tyr Asn Pro Ser Gln Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Arg Arg Tyr Tyr Phe Asp Ser Ser Gly Tyr Leu Asp Tyr Trp Gly
            100                 105                 110

Gln Gly Thr Leu Val Thr Val Ser Ser
        115                 120
```

<210> SEQ ID NO 75
<211> LENGTH: 10
<212> TYPE: PRT
<213> ORGANISM: Homo sapiens

<400> SEQUENCE: 75

```
Gly Gly Ser Ile Ser Ser His Tyr Trp Asn
1               5                   10
```

<210> SEQ ID NO 76
<211> LENGTH: 16
<212> TYPE: PRT
<213> ORGANISM: Homo sapiens

<400> SEQUENCE: 76

```
Tyr Ile His Tyr Ser Gly Gly Thr Asn Tyr Asn Pro Ser Gln Lys Ser
1               5                   10                  15
```

<210> SEQ ID NO 77
<211> LENGTH: 13
<212> TYPE: PRT
<213> ORGANISM: Homo sapiens

<400> SEQUENCE: 77

```
Arg Arg Tyr Tyr Phe Asp Ser Ser Gly Tyr Leu Asp Tyr
1               5                   10
```

<210> SEQ ID NO 78
<211> LENGTH: 107
<212> TYPE: PRT
<213> ORGANISM: Homo sapiens

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ile Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Leu Glu Ile Lys
            100                 105

<210> SEQ ID NO 79
<211> LENGTH: 123
<212> TYPE: PRT
<213> ORGANISM: Homo sapiens

<400> SEQUENCE: 79

Gln Val Gln Leu Gln Glu Ser Gly Pro Gly Leu Val Asn Pro Ser Lys
1               5                   10                  15

Thr Leu Ser Leu Thr Cys Thr Val Ser Gly Gly Ser Ile Ser Ser Tyr
            20                  25                  30

Phe Trp Ser Trp Ile Arg Gln Pro Pro Gly Lys Gly Leu Glu Trp Ile
        35                  40                  45

Gly Tyr Ile Tyr Asp Ser Gly Ser Thr Asn Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Arg Gly Gly Tyr Tyr Gly Ser Gly Ser Tyr Gly Gly Met Asp Val
            100                 105                 110

Trp Gly Gln Gly Thr Thr Val Thr Val Ser Ser
        115                 120

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

```
Ser Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Lys Tyr Asn Ser Ala Pro Trp
                85                  90                  95
Thr Phe Gly Gln Gly Thr Lys Leu Glu Ile Lys
                100                 105
```

<210> SEQ ID NO 81
<211> LENGTH: 123
<212> TYPE: PRT
<213> ORGANISM: Homo sapiens

<400> SEQUENCE: 81

```
Gln Val Glu Leu Gln Gln Ser Gly Pro Gly Leu Val Lys Pro Ser Glu
1               5                   10                  15
Thr Leu Ser Leu Thr Cys Thr Val Ser Gly Gly Ser Ile Ser Thr Tyr
            20                  25                  30
Phe Trp Ser Trp Thr Arg Gln Pro Pro Gly Lys Gly Leu Glu Trp Ile
        35                  40                  45
Gly Tyr Thr Asn Tyr Arg Gly Asn Thr Asn Tyr Asn Pro Ser Leu Glu
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Arg Gly Gly Tyr Tyr Gly Ser Gly Asn Tyr Gly Gly Met Asp Val
                100                 105                 110
Trp Gly Gln Gly Thr Thr Val Thr Val Ser Ser
        115                 120
```

<210> SEQ ID NO 82
<211> LENGTH: 10
<212> TYPE: PRT
<213> ORGANISM: Homo sapiens

<400> SEQUENCE: 82

```
Gly Gly Ser Ile Ser Thr Tyr Phe Trp Ser
1               5                   10
```

<210> SEQ ID NO 83
<211> LENGTH: 16
<212> TYPE: PRT
<213> ORGANISM: Homo sapiens

<400> SEQUENCE: 83

```
Tyr Thr Asn Tyr Arg Gly Asn Thr Asn Tyr Asn Pro Ser Leu Glu Ser
1               5                   10                  15
```

<210> SEQ ID NO 84
<211> LENGTH: 107
<212> TYPE: PRT
<213> ORGANISM: Homo sapiens

<400> SEQUENCE: 84

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
            20                  25                  30
```

```
Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Lys Tyr Asp Ser Ala Pro Trp
                 85                  90                  95

Thr Phe Gly Gln Gly Thr Lys Leu Glu Ile Lys
            100                 105
```

<210> SEQ ID NO 85
<211> LENGTH: 123
<212> TYPE: PRT
<213> ORGANISM: Homo sapiens

<400> SEQUENCE: 85

```
Gln Leu Gln Leu Gln Glu Ser Gly Pro Gly Leu Val Asn Pro Ser Lys
 1               5                  10                  15

Thr Leu Ser Leu Thr Cys Asn Val Ser Gly Gly Ser Met Ser Asn Tyr
            20                  25                  30

Phe Trp Ser Trp Ile Arg Gln Pro Pro Gly Lys Gly Leu Glu Trp Ile
         35                  40                  45

Gly Tyr Ile Tyr Asn Ser Gly Asn Thr Asn Tyr His Pro Ser Leu Gln
 50                  55                  60

Ser Arg Val Thr Ile Ser Val Asp Thr Ser Lys Asn Leu Phe Ser Leu
 65                  70                  75                  80

Lys Leu Thr Ser Val Thr Ala Ala Asp Thr Ala Val Tyr Tyr Cys Ala
                 85                  90                  95

Arg Arg Gly Gly Tyr Tyr Gly Ser Gly Asn Tyr Gly Gly Leu Asp Val
            100                 105                 110

Trp Gly His Gly Thr Thr Val Thr Val Ser Ser
         115                 120
```

<210> SEQ ID NO 86
<211> LENGTH: 10
<212> TYPE: PRT
<213> ORGANISM: Homo sapiens

<400> SEQUENCE: 86

```
Gly Gly Ser Met Ser Asn Tyr Phe Trp Ser
 1               5                  10
```

<210> SEQ ID NO 87
<211> LENGTH: 16
<212> TYPE: PRT
<213> ORGANISM: Homo sapiens

<400> SEQUENCE: 87

```
Tyr Ile Tyr Asn Ser Gly Asn Thr Asn Tyr His Pro Ser Leu Gln Ser
 1               5                  10                  15
```

<210> SEQ ID NO 88
<211> LENGTH: 15
<212> TYPE: PRT
<213> ORGANISM: Homo sapiens

<400> SEQUENCE: 88

Arg Gly Gly Tyr Tyr Gly Ser Gly Asn Tyr Gly Gly Leu Asp Val
1               5                   10                  15

<210> SEQ ID NO 89
<211> LENGTH: 107
<212> TYPE: PRT
<213> ORGANISM: Homo sapiens

<400> SEQUENCE: 89

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Thr Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys
            100                 105

<210> SEQ ID NO 90
<211> LENGTH: 121
<212> TYPE: PRT
<213> ORGANISM: Homo sapiens

<400> SEQUENCE: 90

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Ile Ile Trp Asn Asp Gly Ser Asn Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ser Ser Ser Trp Phe Val Asn Tyr Phe Asp Tyr Trp Gly
            100                 105                 110

Gln Gly Thr Leu Val Thr Val Ser Ser
        115                 120

<210> SEQ ID NO 91
<211> LENGTH: 10
<212> TYPE: PRT
<213> ORGANISM: Homo sapiens

<400> SEQUENCE: 91

Gly Phe Thr Phe Asn Asn Tyr Gly Met His
1               5                   10

```
<210> SEQ ID NO 92
<211> LENGTH: 17
<212> TYPE: PRT
<213> ORGANISM: Homo sapiens

<400> SEQUENCE: 92

Ile Ile Trp Asn Asp Gly Ser Asn Pro Tyr Tyr Ala Asp Ser Val Lys
1               5                   10                  15

Gly

<210> SEQ ID NO 93
<211> LENGTH: 12
<212> TYPE: PRT
<213> ORGANISM: Homo sapiens

<400> SEQUENCE: 93

Asp Ser Ser Ser Trp Phe Val Asn Tyr Phe Asp Tyr
1               5                   10

<210> SEQ ID NO 94
<211> LENGTH: 107
<212> TYPE: PRT
<213> ORGANISM: Homo sapiens

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Ser Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn His Trp Pro Leu
                85                  90                  95

Thr Phe Gly Gly Gly Thr Lys Val Glu Ile Lys
            100                 105

<210> SEQ ID NO 95
<211> LENGTH: 11
<212> TYPE: PRT
<213> ORGANISM: Homo sapiens

<400> SEQUENCE: 95

Arg Ala Ser Gln Ser Val Asn Arg Asn Leu Ala
1               5                   10

<210> SEQ ID NO 96
<211> LENGTH: 7
<212> TYPE: PRT
<213> ORGANISM: Homo sapiens

<400> SEQUENCE: 96

Gly Ala Ser Thr Arg Ala Thr
1               5

<210> SEQ ID NO 97
<211> LENGTH: 9
<212> TYPE: PRT
<213> ORGANISM: Homo sapiens
```

<400> SEQUENCE: 97

Gln His Tyr Asn His Trp Pro Leu Thr
1               5

<210> SEQ ID NO 98
<211> LENGTH: 123
<212> TYPE: PRT
<213> ORGANISM: Homo sapiens

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Gly Tyr Ser Tyr Gly Tyr Gly Tyr Tyr Gly Met Asp Val
            100                 105                 110

Trp Gly Gln Gly Thr Thr Val Thr Val Ser Ser
        115                 120

<210> SEQ ID NO 99
<211> LENGTH: 14
<212> TYPE: PRT
<213> ORGANISM: Homo sapiens

<400> SEQUENCE: 99

Gly Gly Tyr Ser Tyr Gly Tyr Gly Tyr Tyr Gly Met Asp Val
1               5                   10

<210> SEQ ID NO 100
<211> LENGTH: 107
<212> TYPE: PRT
<213> ORGANISM: Homo sapiens

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Leu Glu Ile Lys
            100                 105

```
<210> SEQ ID NO 101
<211> LENGTH: 123
<212> TYPE: PRT
<213> ORGANISM: Homo sapiens

<400> SEQUENCE: 101

Gln Ile Gln Leu Gln Glu Ser Gly Pro Gly Leu Val Asn Pro Ser Lys
1               5                   10                  15

Thr Leu Ser Leu Thr Cys Thr Val Ser Gly Gly Ser Ile Arg Ser Tyr
            20                  25                  30

Phe Trp Ser Trp Ile Arg Gln Pro Pro Gly Lys Gly Leu Glu Trp Ile
        35                  40                  45

Gly Tyr Ile Tyr Asp Ser Gly Asn Thr Asn Tyr Asn Pro Ser Leu Lys
50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Arg Gly Gly Tyr Tyr Gly Ser Gly Asn Tyr Gly Gly Met Asp Val
            100                 105                 110

Trp Gly Gln Gly Thr Thr Val Thr Val Ser Ser
        115                 120

<210> SEQ ID NO 102
<211> LENGTH: 10
<212> TYPE: PRT
<213> ORGANISM: Homo sapiens

<400> SEQUENCE: 102

Gly Gly Ser Ile Arg Ser Tyr Phe Trp Ser
1               5                   10

<210> SEQ ID NO 103
<211> LENGTH: 16
<212> TYPE: PRT
<213> ORGANISM: Homo sapiens

<400> SEQUENCE: 103

Tyr Ile Tyr Asp Ser Gly Asn Thr Asn Tyr Asn Pro Ser Leu Lys Ser
1               5                   10                  15

<210> SEQ ID NO 104
<211> LENGTH: 121
<212> TYPE: PRT
<213> ORGANISM: Homo sapiens

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile His Tyr Ser Gly Ser Thr Asn Tyr Asn Pro Ser Leu Lys
50                  55                  60

Ser Arg Val Thr Ile Ser Glu Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95
```

Gly Arg Arg Tyr Tyr Phe Asp Ser Ser Gly Tyr Phe Asp Tyr Trp Gly
                100                 105                 110

Gln Gly Thr Leu Val Thr Val Ser Ser
        115                 120

<210> SEQ ID NO 105
<211> LENGTH: 16
<212> TYPE: PRT
<213> ORGANISM: Homo sapiens

<400> SEQUENCE: 105

Tyr Ile His Tyr Ser Gly Ser Thr Asn Tyr Asn Pro Ser Leu Lys Ser
1               5                   10                  15

<210> SEQ ID NO 106
<211> LENGTH: 13
<212> TYPE: PRT
<213> ORGANISM: Homo sapiens

<400> SEQUENCE: 106

Arg Arg Tyr Tyr Phe Asp Ser Ser Gly Tyr Phe Asp Tyr
1               5                   10

<210> SEQ ID NO 107
<211> LENGTH: 121
<212> TYPE: PRT
<213> ORGANISM: Homo sapiens

<400> SEQUENCE: 107

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile His Tyr Ser Gly Ser Thr Asn Tyr Asn Pro Ser Leu Lys
        50                  55                  60

Ser Arg Val Thr Ile Ser Glu Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Gly Arg Arg Tyr Tyr Asp Ser Ser Gly Tyr Leu Asp Tyr Trp Gly
                100                 105                 110

Gln Gly Thr Leu Val Thr Val Ser Ser
        115                 120

<210> SEQ ID NO 108
<211> LENGTH: 121
<212> TYPE: PRT
<213> ORGANISM: Homo sapiens

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
                20                  25                  30

Tyr Trp Ser Trp Ile Arg Gln Pro Pro Gly Lys Gly Leu Glu Trp Ile
            35                  40                  45

Gly Tyr Ile Tyr Tyr Asn Gly Gly Thr Asn Tyr Lys Pro Ser Leu Lys
        50                  55                  60

```
Ser Arg Val Thr Ile Ser Val Asp Thr Ser Lys Asn Gln Phe Ser Leu
 65                  70                  75                  80

Lys Leu Thr Ser Val Thr Ala Ala Asp Thr Ala Val Tyr Tyr Cys Ala
                 85                  90                  95

Gly Arg Arg Tyr Tyr Tyr Asp Ser Ser Gly Tyr Leu Asp Tyr Trp Gly
            100                 105                 110

Gln Gly Thr Leu Val Thr Val Ser Ser
        115                 120
```

```
<210> SEQ ID NO 109
<211> LENGTH: 10
<212> TYPE: PRT
<213> ORGANISM: Homo sapiens

<400> SEQUENCE: 109

Gly Gly Ser Ile Ser Ser His Tyr Trp Ser
 1               5                  10

<210> SEQ ID NO 110
<211> LENGTH: 16
<212> TYPE: PRT
<213> ORGANISM: Homo sapiens

<400> SEQUENCE: 110

Tyr Ile Tyr Tyr Asn Gly Gly Thr Asn Tyr Lys Pro Ser Leu Lys Ser
 1               5                  10                  15

<210> SEQ ID NO 111
<211> LENGTH: 357
<212> TYPE: DNA
<213> ORGANISM: Homo sapiens

<400> SEQUENCE: 111
gaggtgcagc tgttggagtc tgggggaggc ttggtacagc ctgggggtc cctgagactc     60 tcctgtgcag cctctggatt cacctttagc agctatgcca tgagttgggt ccgccaggct    120
ccagggaagg gctgagtg gtctcaatt attagtggta gtggtggtga cacatactac      180
gcagactccg tgaagggccg gttcaccatc tccagagaca attccaagaa cacgctgtat   240
ctgcagatga acagcctgag agccgaggac acggccgtat attactgtgc gaaaaccgat   300
gaccacggtg acttctttga ctactggggc cagggaaccc tggtcaccgt ctcctca      357

<210> SEQ ID NO 112
<211> LENGTH: 318
<212> TYPE: DNA
<213> ORGANISM: Homo sapiens

<400> SEQUENCE: 112
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attggacgtt cggccaaggg    300
accaaggtgg agatcaaa                                                  318

<210> SEQ ID NO 113
<211> LENGTH: 366
<212> TYPE: DNA
```

<213> ORGANISM: Homo sapiens

<400> SEQUENCE: 113

| caggtgcagc tggtggagtc tgggggaggc gtggtccagc ctggagggtc cctgagactc | 60 |
| tcctgtgcaa cgtctggatt caccttcagt agctatggca tgcactgggt ccgccaggct | 120 |
| ccaggcaagg ggctggagtg ggtggcactt atatggtttg atggaggtaa tcaatactat | 180 |
| gcggactccg tgaagggccg attcaccatc tccagagaca attccaagaa cacgctgtat | 240 |
| ttgcaattga acagtctgag agccgaagac acggctgtgt atttctgtgc gagagatgtg | 300 |
| atcagtatgg ttcggggagt ccctttttgac tactggggcc agggaaccct ggtcaccgtc | 360 |
| tcctca | 366 |

<210> SEQ ID NO 114
<211> LENGTH: 330
<212> TYPE: DNA
<213> ORGANISM: Homo sapiens

<400> SEQUENCE: 114

| gacgctgttg tgactcagga atctgcactc accacatcac ctggtgaaac agtcacactc | 60 |
| acttgtcgct caagtactgg ggctgttaca actggtaact atgccaactg ggtccaagaa | 120 |
| aaaccagatc atttattcac tggtctaata ggtggtatta agaaccgagt tccaggtgtt | 180 |
| cctgccagat tctcaggctc cctgattgga gacaggctg ccctcaccat cacagggca | 240 |
| cagactgagg atgaggcaat atatttctgt gctctatggt acagtaatca ttgggtgttc | 300 |
| ggtggaggaa ccaaactgac tgtcctaggc | 330 |

<210> SEQ ID NO 115
<211> LENGTH: 357
<212> TYPE: DNA
<213> ORGANISM: Homo sapiens

<400> SEQUENCE: 115

| gaggtgcagc tattggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcagtt attagtggta gtggtggtag cacatactac | 180 |
| gcagactccg tgaagggccg gttcaccatc tccagagaca attccaagaa cacgctggat | 240 |
| ctgcaaatga acagcctgag agccgaggac acggccgtat attactgtgc gaaattgggg | 300 |
| gactactact acggtatgga cgtctggggc caagggacca cggtcaccgt ctcctca | 357 |

<210> SEQ ID NO 116
<211> LENGTH: 336
<212> TYPE: DNA
<213> ORGANISM: Homo sapiens

<400> SEQUENCE: 116

| gatattgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgcaga agccagggca gtctccacag ctcctgatct atttggggttc taatcgggcc | 180 |
| tccggggtcc ctgacaggtt cagtggcagt ggatcaggca cagatttac actgaaaatc | 240 |
| agcagagtgg aggctgagga tgttggggtt tattactgca tgcaagctct acaagctccg | 300 |
| tggacgttcg gccaagggac caagctggag atcaaa | 336 |

<210> SEQ ID NO 117
<211> LENGTH: 360
<212> TYPE: DNA
<213> ORGANISM: Homo sapiens

<400> SEQUENCE: 117

```
caggtgcagc tggaggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa tacatactat     180
gcagactccg tgaagggccg attcaccatc tccagagaca attccaagaa cacgctgtat     240
ctgcaaatga acagcctgag agccgaggac acggctgtgt attattgtgc gagagagagg     300 gaaactttt tttatgttat ggatgcctgg ggtcaaggag cttcggtcac cgtctcctca     360
```

<210> SEQ ID NO 118
<211> LENGTH: 318
<212> TYPE: DNA
<213> ORGANISM: Homo sapiens

<400> SEQUENCE: 118

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caatttatta ctgccaacag tttaatcgtt ttatcacctt cggccaaggg     300
acacgactgg agattaaa                                                   318
```

<210> SEQ ID NO 119
<211> LENGTH: 366
<212> TYPE: DNA
<213> ORGANISM: Homo sapiens

<400> SEQUENCE: 119

```
caggtgcagc tggtggagtc tgggggaggc gtggtccagc ctgggaggtc cctgagactc      60
tcctgtgcag cgtctggatt caccttagt aactatggca tgcactgggt ccgccaggct     120
ccaggcaagg ggctggagtg gatggcaggc atatggtttg atggaactaa caaatactat     180
atagactccg tgaagggccg attcaccatt tccagagaca actccaagaa cacgctgtat     240
ctgcaaatga caacctgag agccgaggac acggctgtgt attattgtgc gagagatgta     300
attagtatgg ttcggggagt ccccttttgac tactggggcc agggaaccct ggtcaccgtc     360
tcctca                                                               366
```

<210> SEQ ID NO 120
<211> LENGTH: 342
<212> TYPE: DNA
<213> ORGANISM: Homo sapiens

<400> SEQUENCE: 120

```
gacgctgttg tgactcagga atctgcactc accacatcac ctggtgaaac agtcacactc      60
acttgtcgct caagtactgg ggctgttaca actagtaact atgccaactg ggtccaagaa     120
aaaccagatc atttattcac tggtctaata ggtggtatca caaccgagc tccaggtgtt     180 cctgccagat tctcaggctc cctgattgga gacaaggctg ccctcaccat cacaggggca     240
```

```
cagactgagg atgaggcaat atatttctgt gctctatggt acagcaacca ttgggtgttc    300
ggtggaggaa ccaaactgac tgtcctaggc cagcccaagg ct                       342
```

<210> SEQ ID NO 121
<211> LENGTH: 366
<212> TYPE: DNA
<213> ORGANISM: Homo sapiens

<400> SEQUENCE: 121

```
caggtgcagc tggtggagtc tgggggaggc gtggtccagc ctgggaggtc cctgagactc    60
tcctgtgcag cgtctggatt caccttcagt acctatggca ttcactgggt ccgccaggct   120
ccaggcaagg ggctggagtg ggtggcagtt atatggtttg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatgta   300
attagtatgg ttcggggagt ccccttttgac tactggggcc agggaaccct ggtcaccgtc   360
tcctca                                                              366
```

<210> SEQ ID NO 122
<211> LENGTH: 342
<212> TYPE: DNA
<213> ORGANISM: Homo sapiens

<400> SEQUENCE: 122

```
gacgctgttg tgactcagga atctgcactc accacatcac ctggtgaaac agtcacactc    60
acttgtcgct caagtactgg ggctgttaca actagtaact atgccaactg gtccaagaa   120 aaaccagatc atttattcac tggtctaata ggtggtatca acaaccgagt tccaggtgtt   180
cctgccagat tctcaggctc cctgattgga gacaaggctg ccctcaccat cacagggca   240 cagactgagg atgaggcaat atatttctgt gctctatggt acagcaacca ttgggtgttc   300
ggtggaggaa ccaaggtgac tgtcctaggc cagcccaagg ct                      342
```

<210> SEQ ID NO 123
<211> LENGTH: 366
<212> TYPE: DNA
<213> ORGANISM: Homo sapiens

<400> SEQUENCE: 123

```
caggtgcagc tggtggagtc tgggggaggc gtggtccagc ctgggaggtc cctgagactc    60
tcctgtgcag cgtctggatt caccttcagt aactatggca ttcactgggt ccgccaggct   120
ccaggcaagg ggctggagtg ggtggcagtt atatggtttg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagacgtc   300
attactttgg ttcggggagt ccccttttgac tactggggcc agggaaccct ggtcaccgtc   360
tcctca                                                              366
```

<210> SEQ ID NO 124
<211> LENGTH: 339
<212> TYPE: DNA
<213> ORGANISM: Homo sapiens

<400> SEQUENCE: 124

```
gacgctgttg tgactcagga atctgcactc accacatcac ctggtgaaac agtcacagtc    60
acttgtcgct caagtactgg ggctgttaca actagtaact atgccaattg ggtccaagaa   120
aaaccagatc atttattcac tggtctaata ggtggtatca acaaccgagc tccaggtgtt   180
cctgccagat tctcaggctc cctgattgga gacaaggctg ccctcaccat cacaggggca   240
cagactgagg atgaggcaat atatttctgt gctctctggt acagcaacca ttgggtgttc   300
ggtggaggaa ccaagttgac tgtcctaggc cagcccaag                          339
```

<210> SEQ ID NO 125
<211> LENGTH: 369
<212> TYPE: DNA
<213> ORGANISM: Homo sapiens

<400> SEQUENCE: 125

```
caggtgcaac tgcaggaggc gggcccagga ctggtgaacc cttcgaagac cctgtccctc    60
acctgcactg tctctggtgg ctccatcagt agttacttct ggagctggat ccggcagccc   120
ccaggaaagg gactggagtg gattgggtat atctataaca gtgggagcac caactacaac   180
ccctccctcc agagtcgagt caccatatca gtagacatgt ccaagaacca cttctccctg   240
aagctgagct ctgtgaccgc tgcggacacg gccgtatatt actgtgcgag aaggggggt   300
tactatggtt cggggaatta tggtggtatg gacgtctggg gccaagggac cacggtcacc   360
gtctcctca                                                           369
```

<210> SEQ ID NO 126
<211> LENGTH: 321
<212> TYPE: DNA
<213> ORGANISM: Homo sapiens

<400> SEQUENCE: 126

```
gacatccaga tgacccagtc tccatcctcc ctgtctgcat ctgcaggaga cagagtcacc    60
atcacttgcc gggcgagtca gggcattagc aattatttag cctggtacca gcagaaacca   120
gggaaagttc ctaagctcct gatgtatgct gcatccgctt tgcaatcagg ggtcccatct   180
cggttcagtg gcagtggatc tgggacagat ttcactctca ccatcagcag cctgcagcct   240
gaaagatgtcg caacttatta ctgtcaaaag tatgacagtg ccccgtggac gttcggccaa   300
gggaccaagg tggagatcaa a                                             321
```

<210> SEQ ID NO 127
<211> LENGTH: 363
<212> TYPE: DNA
<213> ORGANISM: Homo sapiens

<400> SEQUENCE: 127

```
caggtgcagc tgcaggagtc gggcccagga ctgctgaagc cttcggagac cctgtccctc    60
acctgcactg tctctggtgg ctccatcagt ccttactact ggagctggat ccggcagccc   120
ccagggaagg gactggagtg gattgggtat atctattaca gtgggaacac caactacaac   180
ccctccctcc agagccgact caccatatca gtagacacgt ccaagaacca gttctccctg   240
aagctgagct ctgtgaccgc tgcggacacg gccgtatatt actgtgcgag acgtggatac   300
agttttggtt tctactacgg tttgacgtc tggggccaag gaccacggt caccgtctcc   360
tca                                                                363
```

<210> SEQ ID NO 128
<211> LENGTH: 321
<212> TYPE: DNA
<213> ORGANISM: Homo sapiens

<400> SEQUENCE: 128

```
gacatccaga tgacccagtc tccatcctcc ctgtctgcat ctgtaggaga cagagtcacc      60
atcacttgcc gggcgagtca ggacattagc atttatttag cctggtatca gcagaaacca     120
gggaaagttc ctaacctcct gatctatctt gcttccactt tgcaatcagg ggtcccatct     180
cggttcagtg gcagtggatc tgggacagat ttcactctca ccatcagcag cctgcagcct     240
gaagatgttg caacttatta ctgtcaaaag tataacagtg ccccgtggac gttcggccaa     300
gggaccaagc tggagatcaa a                                               321
```

<210> SEQ ID NO 129
<211> LENGTH: 363
<212> TYPE: DNA
<213> ORGANISM: Homo sapiens

<400> SEQUENCE: 129

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca gagccgact caccatatca gtagacacgt ccaagaacca gttctccctg     240
aagctgagct ctgtgaccgc tgcggacacg gccgtatatt actgtgcgag acgtggatac     300
agctatggtt actactacgg tatggacgtc tggggccaag gaccacggt caccgtctcc     360
tca                                                                   363
```

<210> SEQ ID NO 130
<211> LENGTH: 321
<212> TYPE: DNA
<213> ORGANISM: Homo sapiens

<400> SEQUENCE: 130

```
gacatccaga tgacccagtc tccatcctcc ctgtctgcat ctgtaggaga cagagtcacc      60
atcacttgcc gggcgagtca ggacattagc aattatttag cctggtatca gcagaaacca     120
gggaaagttc ctaagctcct gatctctcct gcatccactt tgcaatcagg ggtcccatct     180
cggttcagtg gcagtggatc tgggacagat ttcactctca ccatcagcag cctgcagcct     240
gaagatgttg caacttatta ctgtcaaaag tataacagtg ccccgtggac gttcggccaa     300
gggaccaagc tggagatcaa a                                               321
```

<210> SEQ ID NO 131
<211> LENGTH: 369
<212> TYPE: DNA
<213> ORGANISM: Homo sapiens

<400> SEQUENCE: 131

```
caggtgcaac tgcaggagtc gggcccagga ctggtgaacc cttcgaagac cctgtccctc      60
acctgcactg tctctggtgg ctccatcagt aggtacttct ggagctggat ccggcagccc     120
ccagggaagg gactggagtg gattgggtat atctatgaca gtgggagcac caactacaac     180
ccctccctca gagtcgagt caccatatca gtagacacgt ccaagaacca cttctccctg     240
aagctgagct ctgtcaccgc tgcggacacg gccgtgtatt actgtgcgag aaggggggt     300
```

```
tactatggtt cggggagtta tgtggtatg gacgtctggg gccaagggac cacggtcacc    360
gtctcctca                                                          369

<210> SEQ ID NO 132
<211> LENGTH: 321
<212> TYPE: DNA
<213> ORGANISM: Homo sapiens

<400> SEQUENCE: 132
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaaattc ctaagctcct gatctctgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tatgacagtg ccccgtggac gttcggccaa   300
gggaccaagg tggagatcaa a                                             321

<210> SEQ ID NO 133
<211> LENGTH: 363
<212> TYPE: DNA
<213> ORGANISM: Homo sapiens

<400> SEQUENCE: 133
caggtgcagc tgcaggagtc gggcccagga ctggtgaagc cttcggagac cctgtccctc    60
acctgcactg tctctggtgg ctccatcagt agtcactact ggaactggat ccggcagccc   120
ccagggaagg gactggagtg gattgggtac atccattaca gtggggggcac caactacaac   180 ccctcccaaa agagtcgagt caccatatca gtagacacgt ccaagaacca gttctccctg   240
aagctgagct ctgtgaccgc tgcggacacg gccgtgtatt actgtgcggg gaggaggtat   300
tactttgata gtagtggtta tcttgactac tggggccagg gaaccctggt caccgtctcc   360
tca                                                                363

<210> SEQ ID NO 134
<211> LENGTH: 321
<212> TYPE: DNA
<213> ORGANISM: Homo sapiens

<400> SEQUENCE: 134
gacatccaga tgacccagtc tccatcctcc ctgtctgcat ctgtaggaga cagagtcacc    60
atcacttgcc gggcgagtca gggattagc aattatttag cctggtatca gcagaaacca   120
gggaaaattc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg ccccgtggac gttcggccaa   300
gggaccaagc tggagatcaa a                                             321

<210> SEQ ID NO 135
<211> LENGTH: 369
<212> TYPE: DNA
<213> ORGANISM: Homo sapiens

<400> SEQUENCE: 135
caggtgcaac tgcaggagtc gggcccagga ctggtgaacc cttcgaagac cctgtccctc    60
acctgcactg tctctggtgg ctccatcagt agttacttct ggagctggat ccggcagccc   120
```

```
ccagggaagg gactggagtg gattgggtat atctatgaca gtgggagcac caactacaac    180
ccctccctca agagtcgagt caccatatca gtagacacgt ccaagaacca cttctccctg    240
aagctgagct ctgtgaccgc tgcggacacg gccgtgtatt actgtgcgag aagggggggt    300
tactatggtt cggggagtta tggtggtatg gacgtctggg gccaagggac cacggtcacc    360
gtctcctca                                                           369

<210> SEQ ID NO 136
<211> LENGTH: 321
<212> TYPE: DNA
<213> ORGANISM: Homo sapiens

<400> SEQUENCE: 136
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctctgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg ccccgtggac gttcggccaa    300
gggaccaagc tggagatcaa a                                             321

<210> SEQ ID NO 137
<211> LENGTH: 369
<212> TYPE: DNA
<213> ORGANISM: Homo sapiens

<400> SEQUENCE: 137
caggtggagc tgcagcagtc gggcccagga ctggtgaagc cttcggagac cctgtccctc     60
acctgcactg tctctggtgg ctccatcagt acttacttct ggagctggac ccggcagccc    120
ccagggaagg gactggagtg gattgggtat accaactaca gggaaaacac caactacaac    180
ccctccctcg agagtcgagt caccatatca gtagacacgt ccaagaacca gttctccctg    240
aagctgagct ctgtgaccgc tgcggacacg gccgtgtatt actgtgcgag aagggggggt    300
tattatggtt cggggaatta tggtggtatg gacgtctggg gccaagggac cacggtcacc    360
gtctcctca                                                           369

<210> SEQ ID NO 138
<211> LENGTH: 321
<212> TYPE: DNA
<213> ORGANISM: Homo sapiens

<400> SEQUENCE: 138
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaaactcct gatctatgct gcatccactt tgcaatcagg ggtcccatct    180
cgattcagtg gcagtggatc tgggacagat ttcactctca ccatcagcag cctgcagcct    240
gaagatcttg caacttatta ctgtcaaaag tatgacagtg ccccgtggac gttcggccaa    300
gggaccaagc tggagatcaa a                                             321

<210> SEQ ID NO 139
<211> LENGTH: 369
<212> TYPE: DNA
<213> ORGANISM: Homo sapiens
```

```
<400> SEQUENCE: 139
cagttgcaac tgcaggagtc gggcccagga ctggtgaacc cttcgaagac cctgtccctc      60
acctgcaatg tctctggtgg ctccatgagt aattacttct ggagctggat ccggcagccc     120
ccagggaagg gactggagtg gattgggtac atctataatt ctgggaacac caactaccac     180
ccctccctcc agagtcgagt caccatatca gtagacacgt ccaagaacct cttctccctg     240
aagctgacct ctgtgaccgc tgcggacacg gccgtgtatt attgtgcgag aaggggggt      300 tactatggtt cggggaatta tggtggtttg gacgtctggg gccacgggac cacggtcacc     360
gtctcctca                                                             369

<210> SEQ ID NO 140
<211> LENGTH: 321
<212> TYPE: DNA
<213> ORGANISM: Homo sapiens

<400> SEQUENCE: 140
gacatccaga tgacccagtc tccatcctcc ctgtctgcat ctgtaggaga cagagtcacc      60
atcacttgcc gggcgagtca gggcattagc aattatttag cctggtatca gcagaaacca     120
gggaaagttc ctaagctcct gatctatgct gcatccactt tgcaatcagg ggtcccatct     180
cggttcagtg gcactggatc tgggacagat ttcactctca ccatcagcag cctgcagcct     240
gaagatgttg caacttatta ctgtcaaaag tatgacagtg ccccgtggac gttcggccaa     300
gggaccaagg tggagatcaa a                                               321

<210> SEQ ID NO 141
<211> LENGTH: 363
<212> TYPE: DNA
<213> ORGANISM: Homo sapiens

<400> SEQUENCE: 141
caggtgcagc tggtggagtc tgggggaggc gtggtccagc ctgggaggtc cctgagactc      60
tcctgtgcag cgtctggatt caccttcaat aactatggca tgcactgggt ccgccaggct     120
cctggcaagg ggctggagtg ggtggcaatt atatggaatg atggaagtaa tcatactat      180 gcagactccg tgaagggccg attcaccatc tccagagaca attccaagaa cacgctgtat     240
ctgcaaatga acagcctgag agccgaagac acggctgtat attactgtgt gagagatagc     300
agcagctggt tcgtgaacta ctttgactac tggggccagg gaaccctggt caccgtctcc     360
tca                                                                   363

<210> SEQ ID NO 142
<211> LENGTH: 321
<212> TYPE: DNA
<213> ORGANISM: Homo sapiens

<400> SEQUENCE: 142
gaaatagtga tgacgcagtc tccagccacc ctgtctgtgt ctccagggga aagagccacc      60
ctctcctgca gggccagtca gagtgttaat aggaacttag cctggtacca gcagaaacct     120
ggccaggctc ccaggctcct catctatggt gcatccacca gggccactgg tatcccagcc     180
agtttcagtg gcagtgggtc tgggacagag ttcactctca ccatcagcag cctgcagtct     240
gaagattttg cagtttatta ctgtcagcat tataatcact ggccgctcac tttcggcgga     300
gggaccaagg tggagatcaa a                                               321
```

<210> SEQ ID NO 143
<211> LENGTH: 369
<212> TYPE: DNA
<213> ORGANISM: Homo sapiens

<400> SEQUENCE: 143

```
caggtgcagc tacaggagtc gggcccagga ctggtgaagc cttcggagac cctgtccctc     60
acctgcactg tctctggtgg ctccatcagt agttacttct ggagctggat ccggcagccc    120
ccagggaagg gactggagtg gattgggtat atctattaca gtgggagcac caactacaac    180
ccctccctca agagtcgagt caccatatca gtagacacgt ccaagaacca gttctccctg    240
aagctgagtt ctgtgaccgc tgcggacacg gccgtgtatt actgtgcgag aagggggga    300
tacagctatg gttacggcta ctacggtatg gacgtctggg gccaagggac cacggtcacc    360
gtctcctca                                                            369
```

<210> SEQ ID NO 144
<211> LENGTH: 321
<212> TYPE: DNA
<213> ORGANISM: Homo sapiens

<400> SEQUENCE: 144

```
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg ccccgtggac gttcggccaa    300
gggaccaagc tggagatcaa a                                              321
```

<210> SEQ ID NO 145
<211> LENGTH: 369
<212> TYPE: DNA
<213> ORGANISM: Homo sapiens

<400> SEQUENCE: 145

```
cagatacaac tgcaggagtc gggcccagga ctggtgaacc cttcgaagac cctgtccctc     60
acctgcactg tctctggtgg ctccatcaga agttacttct ggagctggat ccggcagccc    120
ccagggaagg gactggagtg gattgggtat atctatgaca gtgggaacac caactacaac    180
ccctccctca agagtcgagt caccatatca gtagacacgt ccaagaacca cttctccctg    240
aagctgagtt ctgtgaccgc tgcggacacg gccgtgtatt actgtgcgag aaggggggt    300
tactatggtt cggggaatta tggtggtatg gacgtctggg gccaagggac cacggtcacc    360
gtctcctca                                                            369
```

<210> SEQ ID NO 146
<211> LENGTH: 363
<212> TYPE: DNA
<213> ORGANISM: Homo sapiens

<400> SEQUENCE: 146

```
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atccattaca gtgggagcac caactacaat    180
ccctccctca agagtcgagt caccatatca gaagacacgt ccaagaacca gttctccctg    240
```
aagctgagct ctgtgaccgc tgcggacacg gccgtgtttt actgtgcggg gaggaggtat    300
tactttgata gtagtggtta ttttgactac tggggccagg gaaccctggt caccgtctcc    360
tca    363

<210> SEQ ID NO 147
<211> LENGTH: 363
<212> TYPE: DNA
<213> ORGANISM: Homo sapiens

<400> SEQUENCE: 147
caggtgcagc tgcaggagtc gggcccagga ctggtgaagc cttcggagac cctgtccctc    60
acctgcactg tctctggtgg ctccatcagt agttactact ggagctggat ccggcagccc    120
ccagggaagg gactggagtg gattgggtat atccattaca gtgggagcac caactacaac    180
ccctccctca agagtcgagt caccatatca gaagacacgt ccaagaacca gttctccctg    240
aagctgagct ctgtgaccgc tgcggacacg gccgtgtttt actgtgcggg gaggaggtat    300
tactatgata gtagtggtta tcttgactac tggggccagg gaaccctggt caccgtctcc    360
tca    363

<210> SEQ ID NO 148
<211> LENGTH: 363
<212> TYPE: DNA
<213> ORGANISM: Homo sapiens

<400> SEQUENCE: 148
caggtgcagc tgcaggagtc gggcccagga ctggtgaagc cttcggagac cctgtccctc    60
acctgcaccg tctctggtgg ctccatcagt agccactact ggagctggat ccggcagccc    120
ccagggaagg gactggagtg gattgggtat atctattaca tgggggcac caactacaaa    180 ccctccctaa agagtcgagt caccatatca gtagacacgt ccaagaacca gttctccctg    240
aagctgacct ctgtgaccgc tgcggacacg gccgtgtatt actgtgcggg gaggaggtat    300
tactatgata gtagtggcta tcttgactat tggggccagg gaaccctggt caccgtctcc    360
tca    363

<210> SEQ ID NO 149
<211> LENGTH: 448
<212> TYPE: PRT
<213> ORGANISM: Homo sapiens

<400> SEQUENCE: 149

Met Ile Pro Thr Phe Thr Ala Leu Leu Cys Leu Gly Leu Ser Leu Gly
1               5                   10                  15

Pro Arg Thr Asp Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

```
Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Gly Pro
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
        355                 360                 365

Arg Arg Glu Met Ala Ser Pro Pro Ser Pro Leu Ser Gly Glu Phe Leu
    370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Arg Leu His
                405                 410                 415

Ser Phe Thr Leu Arg Gln Lys Ala Thr Glu Pro Pro Pro Ser Gln Glu
            420                 425                 430

Gly Ala Ser Pro Ala Glu Pro Ser Val Tyr Ala Thr Leu Ala Ile His
        435                 440                 445

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
atagctcttc agggaccatg aarcayctgt ggttcttcct                     40

<210> SEQ ID NO 151
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
atagctcttc agggaccatg gacatacttt gttccacgc                              39

<210> SEQ ID NO 152
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
atagctcttc agggaccatg gacacacttt gctacacac                              39

<210> SEQ ID NO 153
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
atagctcttc agggaccatg tctgtctcct tcctcatct                              39

<210> SEQ ID NO 154
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
atagctcttc agggaccatg gactggacct ggagvatc                               38

<210> SEQ ID NO 155
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
atagctcttc agggaccatg gactggattt ggaggrtc                               38

<210> SEQ ID NO 156
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
atagctcttc agggaccatg gactgcacct ggaggatc                               38

<210> SEQ ID NO 157
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
atagctcttc agggaccatg gactggacct ggaggktc                           38

<210> SEQ ID NO 158
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
atagctcttc agggaccatg gagttkggrc tgagctgg                           38

<210> SEQ ID NO 159
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
atagctcttc agggaccatg gagtttkggc tkagctgg                           38

<210> SEQ ID NO 160
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
atagctcttc agggaccatg gaactggggc tccgctgg                           38

<210> SEQ ID NO 161
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
atagctcttc agggaccatg garttggggc tgwgctgg                           38

<210> SEQ ID NO 162
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
atagctcttc agggaccatg gggtcaaccg ccatcctc                           38

<210> SEQ ID NO 163
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 163
atagctcttc agggaccatg gacatgaggg tsccygctca gctc                  44

<210> SEQ ID NO 164
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
atagctcttc agggaccatg gacatgagrg tcctcgctca gctc                  44

<210> SEQ ID NO 165
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
atagctcttc agggaccatg gaagccccag cdcagcttct c                     41

<210> SEQ ID NO 166
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
atagctcttc agggaccatg gaaaccccag cgcagcttct c                     41

<210> SEQ ID NO 167
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
atagctcttc agggaccatg gtgttgcaga cccaggtctt c                     41

<210> SEQ ID NO 168
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
atagctcttc agggaccatg gggtcccagg ttcacctcct c                     41

<210> SEQ ID NO 169
<211> LENGTH: 41
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 169
atagctcttc agggaccatg aggctccytg ctcagctcct g                               41

<210> SEQ ID NO 170
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
atagctcttc ttcgtttgat ctccascttg gtc                                       33

<210> SEQ ID NO 171
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
atagctcttc ttcgtttaat ctccagtcgt gtc                                       33

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
atagctcttc tggctgagga gacggtgacc                                           30

<210> SEQ ID NO 173
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
atagctcttc atgtgacgct gttgtgactc agga                                      34

<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
atagctcttc atgtgaccyt gtgctcactc agtc                                      34

<210> SEQ ID NO 175
<211> LENGTH: 37
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 175
gatgctcttc tgggctggcc taggacagtc amcytgg                              37
```

ANTI-ILT3 ANTIBODIES AND ANTIBODY DRUG CONJUGATES

RELATED APPLICATIONS

The instant applicant is a continuation of U.S. patent application Ser. No. 16/484,238, filed Aug. 7, 2019, which is a 35 U.S.C. § 371 national stage filing of International Application No. PCT/US2018/017546, filed on Feb. 9, 2018, which in turn claims priority to U.S. Provisional Application No. 62/457,021, filed on Feb. 9, 2017, the entire contents of each of which are expressly incorporated by reference herein in their entirety.

SEQUENCE LISTING

The instant application contains a Sequence Listing which has been submitted electronically in ASCII format and is hereby incorporated by reference in its entirety. Said ASCII copy, created on Jan. 26, 2022, is named 127913-00203_SL.txt and is 83,90183,789 bytes in size.

BACKGROUND

ILT3, also known as "immunoglobulin-like transcript 3," "Leukocyte immunoglobulin-like receptor subfamily B member 4," "LILRB4," "LIR5," and "CD85k," is a member of the leukocyte immunoglublin-like receptor (LIR) family. "LIRs" are a family of immunoreceptors expressed predominantly on monocytes and B cells and at lower levels on dendritic cells and natural killer ("NK") cells. ILT3 was originally cloned in 1997 (Arm et al., *J. Immun.* 159:2342-2349, 1997; Cella et al., *J. Exp. Med.* 185:1743-1751, 1997; and Borges et al., *J. Immun.* 159:5192-5196, 1997) and is expressed on myeloid antigen presenting cells (APCs) such as monocytes, macrophages, and dendritic cells (DC) (Cella et al., *J. Exp. Med.* 185:1743-1751, 1997). CD68$^+$ myeloid cells and myeolid derived suppressor cells (MDSC) infiltrating solid tumors have also been shown to express ILT3 (Suciu-Foca, N. et al., *J. Immunol.*, 2007, 178, 7432-7441 and De Goeje, et al., Oncoimmunology. 2015 July; 4(7)).

The cytoplasmic region of ILT3 contains putative immunoreceptor tyrosine-based inhibitory motifs (ITIMs), that indicate an inhibitory role of ILT3. Co-ligation of ILT3 to stimulatory receptors expressed by APCs results in an inhibition of the increased [Ca2+] flux and tyrosine phosphorylation triggered by these receptors. Signal extinction involves SH2-containing protein tyrosine phosphatase 1, which is recruited by ILT3 upon cross-linking. ILT3 can also function in antigen capture and presentation. It is internalized upon cross-linking and delivers its ligand to an intracellular compartment where it is processed and presented to T cells. Thus, ILT3 is an inhibitory receptor involved in the down-regulation of the immune response that can negatively regulate activation of APCs and can be used by APCs for antigen uptake (Cella, et al. (1997) J. Exp. Med. 185:1743-1751).

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-ILT3 antibodies and ADCs that can be used for therapeutic purposes in the treatment of cancer.

SUMMARY

In certain aspects, the present invention provides for anti-ILT3 antibodies and antibody drug conjugates (ADCs). In certain embodiments of the invention, the antibodies, or antigen binding portions thereof, bind to ILT3 (SEQ ID NO: 149) or the extracellular domain of ILT3. In one embodiment, the antibodies, or antigen binding portions thereof, of the invention, bind to ILT3 with a $K_d$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In yet other embodiments of the invention, anti-ILT3 antibody drug conjugates (ADCs) of the invention (e.g., the ILT3 antibodies of the invention conjugated to a toxin) capable of being internalized. In another embodiment, the anti-ILT3 antibody drug conjugates (ADCs) of the invention are capable of inducing cell death of cells endogenously expressing ILT3.

In some embodiments, the antibodies, or antigen binding portions thereof, comprise a heavy chain variable region comprising a CDR3 having the amino acid sequence of SEQ ID NO: 4 and a light chain variable region comprising a CDR3 having the amino acid sequence of SEQ ID NO: 8. In some embodiments, the antibodies, or antigen binding portions thereof, further comprise a heavy chain variable region comprising a CDR2 having the amino acid sequence of SEQ ID NO: 3 and a light chain variable region comprising a CDR2 having the amino acid sequence of SEQ ID NO: 7. In some embodiments, the antibodies, or antigen binding portions thereof, further comprise a heavy chain variable region comprising a CDR1 having the amino acid sequence of SEQ ID NO: 2 and a light chain variable region comprising a CDR1 having the amino acid sequence of either SEQ ID NO: 6.

In some embodiments, the antibodies, or antigen binding portions thereof, comprise a heavy chain variable region comprising a CDR3 having the amino acid sequence of SEQ ID NO: 12 and a light chain variable region comprising a CDR3 having the amino acid sequence of SEQ ID NO: 16. In some embodiments, the antibodies, or antigen binding portions thereof, further comprise a heavy chain variable region comprising a CDR2 having the amino acid sequence of SEQ ID NO: 11 and a light chain variable region comprising a CDR2 having the amino acid sequence of SEQ ID NO: 15. In some embodiments, the antibodies, or antigen binding portions thereof, further comprise a heavy chain variable region comprising a CDR1 having the amino acid sequence of SEQ ID NO: 10 and a light chain variable region comprising a CDR1 having the amino acid sequence of either SEQ ID NO: 14.

In some embodiments, the antibodies, or antigen binding portions thereof, comprise a heavy chain variable region comprising a CDR3 having the amino acid sequence of SEQ ID NO: 19 and a light chain variable region comprising a CDR3 having the amino acid sequence of SEQ ID NO: 23. In some embodiments, the antibodies, or antigen binding portions thereof, further comprise a heavy chain variable region comprising a CDR2 having the amino acid sequence of SEQ ID NO: 18 and a light chain variable region comprising a CDR2 having the amino acid sequence of SEQ ID NO: 22. In some embodiments, the antibodies, or antigen binding portions thereof, further comprise a heavy chain variable region comprising a CDR1 having the amino acid sequence of SEQ ID NO: 2 and a light chain variable region comprising a CDR1 having the amino acid sequence of either SEQ ID NO: 21.

In some embodiments, the antibodies, or antigen binding portions thereof, comprise a heavy chain variable region comprising a CDR3 having the amino acid sequence of SEQ ID NO: 26 and a light chain variable region comprising a CDR3 having the amino acid sequence of SEQ ID NO: 28. In some embodiments, the antibodies, or antigen binding portions thereof, further comprise a heavy chain variable region comprising a CDR2 having the amino acid sequence of SEQ ID NO: 25 and a light chain variable region comprising a CDR2 having the amino acid sequence of SEQ ID NO: 7. In some embodiments, the antibodies, or antigen binding portions thereof, further comprise a heavy chain variable region comprising a CDR1 having the amino acid sequence of SEQ ID NO: 10 and a light chain variable region comprising a CDR1 having the amino acid sequence of either SEQ ID NO: 6.

In some embodiments, the antibodies, or antigen binding portions thereof, comprise a heavy chain variable region comprising a CDR3 having the amino acid sequence of SEQ ID NO: 12 and a light chain variable region comprising a CDR3 having the amino acid sequence of SEQ ID NO: 16. In some embodiments, the antibodies, or antigen binding portions thereof, further comprise a heavy chain variable region comprising a CDR2 having the amino acid sequence of SEQ ID NO: 31 and a light chain variable region comprising a CDR2 having the amino acid sequence of SEQ ID NO: 34. In some embodiments, the antibodies, or antigen binding portions thereof, further comprise a heavy chain variable region comprising a CDR1 having the amino acid sequence of SEQ ID NO: 30 and a light chain variable region comprising a CDR1 having the amino acid sequence of either SEQ ID NO: 33.

In some embodiments, the antibodies, or antigen binding portions thereof, comprise a heavy chain variable region comprising a CDR3 having the amino acid sequence of SEQ ID NO: 12 and a light chain variable region comprising a CDR3 having the amino acid sequence of SEQ ID NO: 16. In some embodiments, the antibodies, or antigen binding portions thereof, further comprise a heavy chain variable region comprising a CDR2 having the amino acid sequence of SEQ ID NO: 37 and a light chain variable region comprising a CDR2 having the amino acid sequence of SEQ ID NO: 39. In some embodiments, the antibodies, or antigen binding portions thereof, further comprise a heavy chain variable region comprising a CDR1 having the amino acid sequence of SEQ ID NO: 36 and a light chain variable region comprising a CDR1 having the amino acid sequence of either SEQ ID NO: 33.

In some embodiments, the antibodies, or antigen binding portions thereof, comprise a heavy chain variable region comprising a CDR3 having the amino acid sequence of SEQ ID NO: 43 and a light chain variable region comprising a CDR3 having the amino acid sequence of SEQ ID NO: 16. In some embodiments, the antibodies, or antigen binding portions thereof, further comprise a heavy chain variable region comprising a CDR2 having the amino acid sequence of SEQ ID NO: 42 and a light chain variable region comprising a CDR2 having the amino acid sequence of SEQ ID NO: 34. In some embodiments, the antibodies, or antigen binding portions thereof, further comprise a heavy chain variable region comprising a CDR1 having the amino acid sequence of SEQ ID NO: 41 and a light chain variable region comprising a CDR1 having the amino acid sequence of either SEQ ID NO: 33.

In some embodiments, the antibodies, or antigen binding portions thereof, comprise a heavy chain variable region comprising a CDR3 having the amino acid sequence of SEQ ID NO: 48 and a light chain variable region comprising a CDR3 having the amino acid sequence of SEQ ID NO: 52. In some embodiments, the antibodies, or antigen binding portions thereof, further comprise a heavy chain variable region comprising a CDR2 having the amino acid sequence of SEQ ID NO: 47 and a light chain variable region comprising a CDR2 having the amino acid sequence of SEQ ID NO: 51. In some embodiments, the antibodies, or antigen binding portions thereof, further comprise a heavy chain variable region comprising a CDR1 having the amino acid sequence of SEQ ID NO: 46 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 56 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 55 and a light chain variable region comprising a CDR2 having the amino acid sequence of SEQ ID NO: 59. In some embodiments, the antibodies, or antigen binding portions thereof, further comprise a heavy chain variable region comprising a CDR1 having the amino acid sequence of SEQ ID NO: 54 and a light chain variable region comprising a CDR1 having the amino acid sequence of either SEQ ID NO: 58.

In some embodiments, the antibodies, or antigen binding portions thereof, comprise a heavy chain variable region comprising a CDR3 having the amino acid sequence of SEQ ID NO: 64 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 63 and a light chain variable region comprising a CDR2 having the amino acid sequence of SEQ ID NO: 67. In some embodiments, the antibodies, or antigen binding portions thereof, further comprise a heavy chain variable region comprising a CDR1 having the amino acid sequence of SEQ ID NO: 62 and a light chain variable region comprising a CDR1 having the amino acid sequence of either SEQ ID NO: 66.

In some embodiments, the antibodies, or antigen binding portions thereof, comprise a heavy chain variable region comprising a CDR3 having the amino acid sequence of SEQ ID NO: 71 and a light chain variable region comprising a CDR3 having the amino acid sequence of SEQ ID NO: 52. In some embodiments, the antibodies, or antigen binding portions thereof, further comprise a heavy chain variable region comprising a CDR2 having the amino acid sequence of SEQ ID NO: 70 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 69 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 77 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 76 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 75 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 71 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 70 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 46 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 48 and a light chain variable region comprising a CDR3 having the amino acid sequence of SEQ ID NO: 52. In some embodiments, the antibodies, or antigen binding portions thereof, further comprise a heavy chain variable region comprising a CDR2 having the amino acid sequence of SEQ ID NO: 83 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 82 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 88 and a light chain variable region comprising a CDR3 having the amino acid sequence of SEQ ID NO: 52. In some embodiments, the antibodies, or antigen binding portions thereof, further comprise a heavy chain variable region comprising a CDR2 having the amino acid sequence of SEQ ID NO: 87 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 86 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 93 and a light chain variable region comprising a CDR3 having the amino acid sequence of SEQ ID NO: 97. In some embodiments, the antibodies, or antigen binding portions thereof, further comprise a heavy chain variable region comprising a CDR2 having the amino acid sequence of SEQ ID NO: 92 and a light chain variable region comprising a CDR2 having the amino acid sequence of SEQ ID NO: 96. In some embodiments, the antibodies, or antigen binding portions thereof, further comprise a heavy chain variable region comprising a CDR1 having the amino acid sequence of SEQ ID NO: 91 and a light chain variable region comprising a CDR1 having the amino acid sequence of either SEQ ID NO: 95.

In some embodiments, the antibodies, or antigen binding portions thereof, comprise a heavy chain variable region comprising a CDR3 having the amino acid sequence of SEQ ID NO: 99 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 63 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 46 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 48 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 103 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 102 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 106 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 105 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 62 and a light chain variable region comprising a CDR1 having the amino acid sequence of either SEQ ID NO: 50.

In some embodiments, the antibodies, or antigen binding portions thereof, comprise a heavy chain variable region comprising a CDR3 having the amino acid sequence of SEQ ID NO: 106 and a light chain variable region comprising a CDR3 having the amino acid sequence of SEQ ID NO: 60. In some embodiments, the antibodies, or antigen binding portions thereof, further comprise a heavy chain variable region comprising a CDR2 having the amino acid sequence of SEQ ID NO: 110 and a light chain variable region comprising a CDR2 having the amino acid sequence of SEQ ID NO: 73. In some embodiments, the antibodies, or antigen binding portions thereof, further comprise a heavy chain variable region comprising a CDR1 having the amino acid sequence of SEQ ID NO: 109 and a light chain variable region comprising a CDR1 having the amino acid sequence of either SEQ ID NO: 50.

In one embodiment, the antibody, or antigen binding portion thereof is an IgG isotype. In another embodiment, the antibody, or antigen binding portion thereof, has a $K_D$ of about 2,000 nM or less.

In some embodiments, the antibodies, or antigen binding portions thereof, comprise a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In some embodiments, the antibodies, or antigen binding portions thereof, comprise a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In some embodiments, the antibodies, or antigen binding portions thereof, comprise a heavy chain variable region comprising a CDR3 domain comprising the amino acid sequence of SEQ ID NO: 19, a CDR2 domain comprising the amino acid sequence of SEQ ID NO: 18, and a CDR1 domain comprising the amino acid sequence of SEQ ID NO: 2, and a light chain variable region comprising a CDR3 domain comprising the amino acid sequence of SEQ ID NO: 23, a CDR2 domain comprising the amino acid sequence of SEQ ID NO: 22, and a CDR1 domain comprising the amino acid sequence of SEQ ID NO: 21.

In some embodiments, the antibodies, or antigen binding portions thereof, comprise a heavy chain variable region comprising a CDR3 domain comprising the amino acid sequence of SEQ ID NO: 26, a CDR2 domain comprising the amino acid sequence of SEQ ID NO: 25, and a CDR1 domain comprising the amino acid sequence of SEQ ID NO: 10, and a light chain variable region comprising a CDR3 domain comprising the amino acid sequence of SEQ ID NO: 28, a CDR2 domain comprising the amino acid sequence of SEQ ID NO: 7, and a CDR1 domain comprising the amino acid sequence of SEQ ID NO: 6.

In some embodiments, the antibodies, or antigen binding portions thereof, comprise a heavy chain variable region comprising a CDR3 domain comprising the amino acid sequence of SEQ ID NO: 12, a CDR2 domain comprising the amino acid sequence of SEQ ID NO: 31, and a CDR1 domain comprising the amino acid sequence of SEQ ID NO: 30, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33.

In some embodiments, the antibodies, or antigen binding portions thereof, comprise a heavy chain variable region comprising a CDR3 domain comprising the amino acid sequence of SEQ ID NO: 12, a CDR2 domain comprising the amino acid sequence of SEQ ID NO: 37, and a CDR1 domain comprising the amino acid sequence of SEQ ID NO: 36, and a light chain variable region comprising a CDR3 domain comprising the amino acid sequence of SEQ ID NO: 16, a CDR2 domain comprising the amino acid sequence of SEQ ID NO: 39, and a CDR1 domain comprising the amino acid sequence of SEQ ID NO: 33.

In some embodiments, the antibodies, or antigen binding portions thereof, comprise a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33.

In some embodiments, the antibodies, or antigen binding portions thereof, comprise a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54, and a light chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58.

In some embodiments, the antibodies, or antigen binding portions thereof, comprise a heavy chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 67, and a CDR1 domain comprising the amino acid sequence of SEQ ID NO: 66.

In some embodiments, the antibodies, or antigen binding portions thereof, comprise a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 69, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 48, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 97, a CDR2 domain comprising the amino acid sequence of SEQ ID NO: 96, and a CDR1 domain comprising the amino acid sequence of SEQ ID NO: 95.

In some embodiments, the antibodies, or antigen binding portions thereof, comprise a heavy chain variable region comprising a CDR3 domain comprising the amino acid sequence of SEQ ID NO: 99, a CDR2 domain comprising the amino acid sequence of SEQ ID NO: 63, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 48, a CDR2 domain comprising the amino acid sequence of SEQ ID NO: 103, and a CDR1 domain comprising the amino acid sequence of SEQ ID NO: 102, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable region comprising a CDR3 domain comprising the amino acid sequence of SEQ ID NO: 106, a CDR2 domain comprising the amino acid sequence of SEQ ID NO: 110, and a CDR1 domain comprising the amino acid sequence of SEQ ID NO: 109, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In some embodiments, the antibodies, or antigen binding portions thereof, comprise a heavy chain variable domain comprising an amino acid sequence set forth in SEQ ID NO: 1 and a light chain variable domain comprising an amino acid sequence set forth in SEQ ID NO: 5.

In some embodiments, the antibodies, or antigen binding portions thereof, comprise a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In some embodiments, the antibodies, or antigen binding portions thereof, comprise a heavy chain variable region comprising the amino acid sequence of SEQ ID NO: 9 and a light chain variable region comprising the amino acid sequence of SEQ ID NO: 13.

In some embodiments, the antibodies, or antigen binding portions thereof, comprise a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In some embodiments, the antibodies, or antigen binding portions thereof, comprise a heavy chain variable region comprising the amino acid sequence of SEQ ID NO: 17 and a light chain variable region comprising the amino acid sequence of SEQ ID NO: 20.

In some embodiments, the antibodies, or antigen binding portions thereof, comprise a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In some embodiments, the antibodies, or antigen binding portions thereof, comprise a heavy chain variable region comprising the amino acid sequence of SEQ ID NO: 24 and a light chain variable region comprising the amino acid sequence of SEQ ID NO: 27.

In some embodiments, the antibodies, or antigen binding portions thereof, comprise a heavy chain comprising an amino acid sequence set forth in SEQ ID NO: 24, or a sequence having at least 90%, 95%, 96%, 97%, 98%, or 99% identity to SEQ ID NO: 24, and/or a light chain comprising an amino acid sequence set forth in SEQ ID NO: 27, or a sequence having at least 90%, 95%, 96%, 97%, 98%, or 99% identity to SEQ ID NO: 27.

In some embodiments, the antibodies, or antigen binding portions thereof, comprise a heavy chain variable region comprising the amino acid sequence of SEQ ID NO: 29 and a light chain variable region comprising the amino acid sequence of SEQ ID NO: 32.

In some embodiments, the antibodies, or antigen binding portions thereof, comprise a heavy chain comprising an amino acid sequence set forth in SEQ ID NO: 29, or a sequence having at least 90%, 95%, 96%, 97%, 98%, or 99% identity to SEQ ID NO: 29, and/or a light chain comprising an amino acid sequence set forth in SEQ ID NO: 32, or a sequence having at least 90%, 95%, 96%, 97%, 98%, or 99% identity to SEQ ID NO: 32.

In some embodiments, the antibodies, or antigen binding portions thereof, comprise a heavy chain variable region comprising the amino acid sequence of SEQ ID NO: 35 and a light chain variable region comprising the amino acid sequence of SEQ ID NO: 38.

In some embodiments, the antibodies, or antigen binding portions thereof, comprise a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 38, or a sequence having at least 90%, 95%, 96%, 97%, 98%, or 99% identity to SEQ ID NO: 38.

In some embodiments, the antibodies, or antigen binding portions thereof, comprise a heavy chain variable region comprising the amino acid sequence of SEQ ID NO: 40 and a light chain variable region comprising the amino acid sequence of SEQ ID NO: 44.

In some embodiments, the antibodies, or antigen binding portions thereof, comprise a heavy chain comprising an amino acid sequence set forth in SEQ ID NO: 40, or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In some embodiments, the antibodies, or antigen binding portions thereof, comprise a heavy chain variable region comprising the amino acid sequence of SEQ ID NO: 45 and a light chain variable region comprising the amino acid sequence of SEQ ID NO: 49.

In some embodiments, the antibodies, or antigen binding portions thereof, comprise a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In some embodiments, the antibodies, or antigen binding portions thereof, comprise a heavy chain variable region comprising the amino acid sequence of SEQ ID NO: 53 and a light chain variable region comprising the amino acid sequence of SEQ ID NO: 57.

In some embodiments, the antibodies, or antigen binding portions thereof, comprise a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 57, or a sequence having at least 90%, 95%, 96%, 97%, 98%, or 99% identity to SEQ ID NO: 57.

In some embodiments, the antibodies, or antigen binding portions thereof, comprise a heavy chain variable region comprising the amino acid sequence of SEQ ID NO: 61 and a light chain variable region comprising the amino acid sequence of SEQ ID NO: 65.

In some embodiments, the antibodies, or antigen binding portions thereof, comprise a heavy chain comprising an amino acid sequence set forth in SEQ ID NO: 61, or a sequence having at least 90%, 95%, 96%, 97%, 98%, or 99% identity to SEQ ID NO: 61, and/or a light chain comprising an amino acid sequence set forth in SEQ ID NO: 65, or a sequence having at least 90%, 95%, 96%, 97%, 98%, or 99% identity to SEQ ID NO: 65.

In some embodiments, the antibodies, or antigen binding portions thereof, comprise a heavy chain variable region comprising the amino acid sequence of SEQ ID NO: 68 and a light chain variable region comprising the amino acid sequence of SEQ ID NO: 72.

In some embodiments, the antibodies, or antigen binding portions thereof, comprise a heavy chain comprising an amino acid sequence set forth in SEQ ID NO: 68, or a sequence having at least 90%, 95%, 96%, 97%, 98%, or 99% identity to SEQ ID NO: 68, and/or a light chain comprising an amino acid sequence set forth in SEQ ID NO: 72, or a sequence having at least 90%, 95%, 96%, 97%, 98%, or 99% identity to SEQ ID NO: 72.

In some embodiments, the antibodies, or antigen binding portions thereof, comprise a heavy chain variable region comprising the amino acid sequence of SEQ ID NO: 74 and a light chain variable region comprising the amino acid sequence of SEQ ID NO: 78.

In some embodiments, the antibodies, or antigen binding portions thereof, comprise a heavy chain comprising an amino acid sequence set forth in SEQ ID NO: 74, or a sequence having at least 90%, 95%, 96%, 97%, 98%, or 99% identity to SEQ ID NO: 74, and/or a light chain comprising an amino acid sequence set forth in SEQ ID NO:

78, or a sequence having at least 90%, 95%, 96%, 97%, 98%, or 99% identity to SEQ ID NO: 78.

In some embodiments, the antibodies, or antigen binding portions thereof, comprise a heavy chain variable region comprising the amino acid sequence of SEQ ID NO: 79 and a light chain variable region comprising the amino acid sequence of SEQ ID NO: 80.

In some embodiments, the antibodies, or antigen binding portions thereof, comprise a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 80, or a sequence having at least 90%, 95%, 96%, 97%, 98%, or 99% identity to SEQ ID NO: 80.

In some embodiments, the antibodies, or antigen binding portions thereof, comprise a heavy chain variable region comprising the amino acid sequence of SEQ ID NO: 81 and a light chain variable region comprising the amino acid sequence of SEQ ID NO: 84.

In some embodiments, the antibodies, or antigen binding portions thereof, comprise a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 84, or a sequence having at least 90%, 95%, 96%, 97%, 98%, or 99% identity to SEQ ID NO: 84.

In some embodiments, the antibodies, or antigen binding portions thereof, comprise a heavy chain variable region comprising the amino acid sequence of SEQ ID NO: 85 and a light chain variable region comprising the amino acid sequence of SEQ ID NO: 89.

In some embodiments, the antibodies, or antigen binding portions thereof, comprise a heavy chain comprising an amino acid sequence set forth in SEQ ID NO: 85, or a sequence having at least 90%, 95%, 96%, 97%, 98%, or 99% identity to SEQ ID NO: 85, and/or a light chain comprising an amino acid sequence set forth in SEQ ID NO: 89, or a sequence having at least 90%, 95%, 96%, 97%, 98%, or 99% identity to SEQ ID NO: 89.

In some embodiments, the antibodies, or antigen binding portions thereof, comprise a heavy chain variable region comprising the amino acid sequence of SEQ ID NO: 90 and a light chain variable region comprising the amino acid sequence of SEQ ID NO: 94.

In some embodiments, the antibodies, or antigen binding portions thereof, comprise a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 94, or a sequence having at least 90%, 95%, 96%, 97%, 98%, or 99% identity to SEQ ID NO: 94.

In some embodiments, the antibodies, or antigen binding portions thereof, comprise a heavy chain variable region comprising the amino acid sequence of SEQ ID NO: 98 and a light chain variable region comprising the amino acid sequence of SEQ ID NO: 100.

In some embodiments, the antibodies, or antigen binding portions thereof, comprise a heavy chain comprising an amino acid sequence set forth in SEQ ID NO: 98, or a sequence having at least 90%, 95%, 96%, 97%, 98%, or 99% identity to SEQ ID NO: 98, and/or a light chain comprising an amino acid sequence set forth in SEQ ID NO: 100, or a sequence having at least 90%, 95%, 96%, 97%, 98%, or 99% identity to SEQ ID NO: 100.

In some embodiments, the antibodies, or antigen binding portions thereof, comprise a heavy chain variable region comprising the amino acid sequence of SEQ ID NO: 101 and a light chain variable region comprising the amino acid sequence of SEQ ID NO: 100.

In some embodiments, the antibodies, or antigen binding portions thereof, comprise a heavy chain comprising an amino acid sequence set forth in SEQ ID NO: 101, or a sequence having at least 90%, 95%, 96%, 97%, 98%, or 99% identity to SEQ ID NO: 101, and/or a light chain comprising an amino acid sequence set forth in SEQ ID NO: 100, or a sequence having at least 90%, 95%, 96%, 97%, 98%, or 99% identity to SEQ ID NO: 100.

In some embodiments, the antibodies, or antigen binding portions thereof, comprise a heavy chain variable region comprising the amino acid sequence of SEQ ID NO: 104 and a light chain variable region comprising the amino acid sequence of SEQ ID NO: 100.

In some embodiments, the antibodies, or antigen binding portions thereof, comprise a heavy chain comprising an amino acid sequence set forth in SEQ ID NO: 104, or a sequence having at least 90%, 95%, 96%, 97%, 98%, or 99% identity to SEQ ID NO: 104, and/or a light chain comprising an amino acid sequence set forth in SEQ ID NO: 100, or a sequence having at least 90%, 95%, 96%, 97%, 98%, or 99% identity to SEQ ID NO: 100.

In some embodiments, the antibodies, or antigen binding portions thereof, comprise a heavy chain variable region comprising the amino acid sequence of SEQ ID NO: 107 and a light chain variable region comprising the amino acid sequence of SEQ ID NO: 100.

In some embodiments, the antibodies, or antigen binding portions thereof, comprise a heavy chain comprising an amino acid sequence set forth in SEQ ID NO: 107, or a sequence having at least 90%, 95%, 96%, 97%, 98%, or 99% identity to SEQ ID NO: 107, and/or a light chain comprising an amino acid sequence set forth in SEQ ID NO: 100, or a sequence having at least 90%, 95%, 96%, 97%, 98%, or 99% identity to SEQ ID NO: 100.

In some embodiments, the antibodies, or antigen binding portions thereof, comprise a heavy chain variable region comprising the amino acid sequence of SEQ ID NO: 108 and a light chain variable region comprising the amino acid sequence of SEQ ID NO: 100.

In some embodiments, the antibodies, or antigen binding portions thereof, comprise a heavy chain comprising an amino acid sequence set forth in SEQ ID NO: 108, or a sequence having at least 90%, 95%, 96%, 97%, 98%, or 99% identity to SEQ ID NO: 108, and/or a light chain comprising an amino acid sequence set forth in SEQ ID NO: 100, or a sequence having at least 90%, 95%, 96%, 97%, 98%, or 99% identity to SEQ ID NO: 100.

In other embodiments, the antibodies, or antigen binding portions thereof binds to the same epitope as an antibody, or antigen-binding portion thereof described herein.

The invention also provides, in certain embodiments, isolated nucleic acids encoding the antibodies, or antigen binding portions thereof of the invention.

In some embodiments of the invention, the antibodies, or antigen binding portions thereof, comprise a heavy chain immunoglobulin constant domain selected from the group consisting of a human IgG constant domain, a human IgM constant domain, a human IgE constant domain, and a human IgA constant domain. In some embodiments, the IgG constant domain is selected from the group consisting of an IgG1 constant domain, an IgG2 constant domain, an IgG3 constant domain, and an IgG4 constant domain. In other embodiments, the antibody is a multispecific antibody. In one embodiment, the antibody is a bispecific antibody.

In other embodiments of the invention, the antibodies, or antigen binding portions thereof, comprise a Fab, a Fab', a F(ab')2, a Fv, a disulfide linked Fv, an scFv, a single domain antibody, and a diabody.

In other embodiments the invention provides a pharmaceutical composition comprising the antibody, or antigen binding portion thereof, as described herein, and a pharmaceutically acceptable carrier.

In other embodiments the invention provides an antibody, or antigen binding portion thereof, as described herein, conjugated to at least one drug. In some embodiments, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In one embodiment, the drug is a pyrrolobenzodiazepine (PBD).

In some embodiments, the at least one drug is conjugated to the antibody, or antigen-binding portion thereof, via a linker, e.g., a cleavable linker or a non-cleavable linker.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 19, a CDR2 domain comprising the amino acid sequence of SEQ ID NO: 18, and a CDR1 domain comprising the amino acid sequence of SEQ ID NO: 2, and a light chain variable region comprising a CDR3 domain comprising the amino acid sequence of SEQ ID NO: 23, a CDR2 domain comprising the amino acid sequence of SEQ ID NO: 22, and a CDR1 domain comprising the amino acid sequence of SEQ ID NO: 21.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 26, a CDR2 domain comprising the amino acid sequence of SEQ ID NO: 25, and a CDR1 domain comprising the amino acid sequence of SEQ ID NO: 10, and a light chain variable region comprising a CDR3 domain comprising the amino acid sequence of SEQ ID NO: 28, a CDR2 domain comprising the amino acid sequence of SEQ ID NO: 7, and a CDR1 domain comprising the amino acid sequence of SEQ ID NO: 6.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 31, and a CDR1 domain comprising the amino acid sequence of SEQ ID NO: 30, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 37, and a CDR1 domain comprising the amino acid sequence of SEQ ID NO: 36, and a light chain variable region comprising a CDR3 domain comprising the amino acid sequence of SEQ ID NO: 16, a CDR2 domain comprising the amino acid sequence of SEQ ID NO: 39, and a CDR1 domain comprising the amino acid sequence of SEQ ID NO: 33.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54, and a light chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 67, and a CDR1 domain comprising the amino acid sequence of SEQ ID NO: 66.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 69, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 97, a CDR2 domain comprising the amino acid sequence of SEQ ID NO: 96, and a CDR1 domain comprising the amino acid sequence of SEQ ID NO: 95.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 99, a CDR2 domain comprising the amino acid sequence of SEQ ID NO: 63, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 103, and a CDR1 domain comprising the amino acid sequence of SEQ ID NO: 102, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 106, a CDR2 domain comprising the amino acid sequence of SEQ ID NO: 110, and a CDR1 domain comprising the amino acid sequence of SEQ ID NO: 109, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable domain comprising an amino acid sequence set forth in SEQ ID NO: 1 and a light chain variable domain comprising an amino acid sequence set forth in SEQ ID NO: 5.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable domain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 9 and a light chain variable region comprising the amino acid sequence of SEQ ID NO: 13.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 17 and a light chain variable region comprising the amino acid sequence of SEQ ID NO: 20.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 24 and a light chain variable region comprising the amino acid sequence of SEQ ID NO: 27.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 24, or a sequence having at least 90%, 95%, 96%, 97%, 98%, or 99% identity to SEQ ID NO: 24, and/or a light chain comprising an amino acid sequence set forth in SEQ ID NO: 27, or a sequence having at least 90%, 95%, 96%, 97%, 98%, or 99% identity to SEQ ID NO: 27.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 29 and a light chain variable region comprising the amino acid sequence of SEQ ID NO: 32.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 29, or a sequence having at least 90%, 95%, 96%, 97%, 98%, or 99% identity to SEQ ID NO: 29, and/or a light chain comprising an amino acid sequence set forth in SEQ ID NO: 32, or a sequence having at least 90%, 95%, 96%, 97%, 98%, or 99% identity to SEQ ID NO: 32.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 35 and a light chain variable region comprising the amino acid sequence of SEQ ID NO: 38.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 38, or a sequence having at least 90%, 95%, 96%, 97%, 98%, or 99% identity to SEQ ID NO: 38.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 40 and a light chain variable region comprising the amino acid sequence of SEQ ID NO: 44.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 40, or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 45 and a light chain variable region comprising the amino acid sequence of SEQ ID NO: 49.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 53 and a light chain variable region comprising the amino acid sequence of SEQ ID NO: 57.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 57, or a sequence having at least 90%, 95%, 96%, 97%, 98%, or 99% identity to SEQ ID NO: 57.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 61 and a light chain variable region comprising the amino acid sequence of SEQ ID NO: 65.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 61, or a sequence having at least 90%, 95%, 96%, 97%, 98%, or 99% identity to SEQ ID NO: 61, and/or a light chain comprising an amino acid sequence set forth in SEQ ID NO: 65, or a sequence having at least 90%, 95%, 96%, 97%, 98%, or 99% identity to SEQ ID NO: 65.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 68 and a light chain variable region comprising the amino acid sequence of SEQ ID NO: 72.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 68, or a sequence having at least 90%, 95%, 96%, 97%, 98%, or 99% identity to SEQ ID NO: 68, and/or a light chain comprising an amino acid sequence set forth in SEQ ID NO: 72, or a sequence having at least 90%, 95%, 96%, 97%, 98%, or 99% identity to SEQ ID NO: 72.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 74 and a light chain variable region comprising the amino acid sequence of SEQ ID NO: 78.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 74, or a sequence having at least 90%, 95%, 96%, 97%, 98%, or 99% identity to SEQ ID NO: 74, and/or a light chain comprising an amino acid sequence set forth in SEQ ID NO: 78, or a sequence having at least 90%, 95%, 96%, 97%, 98%, or 99% identity to SEQ ID NO: 78.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 79 and a light chain variable region comprising the amino acid sequence of SEQ ID NO: 80.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 80, or a sequence having at least 90%, 95%, 96%, 97%, 98%, or 99% identity to SEQ ID NO: 80.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 81 and a light chain variable region comprising the amino acid sequence of SEQ ID NO: 84.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 84, or a sequence having at least 90%, 95%, 96%, 97%, 98%, or 99% identity to SEQ ID NO: 84.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 85 and a light chain variable region comprising the amino acid sequence of SEQ ID NO: 89.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 85, or a sequence having at least 90%, 95%, 96%, 97%, 98%, or 99% identity to SEQ ID NO: 85, and/or a light chain comprising an amino acid sequence set forth in SEQ ID NO: 89, or a sequence having at least 90%, 95%, 96%, 97%, 98%, or 99% identity to SEQ ID NO: 89.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 90 and a light chain variable region comprising the amino acid sequence of SEQ ID NO: 94.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 94, or a sequence having at least 90%, 95%, 96%, 97%, 98%, or 99% identity to SEQ ID NO: 94.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 98 and a light chain variable region comprising the amino acid sequence of SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 98, or a sequence having at least 90%, 95%, 96%, 97%, 98%, or 99% identity to SEQ ID NO: 98, and/or a light chain comprising an amino acid sequence set forth in SEQ ID NO: 100, or a sequence having at least 90%, 95%, 96%, 97%, 98%, or 99% identity to SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 101 and a light chain variable region comprising the amino acid sequence of SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 101, or a sequence having at least 90%, 95%, 96%, 97%, 98%, or 99% identity to SEQ ID NO: 101, and/or a light chain comprising an amino acid sequence set forth in SEQ ID NO: 100, or a sequence having at least 90%, 95%, 96%, 97%, 98%, or 99% identity to SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 104 and a light chain variable region comprising the amino acid sequence of SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 104, or a sequence having at least 90%, 95%, 96%, 97%, 98%, or 99% identity to SEQ ID NO: 104, and/or a light chain comprising an amino acid sequence set forth in SEQ ID NO: 100, or a sequence having at least 90%, 95%, 96%, 97%, 98%, or 99% identity to SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 107 and a light chain variable region comprising the amino acid sequence of SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 107, or a sequence having at least 90%, 95%, 96%, 97%, 98%, or 99% identity to SEQ ID NO: 107, and/or a light chain comprising an amino acid sequence set forth in SEQ ID NO: 100, or a sequence having at least 90%, 95%, 96%, 97%, 98%, or 99% identity to SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 108 and a light chain variable region comprising the amino acid sequence of SEQ ID NO: 100.

In other aspects, the invention provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 108, or a sequence having at least 90%, 95%, 96%, 97%, 98%, or 99% identity to SEQ ID NO: 108, and/or a light chain comprising an amino acid sequence set forth in SEQ ID NO: 100, or a sequence having at least 90%, 95%, 96%, 97%, 98%, or 99% identity to SEQ ID NO: 100.

In some embodiments, the at least one drug is conjugated to the antibody, or antigen-binding portion thereof, via a linker, e.g., a cleavable linker or a non-cleavable linker.

In other embodiments, the antibody, or antigen binding portion thereof, is an IgG1 isotype.

In other embodiments, the invention provides a pharmaceutical composition comprising an ADC mixture comprising a plurality of the ADC described herein, and a pharmaceutically acceptable carrier. In some embodiments, the ADC mixture has an average drug to antibody ratio (DAR) of 0 to 8.

In other aspects, the invention provides a method for treating cancer, comprising administering a therapeutically effective amount of an antibody or antigen binding portion thereof or an ADC described herein, to a subject in need thereof.

In one embodiment, the cancer is triple negative breast cancer. In another embodiment, the cancer is acute myeloid leukemia.

In other aspects, the invention provides a method for inhibiting or decreasing solid tumor growth in a subject having a solid tumor, said method comprising administering an effective amount of an antibody or antigen binding portion thereof or an ADC described herein, to the subject having the solid tumor, such that the solid tumor growth is inhibited or decreased.

In one embodiment, the cancer is triple negative breast cancer. In another embodiment, the cancer is acute myeloid leukemia.

In some embodiments, the cancer or tumor is characterized as having ILT3 expression or overexpression.

In some embodiments, the antibody, ADC, or antigen binding portion thereof is administered in combination with an additional agent or an additional therapy. In one embodiment, the additional agent is an immune checkpoint inhibitor. In some embodiments, the checkpoint inhibitor is an antibody, such as an antibody selected from the group consisting of an anti-PD1 antibody, an anti-PD-L1 antibody, an anti-CD38 antibody, an anti-CTLA-4 antibody, or a combination thereof. In other embodiments, the additional agent is radiation. In still other embodiments, the additional agent is a chemotherapeutic agent.

In other aspects, the invention provides a method for treating triple negative breast cancer (TNBC) in a subject, comprising administering a therapeutically effective amount of an anti-ILT3 antibody, ADC, or antigen binding portion thereof, to a subject in need thereof. In one embodiment, the anti-ILT3 antibody, ADC, or antigen binding portion thereof, is conjugated to at least one drug. In some embodiments, the antibody or antigen binding portion thereof is administered in combination with an additional agent or an additional therapy. In one embodiment, the additional agent is an immune checkpoint inhibitor. In some embodiments, the immune checkpoint inhibitor is an antibody, such as an antibody selected from the group consisting of an anti-PD1 antibody, an anti-PD-L1 antibody, an anti-CD38 antibody, or an anti-CTLA-4 antibody.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a TNBC tumor sample obtained from the subject are positive for ILT3 expression. In one embodiment, the cells expressing ILT3 in the sample are tumor infiltrating immune cells.

In another embodiment, the TNBC tumor sample obtained from the subject displays at least a low level of expression of ILT3. In another embodiment, the TNBC tumor sample obtained from the subject displays a high level of expression of ILT3. In one embodiment, the expression level of ILT3 is determined via immunohistochemical analysis.

In other aspects, the invention provides a method for treating an inflammatory disorder, e.g., pigmented villonodular synovitis (PVNS), comprising administering a therapeutically effective amount of an antibody or antigen binding portion thereof or an ADC described herein, to a subject in need thereof.

In other aspects, the invention provides a method for treating cancer in a subject, comprising administering a therapeutically effective amount of an antibody or antigen binding portion thereof or an ADC described herein, in combination with an immune checkpoint inhibitor, to a subject in need thereof. In one embodiment, the anti-ILT3 antibody, ADC, or antigen binding portion thereof, is conjugated to at least one drug. In another embodiment, the antibody, or antigen-binding portion thereof, binds to the same epitope as an antibody, or antigen binding portion thereof, of the invention.

In one embodiment, the immune checkpoint inhibitor is an antibody. In another embodiment, the antibody is selected from the group consisting of an anti-PD1 antibody, an anti-PD-L1 antibody, an anti-CD38 antibody, or an anti-CTLA-4 antibody, or a combination thereof.

In one embodiment, the cancer is triple negative breast cancer (TNBC) or acute myeloid leukemia.

BRIEF DESCRIPTION OF THE DRAWINGS

FIGS. 1A, 1B, 1C, and 1D illustrate the affinity of four human anti-ILT3 antibodies, 1E2F12H8 (A), 1E12H10 (B), 3C4A3 (C), and 8E11B6 (D) to human ILT3.

FIGS. 3A and 3B depict in vitro killing of ILT3 expressing THP1 cells by fully human anti-ILT3 antibodies. (A) Expression of ILT3 by THP1 AML cell line, antigen density was enumerated. Filled histogram, isotype control. Open histogram, anti-ILT3 antibody (clone ZM4.1, Biolegend, San Diego, CA). (B) In vitro killing of THP1 cells by anti-ILT3 antibody clones. Data normalized using the killing observed independently on THP1 cells with the IgG isotype control followed by 0.4 ug/mL of a single Fab' secondary antibody, conjugated with Saporin.

FIGS. 4A and 4B depict the effects of blocking ILT3 alone or in combination with anti-PDL1 antibodies on T cell activation and effector function. (A) Human anti-ILT3 antibodies or isotype control antibodies were cultured alone in mixed lymphocyte reactions for 6 days. Expression of CD25 was measured by flow cytometry on CD4+ and CD8+ T cells. Percent of CD25 positive cells in either CD4 or CD8 T cell population is depicted. (B) Human anti-ILT3 antibodies or isotype control antibodies were cultured in combination with antibodies against PD-L1 (Atezolizumab, Invivogen) in mixed lymphocyte reactions for 6 days. Supernatants were collected and IFNγ levels were measured by ELISA.

FIGS. 5A, 5B, 5C, 5D, 5E, and 5F depict the effects of blocking ILT3 in combination with antibodies against immuno-oncology targets on T cell activation. A mouse anti-ILT3 antibody, clone ZM4.1 (available from ThermoFisher), or isotype control antibodies, were cultured in combination with antibodies against CTLA-4 (Ipilimumab), PD-1 (Nivolomab) or PD-L1 (Atezolizumab) in mixed lymphocyte reactions for 6 days. Expression of CD25 was measured by flow cytometry on CD4+ and CD8+ T cells. Percent of CD25 positive cells in either CD4 or CD8 T cell population is depicted. Each dot represents an individual donor.

FIG. 6 depicts effects of blocking ILT3 in combination with antibodies against immuno-oncology targets on T cell effector function. Mouse anti-ILT3 antibody, clone ZM4.1 (available from ThermoFisher), or isotype control antibodies were cultured in combination with antibodies against CTLA-4 (Ipilimumab), PD-1 (Nivolomab) or PD-L1 (Atezolizumab) in mixed lymphocyte reactions for 6 days. Supernatants were collected and IFNγ levels were measured by ELISA.

DETAILED DESCRIPTION

Figure 2:
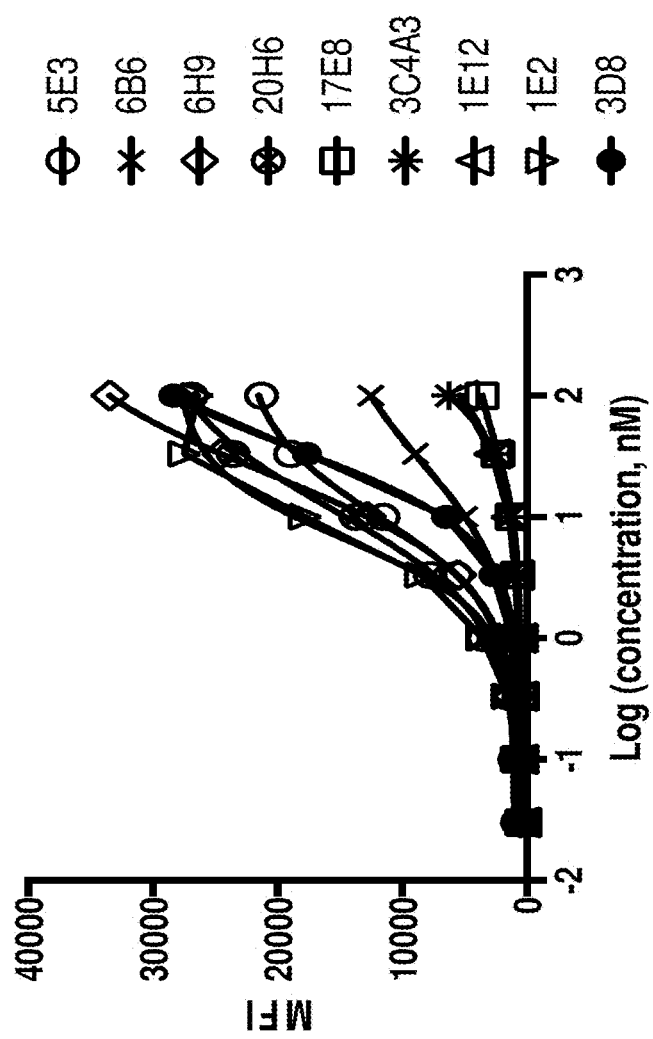
FIG. 2 depicts $EC_{50}$ of nine ILT3 antibodies against HEK293 cells expressing cynomolgus ILT3.

Various aspects of the disclosure relate to anti-ILT3 antibodies and antibody fragments, anti-ILT3 ADCs, and pharmaceutical compositions thereof, as well as nucleic acids, recombinant expression vectors and host cells for making such antibodies and fragments. Methods of using the antibodies and ADCs described herein to detect human ILT3, to bind to and inhibit human ILT3 on ILT3 expressing cells, including APCs, e.g., monocytes, dendritic cells (DCs) or macrophages (in vitro or in vivo), to upmodulate an immune response in vivo, increase T cell activation, and/or to treat ILT3-associated disorders, e.g., cancer, including, but not limited to, triple negative breast cancer (TNBC) or acute myeloid leukemia (AML). In one embodiment, the anti-ILT3 antibodies or ADCs of the invention are administered in combination with one or more immune checkpoint inhibitors (e.g., antibody or small molecule immune checkpoint inhibitors) for the treatment of a cancer, for example one or more of an anti-PD-1, anti-PD-L1, anti-CD38 antibody, or anti-CTLA4 antibody. In another embodiment of the invention, anti-ILT3 antibody drug conjugates (ADCs) of the invention (e.g., the ILT3 antibodies of the invention conjugated to a toxin) are internalized and induce cell death of cells endogenously expressing ILT3.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "immunogobulin-like transcript 3 antibody" or "anti-ILT3 antibody", used interchangeably herein, refer to an antibody that specifically binds to ILT3, e.g., human ILT3. An antibody "which binds" an antigen of interest, i.e., ILT3, is one capable of binding that antigen with sufficient affinity such that the antibody is useful in targeting a cell expressing the antigen. In a preferred embodiment, the antibody specifically binds to human ILT3 (hILT3). Examples of anti-ILT3 antibodies are disclosed in Example 2, below. Unless otherwise indicated, the term "anti-ILT3 antibody" is meant to refer to an antibody which binds to wild type ILT3, a variant, or an isoform of ILT3.

Three different invention of ILT3 produced by alternative splicing have been identified. An exemplary amino acid sequence of wild type human ILT3, which contains 448 amino acids, is provided below as SEQ ID NO: 149 (GenBank Accession No. AAH26309.1), where the signal peptide (amino acid residues 1-21) are underlined. The mature form of wild type ILT3 corresponds to the protein without the signal peptide, i.e., amino acid residues 22 to 448 of SEQ ID NO: 149.

```
  1  miptftallc lglslgprtd mqagplpkpt lwaepgsvis
     wgnsvtiwcq gtleareyrl 61  dkeespapwd rqnplepknk arfsipsmte dyagryrcyy
     rspvgwsqps dplelvmtga 121  yskptlsalp splvtsgksv tllcqsrspm dtfllikera
     ahpllhlrse hgaqqhqaef 181  pmspvtsvhg gtyrcfsshg fshyllshps dplelivsgs
     legprpsptr svstaagped 241  qplmptgsvp hsglrrhwev ligvlvvsil llslllflll
     qhwrqgkhrt laqrqadfqr 301  ppgaaepepk dgglqrrssp aadvqgenfc aavkntqped
     gvemdtrqsp hdedpqavty 361  akvkhsrprr emasppspls gefldtkdrq aeedrqmdte
     aaaseapqdv tyarlhsftl 421  rqkateppps qegaspaeps vyatlaih
```

ILT3 is a member of the leukocyte immunoglublin-like receptor (LIR) family and belongs to the subfamily B class of LIR receptors. The protein contains two extracellular immunoglobulin-like domains at amino acid residues 27-118 and 130-198, a transmembrane domain at amino acid residues 260-280, and three cytoplasmic immunoreceptor tyrosine-based inhibitory motifs (ITIMs) at amino acid residues 358-363, 410-415, and 440-445, which are involved in immune regulation.

The terms "specific binding" or "specifically binding", as used herein, in reference to the interaction of an ILT3 antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to hILT3" or "specific binding to hILT3", as used herein, refers to the ability of an anti-ILT3 antibody or ADC to interact with ILT3 (human or cynomolgus monkey ILT3) with a dissociation constant ($K_D$) of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less. In another embodiment, the phrase "specifically binds to hILT3" or "specific binding to hILT3", as used herein, refers to the ability of an anti-ILT3 antibody or ADC to interact with hILT3 with a dissociation constant ($K_D$) of between about 1 pM (0.001 nM) to 2,000 nM, between about 500 pM (0.5 nM) to 1,000 nM, between about 500 pM (0.5 nM) to 500 nM, between about 1 nM to 200 nM, between about 1 nM to 100 nM, between about 1 nM to 50 nM, between about 1 nM to 20 nM, or between about 1 nM to 5 nM. In one embodiment, $K_D$ is determined by surface plasmon resonance. In another embodiment, $K_D$ is determined as described in Example 2, below.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG 3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hIL-13). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds ILT3 is substantially free of antibodies that specifically bind antigens other than ILT3). An isolated antibody that specifically binds ILT3 may, however, have cross-reactivity to other antigens, such as ILT3 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 110.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-ILT3 DVD.

The term "activity" includes activities such as the binding specificity/affinity of an antibody or ADC for an antigen, for example, an anti-hILT3 antibody that binds to an ILT3 antigen. In one embodiment, an anti-ILT3 antibody or anti-ILT3 ADC activity includes, but it not limited to, binding to ILT3 in vitro; binding to ILT3 on cells expressing ILT3 in vivo (such as, for example, APCs including dentritic cells (DCs), monocytes, and macrophages, B-cells, and natural killer (NK) cells, as well as tumor infiltrating immune cells such as myeloid cells); upmodulating immune response in vivo; increasing T cell activation in vivo; increasing CD8+ T cell expansion and effector functions that would result in anti-tumor response; inducing cell death in cells expressing ILT3, including myeloid derived suppressor cells (MDSCs); inhibiting cancer cell invasion and metastasis; decreasing or inhibiting cancer, e.g., triple negative breast cancer (TNBC) and acute myeloid leukemia (AML); and decreasing or inhibiting tumor cellular proliferation or tumor growth in vivo. In some embodiments, the tumor can be an ILT3 negative tumor or an ILT3 positive tumor. In one embodiment, an anti-ILT3 antibody is capable of being internalized into a cell expressing ILT3.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Jönsson, U., et al. (1993) *Ann. Biol. Clin.* 51:19-26; Jönsson, U., et al. (1991) *Biotechniques* 11:620-627; Jöhnsson, B., et al. (1995) *J. Mol. Recognit.* 8:125-131; and Johnnson, B., et al. (1991) *Anal. Biochem.* 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods).

Examples of labels for polypeptides include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "immunogobulin-like transcript 3 antibody drug conjugate," "anti-ILT3 antibody drug conjugate," or "anti-ILT3 ADC", used interchangeably herein, refer to an ADC comprising an antibody that specifically binds to ILT3, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "ILT3 associated disorder," as used herein, includes any disorder or disease (including proliferative disorders, e.g., cancer) that is marked, diagnosed, detected or identified by a phenotypic or genotypic aberration of ILT3 genetic components or expression during the course or etiology of the disease or disorder. In this regard an ILT3 phenotypic aberration or determinant may, for example, comprise increased or decreased levels of ILT3 protein expression on one cell population, e.g., a cancer cell population, or an immune cell population (such as a tumor infiltrating cell population), as compared to another cell population, e.g., a normal cell population, or increased or decreased ILT3 protein expression on certain definable cell populations, or increased or decreased ILT3 protein expression at an inappropriate phase or stage of a cell lifecycle. It will be appreciated that similar expression patterns of genotypic determinants (e.g., mRNA transcription levels) of ILT3 may also be used to classify or detect ILT3 associated disorders. An "ILT3 associated disorder," as used herein, also includes a disorder characterized by infiltration of cells expressing ILT3, e.g., tumor infiltrating immune cells or myeloid derived suppressor cells (MDSCs). In one embodiment, an ILT3 associated disorder is triple negative breast cancer (TNBC). In one embodiment, an ILT3 associated disorder is acute myeloid leukemia (AML).

An "ILT3 associated disorder," as used herein, also includes inflammatory disorders including, but not limited to, pigmented villonodular synovitis (PVNS). In one embodiment, an anti-ILT3 antibody or ADC of the present invention can be used to treat an inflammatory disorder in a subject including, but not limited to PVNS.

The term "cancer," as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenorna, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. Acute myeloid leukemia, adrenocortical carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-ILT3 antibody or ADC of the present invention can be used to treat a cancer in a subject including, but not limited to Hodgkin's lymphoma, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarian serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma, kidney renal clear cell carcinoma, and kidney renal papillary cell carcinoma.

In one embodiment, the antibodies or ADCs of the invention are administered to a patient having a solid tumor, including an advanced solid tumor. In one embodiment, the tumor expresses ILT3 or contains tumor infiltrating immune cells or myeloid derived suppressor cells (MDSCs) expressing ILT3. In another embodiment, the tumor does not express ILT3 and/or does not contain tumor infiltrating immune cells or MDSCs expressing ILT3. In another embodiment, administration of the antibodies of the invention to a patient upregulates an immune response in the patient. In another embodiment, administration of ADCs of the invention induce cell death of ILT3 expressing cells.

The term "ILT3 expressing tumor," as used herein, refers to a tumor which expresses ILT3 protein (including a tumor comprising tumor infiltrating cells that express ILT3 protein), such as a triple negative breast cancer (TNBC) tumor. In one embodiment, ILT3 expression in a tumor is determined using immunohistochemical staining of tumor cell membranes, where any immunohistochemical staining above background level in a tumor sample indicates that the tumor is an ILT3 expressing tumor. In another embodiment, an ILT3 expressing tumor, e.g., a TNBC tumor expressing ILT3, is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for ILT3 expression. In one embodiment, the ILT3 expressing cells in the sample are tumor infiltrating immune cells. In another embodiment, ILT3 positive expression is determined based on membrane staining as determined by, e.g., immunohistochemistry (IHC) analysis.

An ILT3 expressing tumor is identified as having an "elevated level of ILT3" or "expressing ILT3 at an elevated level" when level level of ILT3 is higher than in tissue surrounding the cancer. In some embodiments, an "elevated level of ILT3" is one in which 5% or more of the cells in a tumor sample have membrane staining. In some embodiments a "high level" in regard to ILT3 is 5% or more staining, for example, 5, 10, 20, 30, 40, 50, 60, 70, 80, 90, or 100% of the cells in the tumor sample are stained. In some embodiments, the protein expression levels can be measured by IHC analysis. In another embodiment, the ILT3 expressing cells in the sample are tumor infiltrating immune cells.

An ILT3 expressing tumor is identified as having a "low level of ILT3" or "expressing ILT3 at a low level" is one in which 5% or less of the cells in a tumor sample have membrane staining In some embodiments a "low level" in regard to ILT3 is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis. In another embodiment, the ILT3 expressing cells in the sample are tumor infiltrating immune cells.

A cell that expresses no ILT3 can also be described as expressing a "low level of ILT3". Thus, the phrase "expresses a low level of ILT3" encompasses no ILT3 expression. In some embodiments, a low level of ILT3 is within the background staining levels. In some embodiments, a sample that is ILT3 "negative" has no ILT3 expression or a low level of ILT3. In some embodiments, ILT3 staining is negative when no or less than 5%, 4%, 3%, 2%, or 1% of the cells have membrane staining for ILT3.

As used herein, the term TNBC "tumor sample" refers to a tumor tissue or cell sample obtained from a TNBC tumor. The sample can include both tumor cells and tumor infiltrating cells, e.g., tumor infiltrating immune cells.

As used herein, the term "non-cancer sample" or "normal sample" refers to a sample from a normal tissue (e.g., a breast tissue sample). In some embodiments, the non-cancer sample comes from the same subject, but is from a different part of the subject than that being tested. In some embodiments, the non-cancer sample is from a tissue area surrounding or adjacent to the cancer, e.g., TNBC. In some embodiments, the non-cancer sample is not from the subject being tested, but is a sample from a subject known to have, or not to have, a disorder in question (for example, a particular cancer such as TNBC or ILT3 related disorder). In some embodiments, the non-cancer sample is from the same subject, but from a point in time before the subject developed cancer. In some embodiments, the reference sample is from a benign cancer sample (for example, benign breast cancer sample), from the same or a different subject.

Methods for detecting expression of ILT3 in a tumor are known in the art. For example, immunohistochemistry (IHC) analysis was used by the inventors to show that ILT3 is expressed in triple negative breast cancer (TNBC) tissue. In particular, ILT3 was shown to be predominantly expressed by CD68$^+$ tumor infiltrating immune cells (see Example 1).

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-ILT3 antibodies or ADCs are used to treat solid tumors likely to overexpress ILT3.

The term "administering" as used herein is meant to refer to the delivery of a substance (e.g., an anti-ILT3 antibody or ADC) to achieve a therapeutic objective (e.g., the treatment of an ILT3-associated disorder or the inhibition or reduction of a tumor or the treatment of an inflammatory disorder such as PVNS). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-ILT3 antibody or ADC and an additional therapeutic agent. The additional therapeutic agent may be administered concomitant with, prior to, or following the administration of the anti-ILT3 antibody or ADC. In one embodiment, the anti-ILT3 antibodies or ADCs of the invention are administered in combination with one or more immune checkpoint inhibitors (e.g., one or more antibody or small molecule immune checkpoint inhibitors) for the treatment of a cancer or an inflammatory disorder such as PVNS.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or an inflammatory disorder such as PVNS, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-ILT3 Antibodies

One aspect disclosed herein provides humanized anti-ILT3 antibodies, or antigen binding portions thereof. Another aspect disclosed herein provides human anti-ILT3 antibodies, or antigen binding portions thereof. In one embodiment, the antibodies disclosed herein bind human ILT3. In another embodiment, the antibodies disclosed herein bind cynomolgus monkey ILT3. In another embodiment, the antibodies disclosed herein bind human ILT3 expressed on APCs, e.g., dentritic cells (DCs), monocytes, and macrophages, B-cells, and natural killer (NK) cells. In another embodiment, the antibodies disclosed herein bind human ILT3 expressed on tumor infiltrating immune cells, e.g., myeloid cells. In another embodiment, the antibodies disclosed herein bind human ILT3 expressed on tumor cells.

Another aspect disclosed herein features antibody drug conjugates (ADCs) comprising an anti-ILT3 antibody described herein and at least one drug(s). The antibodies or ADCs disclosed herein have characteristics including, but not limited to, binding to human ILT3 in vitro, binding human ILT3 expressed on APCs, e.g., dentritic cells (DCs), monocytes, and macrophages, B-cells, and natural killer (NK) cells, binding human ILT3 expressed on tumor infiltrating immune cells, e.g., myeloid cells, binding human ILT3 expressed on tumor cells, upregulating an immune response in vivo, increasing T cell activation in vivo; increasing CD8+ T cell expansion and effector functions that would result in anti-tumor response, inducing cell death in cells expressing ILT3, including, but not limited to, myeloid derived suppressor cells (MDSCs) and tumor associated macrophages, and decreasing or inhibiting cancer, tumor cellular proliferation or tumor growth, or tumor invasion and metastasis. ADCs disclosed herein, in particular, have characteristics including, but not limited to, inducing cell death in cells expressing ILT3, e.g., myeloid cells expressing ILT3. In one embodiment, an anti-ILT3 antibody or ADC disclosed herein is capable of being internalized into a cell expressing ILT3.

In one embodiment, anti-ILT3 antibodies are disclosed which have the ability to bind to ILT3, as described in the Examples below. Collectively, the novel antibodies are referred to herein as "ILT3 antibodies." The anti-ILT3 antibodies, ADCs, or antigen binding fragments thereof, are able to inhibit or decrease tumor growth in vivo. The tumor can be an ILT3 negative tumor or an ILT3 expressing tumor. In various embodiments, anti-ILT3 antibodies, ADCs, or antigen binding fragments thereof, are capable of modulating a biological function of ILT3. In other embodiments of the foregoing aspects, the anti-ILT3 antibodies, ADCs, or antigen binding fragments thereof, bind ILT3 on cells expressing ILT3. Thus, the disclosure includes anti-ILT3 antibodies, ADCs, or antigen binding fragments thereof, that are effective at inhibiting or decreasing tumor growth.

In addition, the present inventors have shown that ILT3 is expressed by tumor infiltrating cells in triple negative breast cancer (see Example 1). TNBC is notoriously biologically aggressive and difficult to treat (see, Wahba and El-Haddad (2015) *Cancer Biol. Med.* 12(2): 106-116). According, the anti-ILT3 antibodies, ADCs, and antigen-binding portions thereof, can be used for the treatment of TNBC in a subject. In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a TNBC tumor sample are positive for ILT3 expression. In another embodiment, a TNBC tumor sample has a high level of ILT3 expression. For example, in one embodiment, at least 5% or more of the cells in a TNBC tumor sample have membrane staining. In another embodiment, a TNBC tumor sample obtained from the subject displays a low level of expression of ILT3. The expression level of ILT3 can be determined by any method known in the art. For example, the expression level of ILT3 can be determined via immunohistochemical analysis. In another embodiment, the TNBC has been previously treated with another anti-cancer agent or anti-cancer therapy, e.g., a chemotherapy. In one embodiment, the TNBC is resistant to chemotherapy.

Antibodies having combinations of any of the aforementioned characteristics are contemplated as aspects of the disclosure. ADCs, described in more detail below, may also have any of the foregoing characteristics.

One aspect of the disclosure features an anti-human ILT3 (anti-hILT3) Antibody Drug Conjugate (ADC) comprising an anti-hILT3 antibody conjugated to a drug via a linker. Exemplary anti-ILT3 antibodies (and sequences thereof) that can be used in the ADCs are described herein.

The anti-ILT3 antibodies described herein provide the ADCs with the ability to bind to ILT3 such that the cytotoxic molecule attached to the antibody may be delivered to the ILT3-expressing cell, particularly a ILT3 expressing cancer cell or a myeloid derived suppressor cell (MDSC).

While the term "antibody" is used throughout, it should be noted that antibody fragments (i.e., antigen-binding portions of an anti-ILT3 antibody) are also included in the disclosure and may be included in the embodiments (methods and compositions) described throughout. For example, an anti-ILT3 antibody fragment may be conjugated to the drugs, as described herein. In certain embodiments, an anti-ILT3 antibody binding portion is a Fab, a Fab', a F(ab')2, a Fv, a disulfide linked Fv, an scFv, a single domain antibody, or a diabody.

Example 2 describes the generation of twenty-one human recombinant ILT3 antibodies against the extracellular domain of human ILT3. The heavy and light chain variable region amino acid sequences for these human antibodies are set forth in Table 2. The heavy and light chain variable region nucleic acid sequences for these human antibodies are set forth in Table 3.

Thus, in one embodiment, the disclosure includes human anti-hILT3 antibodies, or antigen binding portions thereof, comprising a heavy chain variable region comprising an amino acid sequence selected from the group consisting of SEQ ID NOs:1, 9, 17, 24, 29, 35, 40, 45, 53, 61, 68, 74, 79, 81, 85, 90, 98, 101, 104, 107 and 108; and a light chain variable region comprising an amino acid sequence selected from the group consisting of 5, 13, 20, 27, 32, 38, 44, 49, 57, 65, 72, 78, 80, 84, 89, 94, and 100.

In one embodiment, the disclosure includes a human anti-hILT3 antibody, or antigen binding portion thereof, comprising an HC CDR set (CDR1, CDR2, and CDR3) selected from the group consisting of SEQ ID NOs: 2, 3, and 4; SEQ ID NOs: 10, 11, and 12; SEQ ID NOs: 2, 18, and 19; SEQ ID NOs: 10, 25, and 26; SEQ ID NOs: 30, 31, and 12; SEQ ID NOs: 36, 37, and 12; SEQ ID NOs: 41, 42, and 43; SEQ ID NOs: 46, 47, and 48; SEQ ID NOs: 54, 55, and 56; SEQ ID NOs: 62, 63, and 64; SEQ ID NOs: 69, 70, and 71; SEQ ID NOs: 75, 76, and 77; SEQ ID NOs: 46, 70, and 71; SEQ ID NOs: 82, 83, and 48; SEQ ID NOs: 86, 87, and 88; SEQ ID NOs: 91, 92, and 93; SEQ ID NOs: 46, 63, and 99; SEQ ID NOs: 102, 103, and 48; SEQ ID NOs: 62, 105, and 106; and SEQ ID NOs: 109, 110, and 106.

and an LC CDR set (CDR1, CDR2, and CDR3) selected from the group consisting of SEQ ID NOs: 6, 7, and 8; SEQ ID NOs: 14, 15, and 16; SEQ ID NOs: 21, 22, and 23; SEQ ID NOs: 6, 7, and 28; SEQ ID NOs: 33, 34, and 16; SEQ ID NOs: 33, 39, and 16; SEQ ID NOs: 50, 51, and 52; SEQ ID NOs: 59, 59, and 60; SEQ ID NOs: 66, 67, and 60; SEQ ID NOs: 50, 73, and 52; SEQ ID NOs: 50, 73, and 60; and SEQ ID NOs: 95, 96, and 97.

In one embodiment, an anti-ILT3 antibody, or antigen binding portion thereof, is the human antibody E2F12H8 (also referred to herein as 1E2F12H8). The E2F12H8 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-ILT3 antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-ILT3 antibody, or antigen binding portion thereof, which is the human antibody E12H10 (also referred to herein as 1E12H10). The E12H10 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-ILT3 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-ILT3 antibody, or antigen binding portion thereof, which is the human antibody 3C4A3. The 3C4A3 antibody comprises a heavy chain variable region comprising a CDR3 domain comprising the amino acid sequence of SEQ ID NO: 19, a CDR2 domain comprising the amino acid sequence of SEQ ID NO: 18, and a CDR1 domain comprising the amino acid sequence of SEQ ID NO: 2, and a light chain variable region comprising a CDR3 domain comprising the amino acid sequence of SEQ ID NO: 23, a CDR2 domain comprising the amino acid sequence of SEQ ID NO: 22, and a CDR1 domain comprising the amino acid sequence of SEQ ID NO: 21. In further embodiments, the disclosure provides an antibody having a heavy chain variable region comprising the amino acid sequence of SEQ ID NO: 17 and a light chain variable region comprising the amino acid sequence of SEQ ID NO: 20.

In some embodiments, an anti-ILT3 antibody, or antigen-binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In one embodiment, the disclosure features an anti-ILT3 antibody, or antigen binding portion thereof, which is the human antibody 8E11B6. The 8E11B6 antibody comprises a heavy chain variable region comprising a CDR3 domain comprising the amino acid sequence of SEQ ID NO: 26, a CDR2 domain comprising the amino acid sequence of SEQ ID NO: 25, and a CDR1 domain comprising the amino acid sequence of SEQ ID NO: 10, and a light chain variable region comprising a CDR3 domain comprising the amino acid sequence of SEQ ID NO: 28, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 24 and a light chain variable region comprising the amino acid sequence of SEQ ID NO: 27.

In some embodiments, an anti-ILT3 antibody, or antigen-binding portion thereof, comprises a heavy chain comprising an amino acid sequence set forth in SEQ ID NO: 24, or a sequence having at least 90%, 95%, 96%, 97%, 98%, or 99% identity to SEQ ID NO: 24, and/or a light chain comprising an amino acid sequence set forth in SEQ ID NO: 27, or a sequence having at least 90%, 95%, 96%, 97%, 98%, or 99% identity to SEQ ID NO: 27.

In one embodiment, the disclosure features an anti-ILT3 antibody, or antigen binding portion thereof, which is the human antibody 17E8_27C5. The 17E8_27C5 antibody comprises a heavy chain variable region comprising a CDR3 domain comprising the amino acid sequence of SEQ ID NO: 12, a CDR2 domain comprising the amino acid sequence of SEQ ID NO: 31, and a CDR1 domain comprising the amino acid sequence of SEQ ID NO: 30, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33. In further embodiments, the disclosure provides an antibody having a heavy chain variable region comprising the amino acid sequence of SEQ ID NO: 29 and a light chain variable region comprising the amino acid sequence of SEQ ID NO: 32.

In some embodiments, an anti-ILT3 antibody, or antigen-binding portion thereof, comprises a heavy chain comprising an amino acid sequence set forth in SEQ ID NO: 29, or a sequence having at least 90%, 95%, 96%, 97%, 98%, or 99% identity to SEQ ID NO: 29, and/or a light chain comprising an amino acid sequence set forth in SEQ ID NO: 32, or a sequence having at least 90%, 95%, 96%, 97%, 98%, or 99% identity to SEQ ID NO: 32.

In one embodiment, the disclosure features an anti-ILT3 antibody, or antigen binding portion thereof, which is the human antibody 17F4_27C6. The 17F4_27C6 antibody comprises a heavy chain variable region comprising a CDR3 domain comprising the amino acid sequence of SEQ ID NO: 12, a CDR2 domain comprising the amino acid sequence of SEQ ID NO: 37, and a CDR1 domain comprising the amino acid sequence of SEQ ID NO: 36, and a light chain variable region comprising a CDR3 domain comprising the amino acid sequence of SEQ ID NO: 16, a CDR2 domain comprising the amino acid sequence of SEQ ID NO: 39, and a CDR1 domain comprising the amino acid sequence of SEQ ID NO: 33. In further embodiments, the disclosure provides an antibody having a heavy chain variable region comprising the amino acid sequence of SEQ ID NO: 35 and a light chain variable region comprising the amino acid sequence of SEQ ID NO: 38.

In some embodiments, an anti-ILT3 antibody, or antigen-binding portion thereof, comprises a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 38, or a sequence having at least 90%, 95%, 96%, 97%, 98%, or 99% identity to SEQ ID NO: 38.

In one embodiment, the disclosure features an anti-ILT3 antibody, or antigen binding portion thereof, which is the human antibody 11H10_27 D4. The 11H10_27 D4 antibody comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 16, a CDR2 domain comprising the amino acid sequence of SEQ ID NO: 34, and a CDR1 domain comprising the amino acid sequence of SEQ ID NO: 33. In further embodiments, the disclosure provides an antibody having a heavy chain variable region comprising the amino acid sequence of SEQ ID NO: 40 and a light chain variable region comprising the amino acid sequence of SEQ ID NO: 44.

In some embodiments, an anti-ILT3 antibody, or antigen-binding portion thereof, comprises a heavy chain comprising an amino acid sequence set forth in SEQ ID NO: 40, or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In one embodiment, the disclosure features an anti-ILT3 antibody, or antigen binding portion thereof, which is the human antibody 1C4_24B4. The 1C4_24B4 antibody comprises a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50. In further embodiments, the disclosure provides an antibody having a heavy chain variable region comprising the amino acid sequence of SEQ ID NO: 45 and a light chain variable region comprising the amino acid sequence of SEQ ID NO: 49.

In some embodiments, an anti-ILT3 antibody, or antigen-binding portion thereof, comprises a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In one embodiment, the disclosure features an anti-ILT3 antibody, or antigen binding portion thereof, which is the human antibody 20H6_24C3. The 20H6_24C3 antibody comprises a heavy chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54, and a light chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58. In further embodiments, the disclosure provides an antibody having a heavy chain variable region comprising the amino acid sequence of SEQ ID NO: 53 and a light chain variable region comprising the amino acid sequence of SEQ ID NO: 57.

In some embodiments, an anti-ILT3 antibody, or antigen-binding portion thereof, comprises a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 57, or a sequence having at least 90%, 95%, 96%, 97%, 98%, or 99% identity to SEQ ID NO: 57.

In one embodiment, the disclosure features an anti-ILT3 antibody, or antigen binding portion thereof, which is the human antibody 14E7_27C1. The 14E7_27C1 antibody comprises a heavy chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 67, and a CDR1 domain comprising the amino acid sequence of SEQ ID NO: 66. In further embodiments, the disclosure provides an antibody having a heavy chain variable region comprising the amino acid sequence of SEQ ID NO: 61 and a light chain variable region comprising the amino acid sequence of SEQ ID NO: 65.

In some embodiments, an anti-ILT3 antibody, or antigen-binding portion thereof, comprises a heavy chain comprising an amino acid sequence set forth in SEQ ID NO: 61, or a sequence having at least 90%, 95%, 96%, 97%, 98%, or 99% identity to SEQ ID NO: 61, and/or a light chain comprising an amino acid sequence set forth in SEQ ID NO: 65, or a sequence having at least 90%, 95%, 96%, 97%, 98%, or 99% identity to SEQ ID NO: 65.

In one embodiment, the disclosure features an anti-ILT3 antibody, or antigen binding portion thereof, which is the human antibody 5A2_24 A1. The 5A2_24 A1 antibody comprises a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 69, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 68 and a light chain variable region comprising the amino acid sequence of SEQ ID NO: 72.

In some embodiments, an anti-ILT3 antibody, or antigen-binding portion thereof, comprises a heavy chain comprising an amino acid sequence set forth in SEQ ID NO: 68, or a sequence having at least 90%, 95%, 96%, 97%, 98%, or 99% identity to SEQ ID NO: 68, and/or a light chain comprising an amino acid sequence set forth in SEQ ID NO: 72, or a sequence having at least 90%, 95%, 96%, 97%, 98%, or 99% identity to SEQ ID NO: 72.

In one embodiment, the disclosure features an anti-ILT3 antibody, or antigen binding portion thereof, which is the human antibody 5E3_24B4. The 5E3_24B4 antibody comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 74 and a light chain variable region comprising the amino acid sequence of SEQ ID NO: 78.

In some embodiments, an anti-ILT3 antibody, or antigen-binding portion thereof, comprises a heavy chain comprising an amino acid sequence set forth in SEQ ID NO: 74, or a sequence having at least 90%, 95%, 96%, 97%, 98%, or 99% identity to SEQ ID NO: 74, and/or a light chain comprising an amino acid sequence set forth in SEQ ID NO: 78, or a sequence having at least 90%, 95%, 96%, 97%, 98%, or 99% identity to SEQ ID NO: 78.

In one embodiment, the disclosure features an anti-ILT3 antibody, or antigen binding portion thereof, which is the human antibody 7C12_24A6. The 7C12_24A6 antibody comprises a heavy chain variable region comprising a CDR3 domain comprising the amino acid sequence of SEQ ID NO: 71, a CDR2 domain comprising the amino acid sequence of SEQ ID NO: 70, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 79 and a light chain variable region comprising the amino acid sequence of SEQ ID NO: 80.

In some embodiments, an anti-ILT3 antibody, or antigen-binding portion thereof, comprises a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 80, or a sequence having at least 90%, 95%, 96%, 97%, 98%, or 99% identity to SEQ ID NO: 80.

In one embodiment, the disclosure features an anti-ILT3 antibody, or antigen binding portion thereof, which is the human antibody 6H9_27 D5. The 6H9_27 D5 antibody comprises a heavy chain variable region comprising a CDR3 domain comprising the amino acid sequence of SEQ ID NO: 48, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 81 and a light chain variable region comprising the amino acid sequence of SEQ ID NO: 84.

In some embodiments, an anti-ILT3 antibody, or antigen-binding portion thereof, comprises a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 84, or a sequence having at least 90%, 95%, 96%, 97%, 98%, or 99% identity to SEQ ID NO: 84.

In one embodiment, the disclosure features an anti-ILT3 antibody, or antigen binding portion thereof, which is the human antibody 10A5_24 A2. The 10A5_24 A2 antibody comprises a heavy chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 85 and a light chain variable region comprising the amino acid sequence of SEQ ID NO: 89.

In some embodiments, an anti-ILT3 antibody, or antigen-binding portion thereof, comprises a heavy chain comprising an amino acid sequence set forth in SEQ ID NO: 85, or a sequence having at least 90%, 95%, 96%, 97%, 98%, or 99% identity to SEQ ID NO: 85, and/or a light chain comprising an amino acid sequence set forth in SEQ ID NO: 89, or a sequence having at least 90%, 95%, 96%, 97%, 98%, or 99% identity to SEQ ID NO: 89.

In one embodiment, the disclosure features an anti-ILT3 antibody, or antigen binding portion thereof, which is the human antibody 16B10_27 D2. The 16B10_27 D2 antibody comprises a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 97, a CDR2 domain comprising the amino acid sequence of SEQ ID NO: 96, and a CDR1 domain comprising the amino acid sequence of SEQ ID NO: 95. In further embodiments, the disclosure provides an antibody having a heavy chain variable region comprising the amino acid sequence of SEQ ID NO: 90 and a light chain variable region comprising the amino acid sequence of SEQ ID NO: 94.

In some embodiments, an anti-ILT3 antibody, or antigen-binding portion thereof, comprises a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 94, or a sequence having at least 90%, 95%, 96%, 97%, 98%, or 99% identity to SEQ ID NO: 94.

In one embodiment, the disclosure features an anti-ILT3 antibody, or antigen binding portion thereof, which is the human antibody 3D8D11. The 3D8D11 antibody comprises a heavy chain variable region comprising a CDR3 domain comprising the amino acid sequence of SEQ ID NO: 99, a CDR2 domain comprising the amino acid sequence of SEQ ID NO: 63, and a CDR1 domain comprising the amino acid sequence of SEQ ID NO: 46, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 98 and a light chain variable region comprising the amino acid sequence of SEQ ID NO: 100.

In some embodiments, an anti-ILT3 antibody, or antigen-binding portion thereof, comprises a heavy chain comprising an amino acid sequence set forth in SEQ ID NO: 98, or a sequence having at least 90%, 95%, 96%, 97%, 98%, or 99% identity to SEQ ID NO: 98, and/or a light chain comprising an amino acid sequence set forth in SEQ ID NO: 100, or a sequence having at least 90%, 95%, 96%, 97%, 98%, or 99% identity to SEQ ID NO: 100.

In one embodiment, the disclosure features an anti-ILT3 antibody, or antigen binding portion thereof, which is the human antibody 3H3_24B2. The 3H3_24B2 antibody comprises a heavy chain variable region comprising a CDR3 domain comprising the amino acid sequence of SEQ ID NO: 48, a CDR2 domain comprising the amino acid sequence of SEQ ID NO: 103, and a CDR1 domain comprising the amino acid sequence of SEQ ID NO: 102, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 101 and a light chain variable region comprising the amino acid sequence of SEQ ID NO: 100.

In some embodiments, an anti-ILT3 antibody, or antigen-binding portion thereof, comprises a heavy chain comprising an amino acid sequence set forth in SEQ ID NO: 101, or a sequence having at least 90%, 95%, 96%, 97%, 98%, or 99% identity to SEQ ID NO: 101, and/or a light chain comprising an amino acid sequence set forth in SEQ ID NO: 100, or a sequence having at least 90%, 95%, 96%, 97%, 98%, or 99% identity to SEQ ID NO: 100.

In one embodiment, the disclosure features an anti-ILT3 antibody, or antigen binding portion thereof, which is the human antibody 6B6_24B5. The 6B6_24B5 antibody comprises a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 104 and a light chain variable region comprising the amino acid sequence of SEQ ID NO: 100.

In some embodiments, an anti-ILT3 antibody, or antigen-binding portion thereof, comprises a heavy chain comprising an amino acid sequence set forth in SEQ ID NO: 104, or a sequence having at least 90%, 95%, 96%, 97%, 98%, or 99% identity to SEQ ID NO: 104, and/or a light chain comprising an amino acid sequence set forth in SEQ ID NO: 100, or a sequence having at least 90%, 95%, 96%, 97%, 98%, or 99% identity to SEQ ID NO: 100.

In one embodiment, the disclosure features an anti-ILT3 antibody, or antigen binding portion thereof, which is the human antibody 8C7_24B1. The 8C7_24B1 antibody comprises a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 107 and a light chain variable region comprising the amino acid sequence of SEQ ID NO: 100.

In some embodiments, an anti-ILT3 antibody, or antigen-binding portion thereof, comprises a heavy chain comprising an amino acid sequence set forth in SEQ ID NO: 107, or a sequence having at least 90%, 95%, 96%, 97%, 98%, or 99% identity to SEQ ID NO: 107, and/or a light chain comprising an amino acid sequence set forth in SEQ ID NO: 100, or a sequence having at least 90%, 95%, 96%, 97%, 98%, or 99% identity to SEQ ID NO: 100.

In one embodiment, the disclosure features an anti-ILT3 antibody, or antigen binding portion thereof, which is the human antibody 4F4_27 D3. The 4F4_27 D3 antibody comprises a heavy chain variable region comprising a CDR3 domain comprising the amino acid sequence of SEQ ID NO: 106, a CDR2 domain comprising the amino acid sequence of SEQ ID NO: 110, and a CDR1 domain comprising the amino acid sequence of SEQ ID NO: 109, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50. In further embodiments, the disclosure provides an antibody having a heavy chain variable region comprising the amino acid sequence of SEQ ID NO: 108 and a light chain variable region comprising the amino acid sequence of SEQ ID NO: 100.

In some embodiments, an anti-ILT3 antibody, or antigen-binding portion thereof, comprises a heavy chain comprising an amino acid sequence set forth in SEQ ID NO: 108, or a sequence having at least 90%, 95%, 96%, 97%, 98%, or 99% identity to SEQ ID NO: 108, and/or a light chain comprising an amino acid sequence set forth in SEQ ID NO: 100, or a sequence having at least 90%, 95%, 96%, 97%, 98%, or 99% identity to SEQ ID NO: 100.

The foregoing anti-ILT3 antibody CDR sequences establish a novel family of ILT3 binding proteins, isolated in accordance with this disclosure, and comprising antigen binding polypeptides that include the CDR sequences listed in Table 2, as well as in the Sequence Summary.

To generate and to select CDRs having preferred ILT3 binding and/or neutralizing activity with respect to hILT3, standard methods known in the art for generating antibodies, or antigen binding portions thereof, and assessing the ILT3 binding and/or neutralizing characteristics of those antibodies, or antigen binding portions thereof, may be used, including but not limited to those specifically described herein (see, e.g., Example 2).

In certain embodiments, the antibody comprises a heavy chain constant region, such as an IgG 1, IgG2, IgG3, IgG4, IgA, IgE, IgM, or IgD constant region. In certain embodiments, the anti-ILT3 antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-ILT3 antibody binding portion is a Fab, a Fab', a F(ab')2, a Fv, a disulfide linked Fv, an scFv, a single domain antibody, or a diabody.

In certain embodiments, the anti-ILT3 antibody, or antigen binding portion thereof, is a multispecific antibody, e.g. a bispecific antibody.

In certain embodiments, the anti-ILT3 antibody, or antigen binding portion thereof, comprises a heavy chain constant region comprising the amino acid sequence set forth in SEQ ID NO: 1 and/or a light chain constant region comprising the amino acid sequence set forth in SEQ ID NO: 5.

In certain embodiments, the anti-ILT3 antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 13.

In certain embodiments, the anti-ILT3 antibody, or antigen binding portion thereof, comprises a heavy chain constant region comprising the amino acid sequence set forth in SEQ ID NO: 17 and/or a light chain constant region comprising the amino acid sequence set forth in SEQ ID NO: 20.

In certain embodiments, the anti-ILT3 antibody, or antigen binding portion thereof, comprises a heavy chain constant region comprising the amino acid sequence set forth in SEQ ID NO: 24 and/or a light chain constant region comprising the amino acid sequence set forth in SEQ ID NO: 27.

In certain embodiments, the anti-ILT3 antibody, or antigen binding portion thereof, comprises a heavy chain constant region comprising the amino acid sequence set forth in SEQ ID NO: 29 and/or a light chain constant region comprising the amino acid sequence set forth in SEQ ID NO: 32.

In certain embodiments, the anti-ILT3 antibody, or antigen binding portion thereof, comprises a heavy chain constant region comprising the amino acid sequence set forth in SEQ ID NO: 35 and/or a light chain constant region comprising the amino acid sequence set forth in SEQ ID NO: 38.

In certain embodiments, the anti-ILT3 antibody, or antigen binding portion thereof, comprises a heavy chain constant region comprising the amino acid sequence set forth in SEQ ID NO: 40 and/or a light chain constant region comprising the amino acid sequence set forth in SEQ ID NO: 44.

In certain embodiments, the anti-ILT3 antibody, or antigen binding portion thereof, comprises a heavy chain constant region comprising the amino acid sequence set forth in SEQ ID NO: 45 and/or a light chain constant region comprising the amino acid sequence set forth in SEQ ID NO: 49.

In certain embodiments, the anti-ILT3 antibody, or antigen binding portion thereof, comprises a heavy chain constant region comprising the amino acid sequence set forth in SEQ ID NO: 53 and/or a light chain constant region comprising the amino acid sequence set forth in SEQ ID NO: 57.

In certain embodiments, the anti-ILT3 antibody, or antigen binding portion thereof, comprises a heavy chain constant region comprising the amino acid sequence set forth in SEQ ID NO: 61 and/or a light chain constant region comprising the amino acid sequence set forth in SEQ ID NO: 65.

In certain embodiments, the anti-ILT3 antibody, or antigen binding portion thereof, comprises a heavy chain constant region comprising the amino acid sequence set forth in SEQ ID NO: 68 and/or a light chain constant region comprising the amino acid sequence set forth in SEQ ID NO: 72.

In certain embodiments, the anti-ILT3 antibody, or antigen binding portion thereof, comprises a heavy chain constant region comprising the amino acid sequence set forth in SEQ ID NO: 74 and/or a light chain constant region comprising the amino acid sequence set forth in SEQ ID NO: 78.

In certain embodiments, the anti-ILT3 antibody, or antigen binding portion thereof, comprises a heavy chain constant region comprising the amino acid sequence set forth in SEQ ID NO: 79 and/or a light chain constant region comprising the amino acid sequence set forth in SEQ ID NO: 80.

In certain embodiments, the anti-ILT3 antibody, or antigen binding portion thereof, comprises a heavy chain constant region comprising the amino acid sequence set forth in SEQ ID NO: 81 and/or a light chain constant region comprising the amino acid sequence set forth in SEQ ID NO: 84.

In certain embodiments, the anti-ILT3 antibody, or antigen binding portion thereof, comprises a heavy chain constant region comprising the amino acid sequence set forth in SEQ ID NO: 85 and/or a light chain constant region comprising the amino acid sequence set forth in SEQ ID NO: 89.

In certain embodiments, the anti-ILT3 antibody, or antigen binding portion thereof, comprises a heavy chain constant region comprising the amino acid sequence set forth in SEQ ID NO: 90 and/or a light chain constant region comprising the amino acid sequence set forth in SEQ ID NO: 94.

In certain embodiments, the anti-ILT3 antibody, or antigen binding portion thereof, comprises a heavy chain constant region comprising the amino acid sequence set forth in SEQ ID NO: 98 and/or a light chain constant region comprising the amino acid sequence set forth in SEQ ID NO: 100.

In certain embodiments, the anti-ILT3 antibody, or antigen binding portion thereof, comprises a heavy chain constant region comprising the amino acid sequence set forth in SEQ ID NO: 101 and/or a light chain constant region comprising the amino acid sequence set forth in SEQ ID NO: 100.

In certain embodiments, the anti-ILT3 antibody, or antigen binding portion thereof, comprises a heavy chain constant region comprising the amino acid sequence set forth in SEQ ID NO: 104 and/or a light chain constant region comprising the amino acid sequence set forth in SEQ ID NO: 100.

In certain embodiments, the anti-ILT3 antibody, or antigen binding portion thereof, comprises a heavy chain constant region comprising the amino acid sequence set forth in SEQ ID NO: 107 and/or a light chain constant region comprising the amino acid sequence set forth in SEQ ID NO: 100.

In certain embodiments, the anti-ILT3 antibody, or antigen binding portion thereof, comprises a heavy chain constant region comprising the amino acid sequence set forth in SEQ ID NO: 108 and/or a light chain constant region comprising the amino acid sequence set forth in SEQ ID NO: 100.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-ILT3 antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying ILT3 positive tumors. In a certain embodiment, anti-ILT3 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-ILT3 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-ILT3 antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-ILT3 antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 111-148 are used in the production of a recombinant antibody. The method can further comprise isolating the recombinant antibody from the culture medium.

III. Anti-ILT3 Antibody Drug Conjugates (ADCs)

Anti-ILT3 antibodies described herein may be conjugated to a drug moiety to form an anti-ILT3 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., ILT3 expressing tumors or ILT3 expressing cells. Thus, in certain embodiments, the disclosure provides anti-ILT3 ADCs for therapeutic use, e.g., treatment of cancer.

Anti-ILT3 ADCs comprise an anti-ILT3 antibody, i.e., an antibody that specifically binds to ILT3, linked to one or more drug moieties. The specificity of the ADC is defined by the specificity of the antibody, i.e., anti-ILT3. In one embodiment, an anti-ILT3 antibody is linked to one or more cytotoxic drug(s) which is delivered internally to a cancer cell expressing ILT3.

Examples of drugs that may be used in the anti-ILT3 ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

wherein Ab an anti-ILT3 antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing ILT3; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-ILT3 ADCs: Exemplary Drugs for Conjugation

Anti-ILT3 antibodies may be used in ADCs to target one or more drug(s) to a cell of interest, e.g., a cell expressing ILT3. The anti-ILT3 ADCs disclosed herein provide a targeted therapy that may, for example, reduce the side effects often seen with anti-cancer therapies, as the one or more drug(s) is delivered to a specific cell. In one embodiment, the drug used in an ADC is saporin. In another embodiment, the drug used in an ADC is dacarbazine. In another embodiment, the drug used in an ADC is carboplatin.

Examples of drugs that may be used in ADCs, i.e., drugs that may be conjugated to the anti-ILT3 antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-ILT3 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymrization). Thus, in one embodiment, an anti-ILT3 antibody of the invention is conjugated to one or more mitotic inhibitor(s) that disrupts microtubule formation by inhibiting tubulin polymerization. In another embodiment, an anti-ILT3 antibody of the invention is conjugated to one or more mitotic inhibitor(s) that stabilizes the microtubule cytoskeleton from deploymerization. In one embodiment, the mitotic inhibitor used in the ADCs of the invention is Ixempra (ixabepilone). Examples of mitotic inhibitors that may be used in the anti-ILT3 ADCs of the invention are provided below. Included in the genus of mitotic inhibitors are auristatins, described below.

a. Dolastatins

The anti-ILT3 antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-ILT3 ADC of the invention comprises an anti-ILT3 antibody, as described herein, and at least one dolastatin. Auristatins are synthetic derivatives of dolastatin 10.

b. Auristatins

Anti-ILT3 antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, anti-ILT3 antibodies are conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-ILT3 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

The structure of MMAE is provided below.

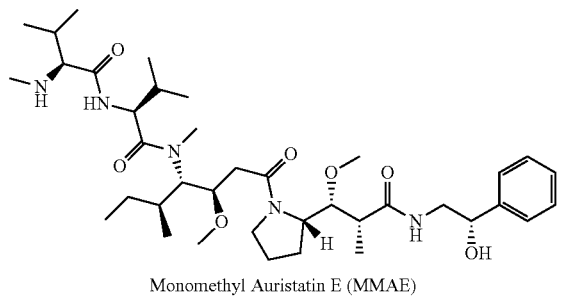 [SMILES: CC[C@H](C)[C@@H]([C@@H](CC(=O)N1CCC[C@H]1[C@H](OC)[C@@H](C)C(=O)NC[C@@H](O)c1ccccc1)OC)N(C)C(=O)[C@@H](NC(=O)[C@@H](NC)C(C)C)C(C)C]

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

c. Maytansinoids

The anti-ILT3 antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., *J. Med. Chem.*, 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

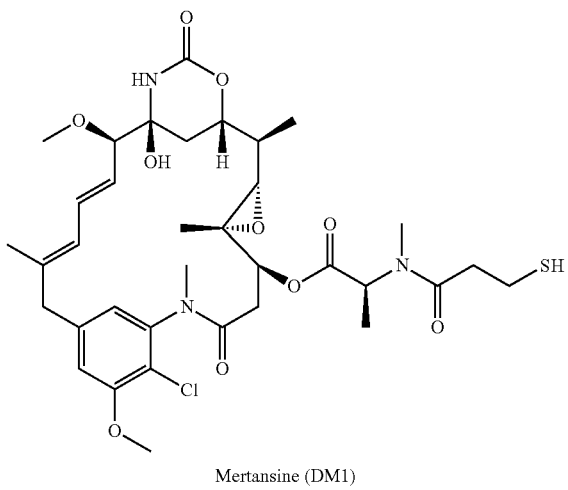

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) *Cancer Res* 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-ILT3 antibody is conjugated to at least one DM1. In one embodiment, an anti-ILT3 antibody is conjugated to at least one DM2. In one embodiment, an anti-ILT3 antibody is conjugated to at least one DM3. In one embodiment, an anti-ILT3 antibody is conjugated to at least one DM4.

2. Antitumor Antibiotics

Anti-ILT3 antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-ILT3 ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-ILT3 ADCs include bleomycin (Blenoxane, Bristol-Myers Squibb), mitomycin, and plicamycin (also known as mithramycin).

3. Immunomodulating Agents

In one aspect, anti-ILT3 antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-ILT3 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-ILT3 ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-ILT3 antibody is conjugated to at least one cancer vaccine that is either an immunostimulator or is an immunosuppressant.

The anti-ILT3 antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-ILT3 antibody described herein and a cytokine.

The anti-ILT3 antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-ILT3 ADCs include, but are not limited to erythropoietin (Epoetin), filgrastim (Neopogen (also known as granulocyte colony-stimulating factor (G-CSF); Amgen, Inc.), sargramostim (leukin (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-ILT3 antibody described herein and a CSF.

4. Alkylating Agents

The anti-ILT3 antibodies may be conjugated to one or more alkylating agent(s). Alkylating agents are a class of antineoplastic compounds that attaches an alkyl group to DNA. Examples of alkylating agents that may be used in the ADCs include, but are not limited to, pyrrolobenzodiazepines or PBDs, alkyl sulfonates, ethylenimimes, methylamine derivatives, epoxides, nitrogen mustards, nitrosoureas, triazines and hydrazines.

DNA Alkylating Agents

The term "DNA alkylating agent", as used herein, includes a family of DNA alkylating agents including indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics*, 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

DNA alkylating agents also include pyrrolobenzodiazepines or PBDs, a class of natural products with antibiotic or anti-tumor properties, which are produced by various actinomycetes (a broad group of bacteria that form thread-like filaments in the soil). PBDs are a family of sequence-selective DNA minor-groove binding agents that form a covalent aminal bond between their C11-position and the C2-NH2 groups of guanine bases. As a class of DNA-crosslinking agents, they are significantly more potent than systemic chemotherapeutic drugs. As DNA minor groove binding agents, pyrrolobenzodiazepines bind and cross-link specific sites of DNA of the cancer cell, blocking cancer cell division without distorting its DNA helix, thus potentially avoiding the common phenomenon of emergent drug resistance.

The first example of a PBD monomer, the natural product anthramycin, was discovered in the 1960s, and the best known PBD dimer, SJG-136 (also known as SG2000, NSC 694501 or BN2629), was synthesized in the 1990s and has recently completed Phase II clinical trials in patients with leukaemia and ovarian cancer. Other agents belonging to the pyrrolo(1,4)benzodiazepine antibiotic group include abbeymycin, chicamycin, DC-81, mazethramycin, neothramycins A and B, porothramycin prothracarcin, sibanomicin (DC-102) sibiromycin and tomamycin.

Dimeric pyrrolobenzodiazepines can be used as the cytotoxic drug payloads in antibody-drug conjugates, including vadastuximab talirine (Seattle Genetics), which is being developed for the treatment of patients acute myeloid leukemia (AML), and rovalpituzumab tesirine. Kolltan Pharmaceuticals and Genentech/Roche are developing antibody-drug conjugates with pyrrolobenzodiazepine as the cytotoxic drug payload. Kolltan Pharmaceuticals' preclinical agent, KTN0182A, is an anti-KIT, PBD-containing antibody-drug conjugate which demonstrated potent anti-tumor activity in vitro and in vivo against a broad range of tumor types. ADCs conjugated with PBD are also described in, for example, Rios-Doria, J. et al. (2017) *Cancer Res.* 77(10); 2686 and Mantaj, J. et al. (2017) *Angew Chem Int Ed Engl.* January 9; 56(2): 462-488, the contents of which are incorporated herein by reference.

5. Antiangiogenic Agents

In one aspect, the anti-ILT3 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initi-

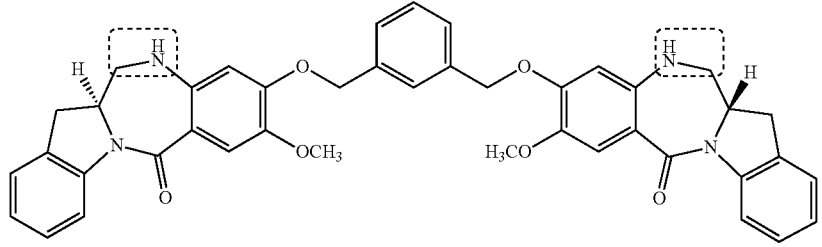

ating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α1b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

6. Antimetabolites

The anti-ILT3 antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7. Boron-Containing Agents

The anti-ILT3 antibody may be conjugated to at least one boron containing agent. Boron-containing agents comprise a class of cancer therapeutic compounds which interfere with cell proliferation. Representative examples of boron containing agents include, but are not limited to, borophycin and bortezomib (Velcade, Millenium Pharmaceuticals).

8. Chemoprotective Agents

The anti-ILT3 antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

9. Photoactive Therapeutic Agents

The anti-ILT3 antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-ILT3 antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt $^{109}$Pd, $^{105}$Rh$^{142}$pr, $^{143}$pr, $^{161}$Tb $^{66}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-ILT3 antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-ILT3 antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

13. Tyrosine Kinase Inhibitors

The anti-ILT3 antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-ILT3 ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-ILT3 antibodies described herein. In one embodiment, anti-ILT3 antibodies or ADCs are used with any of the foregoing agents in a combination therapy to treat cancer, where the agent is administered prior to, at the same time as, or following administration of the anti-ILT3 antibody or ADC to the subject.

B. Anti-ILT3 ADCs: Exemplary Linkers

An anti-ILT3 ADC comprises an anti-ILT3 antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components.

For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in ILT3-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-ILT3 ADCs described herein is a non-cleavable linker that promotes cellular internalization.

In some embodiments, the ADC has the following formula (formula I):

or a pharmaceutically acceptable salt or solvate thereof; wherein Ab is the antibody, e.g., anti-ILT3 antibody, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing ILT3; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the –D moieties are the same. In yet another embodiment, the –D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Another approach for the generation of ADCs involves the use of heterobifunctional cross-linkers which link the anti-ILT3 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-ILT3 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfo-succinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-ILT3 antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-ILT3 Antibodies and Anti-ILT3 ADCs

The antibodies and antibody portions (and ADCs) preferably are capable of neutralizing human ILT3 activity both in vivo and in vitro. Accordingly, such antibodies and antibody portions can be used to inhibit hILT3 activity, e.g., in a cell culture containing hILT3, in human subjects or in other mammalian subjects having ILT3 with which an antibody disclosed herein cross-reacts. In one embodiment, the disclosure provides a method for inhibiting hILT3 activity comprising contacting hILT3 with an antibody or antibody portion such that hILT3 activity is inhibited. For example, in a cell culture containing, or suspected of containing hILT3, an antibody or antibody portion can be added to the culture medium to inhibit hILT3 activity in the culture.

In another embodiment, disclosed herein is a method for reducing hILT3 activity in a subject, advantageously from a subject suffering from a "ILT3 associated disorder", e.g., cancer such as TNBC, or an inflammatory disorder such as PVNS, or a disorder in which ILT3 activity is detrimental. An "ILT3 associated disorder," as used herein, also includes a disorder characterized by infiltration of cells expressing ILT3, e.g., tumor infiltrating immune cells or myeloid derived suppressor cells (MDSCs).

The disclosure provides methods for reducing ILT3 activity in a subject suffering from such a disease or disorder, which method comprises administering to the subject an antibody or antibody portion of the disclosure such that ILT3 activity in the subject is reduced. Preferably, the ILT3 is human ILT3, and the subject is a human subject. Alternatively, the subject can be a mammal expressing a ILT3 to which antibodies of the disclosure are capable of binding. Still further the subject can be a mammal into which ILT3 has been introduced (e.g., by administration of ILT3 or by expression of a ILT3 transgene). Antibodies of the disclosure can be administered to a human subject for therapeutic purposes. Moreover, antibodies of the disclosure can be administered to a non-human mammal expressing a ILT3 with which the antibody is capable of binding for veterinary purposes or as an animal model of human disease. Regarding the latter, such animal models may be useful for evaluating the therapeutic efficacy of antibodies of the disclosure (e.g., testing of dosages and time courses of administration).

As used herein, the term "a disorder in which ILT3 activity is detrimental" is intended to include diseases and other disorders in which the presence of ILT3 in a subject suffering from the disorder has been shown to be or is suspected of being either responsible for the pathophysiology of the disorder or a factor that contributes to a worsening of the disorder. Accordingly, a disorder in which ILT3 activity is detrimental is a disorder in which reduction of ILT3 activity is expected to alleviate the symptoms and/or progression of the disorder. Such disorders may be evidenced, for example, by an increase in the concentration of ILT3 in a biological cell, fluid or tissue of a subject suffering from the disorder (e.g., an increase in the concentration of ILT3 in a tumor, serum, plasma, synovial fluid, etc. of the subject), or by infiltration of cells expressing ILT3, e.g., tumor infiltrating immune cells or myeloid derived suppressor cells (MDSCs), which can be detected, for example, using an anti-ILT3 antibody as described above.

Non-limiting examples of disorders that can be treated with the antibodies, or antigen binding fragments thereof, include those disorders discussed below. For example, suitable disorders include, but are not limited to, a variety of cancers including, but not limited to, triple negative breast cancer (TNBC) and acute myeloid leukemia (AML), and inflammatory disorders such as PVNS.

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor, B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. Acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-ILT3 ADC of the present invention can be used to treat a cancer in a subject including, but not limited to Hodgkin's lymphoma, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarial serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma, kidney renal clear cell carcinoma, and kidney renal papillary cell carcinoma.

In one embodiment, the antibodies and ADCs disclosed herein are used to treat a solid tumor, e.g., inhibit growth of or decrease size of a solid tumor, overexpressing ILT3 or which is ILT3 positive. In one embodiment, the antibodies and ADCs disclosed herein are used to treat triple negative breast cancer (TNBC). Diseases and disorders described herein may be treated by anti-ILT3 antibodies or ADCs, as well as pharmaceutical compositions comprising such anti-ILT3 antibodies or ADCs.

In certain embodiments, the antibodies and ADCs disclosed herein are administered to a subject in need thereof in order to treat advanced solid tumor types likely to exhibit elevated levels of ILT3. In certain embodiments, the disclosure includes a method for inhibiting or decreasing solid tumor growth in a subject having a solid tumor, said method comprising administering an anti-ILT3 antibody or ADC described herein, to the subject having the solid tumor, such that the solid tumor growth is inhibited or decreased. In certain embodiments, the solid tumor is a triple negative breast cancer (TNBC) tumor. In further embodiments, the solid tumor is an ILT3 expressing solid tumor. In certain embodiments the anti-ILT3 antibodies or ADCs described herein are administered to a subject having triple negative breast cancer (TNBC) or acute myeloid leukemia (AML), alone or in combination with one or more additional agent, e.g., radiation and/or chemotherapy, or one or more immune checkpoint inhibitor.

In certain embodiments, the disclosure includes a method for inhibiting or decreasing solid tumor growth in a subject having a solid tumor which was identified as an ILT3 expressing or ILT3 expressing tumor, said method comprising administering an anti-ILT3 antibody or ADC described herein, to the subject having the solid tumor, such that the solid tumor growth is inhibited or decreased. Methods for identifying ILT3 expressing tumors are known in the art, and include FDA-approved tests and validation assays. For example, these assays may use primers that are specific for the ILT3 gene and/or cDNA and result in the amplification of the ILT3 gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a ILT3-associated disorder, in a subject. The method includes: administering to the subject an ILT3 binding agent (particularly an antagonist), e.g., an anti-ILT3 antibody or fragment thereof as described herein, in an amount sufficient to treat or prevent the ILT3-associated disorder. The ILT3 antagonist, e.g., the anti-ILT3 antibody or fragment thereof, can be administered to the subject, alone or in combination with other therapeutic modalities as described herein.

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more ILT3 antagonists, e.g., anti-ILT3 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-ILT3 antibodies disclosed herein are used in combination with an anti-cancer agent or an antineoplastic agent. The terms "anti-cancer agent" and "antineoplastic agent" refer to drugs used to treat malignancies, such as cancerous growths.

In one embodiment, the anti-ILT3 antibodies or ADCs of the invention are administered in combination with one or more immune checkpoint inhibitors (e.g., antibody or small molecule immune checkpoint inhibitors) for the treatment of a cancer. In some embodiments, the immune checkpoint inhibitor is an inhibitor (e.g, an antibody) of Programmed Death-Ligand 1 (PD-L1, also known as B7-H1, CD274), Programmed Death 1 (PD-1), CTLA-4, PD-L2 (B7-DC, CD273), LAG3, TIM3, 2B4, 4-1BB, A2aR, B7H1, B7H3, B7H4, BTLA, CD2, CD6 (itolizumab), CD27, CD28, CD30, CD38, CD39, CD40, CD47, CD70, CD73, CD80, CD86, CD166, CD137, CD160, CD166, CD200, CD200R1, CD226, CD276, CSF1R, DR3, GALS, GITR, HVEM, IDO1, IDO2, ICOS (inducible T cell costimulator), PSGL1, CLEC4A, KIR, LAG3, LAIR1, TREM2, LILRB1, LILRB2, LILRB3, LIGHT, MARCO (macrophage receptor with collageneous structure), PS (phosphatidylserine), OX-40, SLAM, SIRPA, CSF1R, CD47, SIRPA, TIGHT, TIM3, TGFβ, VISTA, VTCN1, or any combinations thereof.

In some embodiments, the immune checkpoint inhibitor is an anti-CTLA-4, PD-L1, or PD-1 antibody therapy such as, but not limited to Yervoy® (ipilimumab Bristol-Myers Squibb), Opdivo® (nivolumab; Bristol-Myers Squibb), Keytrada® (pembrolizumab; Merck), and Tecentriq® (atezolizumab; Roche).

In other embodiments, the immune checkpoint inhibitor is an anti-CD38 antibody therapy such as isatuximab (Sanofi), Darzalex® (daratumumab; Genmab A/S and Janssen Biotech), MOR202 (MorphoSys AG), and Tusk Therapeutics Ltd.'s anti-CD38 monoclonal antibody.

In one embodiment, the anti-ILT3 antibodies or ADCs of the invention are administered in combination with one checkpoint inhibitor, e.g., an anti-CTLA-4, CD38, PD-L1, or PD-1 antibody. In other embodiments, the anti-ILT3 antibodies or ADCs of the invention are administered in combination with more than one checkpoint inhibitor, e.g., an an anti-ILT3 antibody or ADC of the invention in combination with an anti-CD38 antibody and an anti-PD-L1 antibody, or an anti-ILT3 antibody or ADC of the invention in combination with an anti-CD38 antibody and an anti-PD-1 antibody.

In some embodiments, the checkpoint inhibitor is an antibody currently undergoing clinical testing, including, for example, IDO (Epacadostat and Indoximod and BMS-986205), 4-1BB/CD137 (Utomilumab and Urelumab), KIR (Lirilulmab), CD40 (CP-870,893), CD27 (Varlilumab), LAG-3 (Relatilimab), MHCII (Eftilagimod Alpha).

In one embodiment, the anti-ILT3 antibodies or ADCs of the invention are administered in combination with one checkpoint inhibitor, e.g., an anti-CTLA-4, CD38, PD-L1, or PD-1 antibody. In other embodiments, the anti-ILT3 antibodies or ADCs of the invention are administered in combination with more than one checkpoint inhibitor, e.g., an an anti-ILT3 antibody or ADC of the invention in combination with an anti-CD38 antibody and an anti-PD-L1 antibody, or an anti-ILT3 antibody or ADC of the invention in combination with an anti-CD38 antibody and an anti-PD-1 antibody.

Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

In particular embodiments, the anti-ILT3 antibodies or ADCs can be administered alone or with another anti-cancer agent which acts in conjunction with or synergistically with the antibody to treat the disease associated with ILT3 activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the invention, the anti-ILT3 antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-ILT3 antibodies and ADCs described herein are administered in combination with a NAMPT inhibitor for the treatment of cancer in a subject.

In particular embodiments, the anti-ILT3 antibodies or ADCs described herein can be used in a combination therapy with SN-38, which is the active metabolite of the topoisomerase inhibitor irinotecan.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of ILT3 in a sample in vitro (e.g., a biological sample, such as serum, plasma, tissue, biopsy). The subject method can be used to diagnose a disorder, e.g., a cancer. The method includes: (i) contacting the sample or a control sample with the anti-ILT3 antibody or fragment thereof as described herein; and (ii) detecting formation of a complex between the anti-ILT3 antibody or fragment thereof, and the sample or the control sample, wherein a statistically significant change in the formation of the complex in the sample relative to the control sample is indicative of the presence of ILT3 in the sample.

Given their ability to bind to human ILT3, the anti-human ILT3 antibodies, or portions thereof, (as well as ADCs thereof) can be used to detect human ILT3 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human ILT3 in a biological sample comprising contacting a biological sample with an antibody, or antibody portion, and detecting either the antibody (or antibody portion) bound to human ILT3 or unbound antibody (or antibody portion), to thereby detect human ILT3 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$ $^{14}C$, S, $^{90}Y$ $^{99}Tc$, $^{111}In$, $^{125}I$, $^{131}$, $^{177}Lu$, $^{166}Ho$, or $^{153}Sm$.

Alternative to labeling the antibody, human ILT3 can be assayed in biological fluids by a competition immunoassay utilizing rhILT3 standards labeled with a detectable substance and an unlabeled anti-human ILT3 antibody. In this assay, the biological sample, the labeled rhILT3 standards and the anti-human ILT3 antibody are combined and the amount of labeled rhILT3 standard bound to the unlabeled antibody is determined. The amount of human ILT3 in the biological sample is inversely proportional to the amount of labeled rhILT3 standard bound to the anti-ILT3 antibody. Similarly, human ILT3 can also be assayed in biological fluids by a competition immunoassay utilizing rhILT3 standards labeled with a detectable substance and an unlabeled anti-human ILT3 antibody.

In yet another aspect, this application provides a method for detecting the presence of ILT3 in vivo (e.g., in vivo imaging in a subject). The subject method can be used to diagnose a disorder, e.g., a ILT3-associated disorder. The method includes: (i) administering the anti-ILT3 antibody or fragment thereof as described herein to a subject or a control subject under conditions that allow binding of the antibody or fragment to ILT3; and (ii) detecting formation of a complex between the antibody or fragment and ILT3, wherein a statistically significant change in the formation of the complex in the subject relative to the control subject is indicative of the presence of ILT3.

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which ILT3 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1. Immunohistochemical Analysis of ILT3 in TNBC Tissues

Triple-negative breast cancer (TNBC) tumors, formalin fixed and embedded in paraffin, were sectioned and mounted on microscope slides. Expression and cellular localization of ILT3 was evaluated using standard immunohistochemistry methodology.
Methods
Immunohistochemistry (IHC)
TNBC tumor sections were stained with antibodies against ILT3 (R&D Systems, Minneapolis, MN) and the myeloid marker CD68 (Dako, Santa Clara, CA), using standard IHC procedure. Briefly, paraffin embedded tissues were mounted on slides and were deparrafinized by incubating with xylene, 100% ethanol and 95% ethanol, followed by rehydration with deionized water. Antigen unmasking was achieved by heating slides in a microwave submersed in 1× citrate unmasking solution until boiling was initiated, followed by cooling at room temperature for 30 minutes. Sections were blocked in 1×TBST/5% normal goat serum for 1 hour and then subsequently incubated with the anti-ILT3 or anti-CD68 primary antibody overnight at 4° C. A secondary reagent conjugated with horseradish peroxidase (HRP) recognizing goat immunoglobulins or mouse immunoglobulins was used to visualize ILT3 or CD68 staining, respectively. Counterstain using hematoxylin was done using manufacturer's instructions (Cell Signaling Technology, Danvers, MA).
Results
Expression of ILT3 was confirmed in TNBC tissue sections. The IHC staining revealed that ILT3 was predominantly expressed by the tumor infiltrating immune cells, which also expressed CD68 in serial section stains. These data are in line with previous published observations that ILT3 is expressed by infiltrating CD68+ myeloid cells in solid tumors (Suciu-Foca, N. et al., *J. Immunol.*, 2007, 178, 7432-7441).

Example 2. Generation of Fully Human Antibodies Against Human ILT3

Experiments were performed to generate fully human antibodies against human ILT3 using the following methods.
Methods
DNA Immunizations in Humanized Mice
Humanized mice were immunized using a standard DNA prime with recombinant protein boost method. Human ILT3 cDNA construct was purchased from Origene™ (Rockville, MD). Large scale DNA preparation of the ILT3 construct was performed using standard plasmid expansion methods. Twelve week old H2L2 mice were anesthetized and then received an intramuscular injection in the tibialis anterior muscle, containing 50 µg of ILT3 plasmid DNA in a 50 µL volume. Immediately following, the injected area was subjected to in vivo electroporation using a BTX 830™ generator and a BTX™ 7 mm diameter tweezertrode electrode (BTX Harvard Apparatus, Holliston, MA) under the following conditions: 100 V/cm, 20 ms, 460 ms between pulses. Mice received a total of 3 DNA immunizations spaced by 1 week. Mice that showed anti-ILT3 serum activity after the $3^{rd}$ DNA immunization were rested for one month and boosted twice with 50 µg of ILT3 recombinant protein (#16742-H08-H-20, Sino Biological Inc, Beijing, China) intravenously. Protein boosts were spaced by 2 weeks. A final recombinant protein boost was given 3-5 days prior to sacrificing the animals. Spleens were taken immediately for fusions.
Cell Fusion
Cell fusion was done following a standard hybridoma procedure. Briefly, one week before the cell fusion, the fusion partner mouse myeloma cell line X63-Ag8.653 (#85011420, non-Ig-secreting; Sigma-Aldrich, St. Louis, MO) was cultured in complete RPMI 1640 medium (2 mM Glutamine and 20% Fetal Bovine Serum, FBS). Spleens from the immunized mice were mechanically processed and made into single-cell suspensions. The cell suspension was passed through a fine mesh 100 µm nylon filter and transferred to a sterile 50 mL conical tube full of serum-free RPMI 1640 medium. The splenocytes were pelleted by centrifuging for 5 min at 1500 rpm (500×g) at room temperature. Supernatant was discarded and the cell pellet was resuspended with 5 mL of ammonium chloride solution for 5 minutes at room temperature to lyse red blood cells (RBC). Cell suspension was washed twice with serum-free RPMI and then cell number and viability was determined using a hemocytometer. Concurrently, X63-Ag8.653 myeloma cells were harvested by transferring the cells from their culture vessels to a 50 mL conical tube and washed two times with serum free RPMI followed by cell count and viability assessment. The X63-Ag8.653 myeloma cells and the mouse splenocytes were mixed at a 1:10 ratio, respectively, in a 50 mL conical tube and then spun down for 5 min at 1500 rpm (500×g).

The cell fusion was performed by placing the tube containing the mixed cell pellet in a 37° C. water bath under sterile conditions. The mixed cell pellet received 1 mL of pre-warmed 50% PEG solution (Sigma-Aldrich, St. Louis, MO) in dropwise fashion over a 1-minute time period, with constant stirring after every drop. The cell mixture then received 1 mL of pre-warmed serum free RPMI, added dropwise for 1 minute, followed by 1 mL of complete RPMI added in a similar fashion. Cells were constantly stirred after every drop of serum free or complete RPMI media. In similar dropwise fashion, 7 mL of pre-warmed serum-free RPMI was added to the cells over a period of 3 minutes. The cells were then centrifuged for 5 min at 1500 rpm at room temperature and the cell pellet was thoroughly resuspended with 20 mL of pre-warmed complete RPMI. The cell suspension was then transferred to a sterile reservoir container and 200 µL of cell suspension was collected with a multi-channel pipet and transferred to 96-well flat bottom plates until the entire cell suspension was plated (yielded about 10 plates). The fused cells were kept in a humidified incubator at 37° C. with 5% $CO_2$. On the second day, complete RPMI media was supplemented with 1×HAT (Sigma-Aldrich, St. Louis, MO) reagent and distributed to the 10 fusion plates. The fused cells were fed by removing 50% of the original culture media and replacing it with new HAT+ media on culture days 6, 7, and 10. After 12 days in culture, fusion supernatants were evaluated for anti-ILT3 activity using high-throughput assays.

Immunofluorescence (IF) Based High Content Screening (HCS)

High content immunofluorescence was used to identify wells that contain immunoglobulin that preferentially bound ILT3. Briefly, ILT3 was ectopically expressed in the Human Embryonic Kidney 293 (HEK293) cell line, which were then used to identify wells containing anti-ILT3 immunoglobulins. Parental HEK293 cells, transfected with an empty DNA vector, were used to identify non-specific antibodies. These cells were seeded 24 hours before the assay and then were incubated for 45 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton-X-100, and labeled with anti-rat Alexa 488 secondary antibodies for 1 hour at room temperature. Unbound secondary antibody was removed with PBS washes, and cells were stained with propidium iodide (PI) and Hoechst 33342 to identify cell nucleus.

Potential hits were initially identified via low-resolution, high-throughput screening using a TTP Labtech Acumen eX3™ (TTP Labtech, Cambridge, MA), quantifying the fluorescence differential for each sample on both positive and negative cell lines. Those hits were subsequently verified and the subcellular localization of each sample was characterized using a Thermo ArrayScan VTi™ (Thermo Fisher Scientific, Waltham, MA) to obtain high-resolution images of both cell lines.

Wells containing immunoglobulin that preferentially bound human ILT3 were subsequently evaluated, using a flow cytometry based method, for their recognition of endogenous human ILT3 and the *Macaca fascicularis* ILT3 homologue, which was over-expressed on HEK293 cells.

Flow Cytometry

Supernatant from hybridoma wells, containing ILT3 specific antibodies, were re-tested on human acute myeloid leukemia cell lines KG1 (ILT3⁻) and MV4-11 (ILT3⁺), which have been described as lacking or expresing endogenous ILT3 on their cell surface (Dobrowolska, H. et al. Cytometry Part B: Clinical Cytometry. 2013; 84B, 21-29). KG1 and MV4-11 cell lines were collected from their respective culture vessels and transferred to 50 mL conical tubes. The cells were pelleted by centrifuging them for 5 minutes at 1250 rpm at room temperature. The cell pellets were washed 2 times with flow buffer (1×PBS, 0.5% BSA, 2 mM EDTA). After the second wash, the cells were counted and the concentration was adjusted to $1 \times 10^6$ cells per 1 mL. The KG1 and MV4-11 cell suspensions were mixed and transferred to a sterile reservoir container. Using a multi-channel pipette, 200 µL was collected and transferred to 96-V bottom polypropylene plates and spun at 1250 rpm for 5 min at 4° C. to pellet the cells. The cell pellets were resuspended with hybridoma supernatant diluted 2-fold with cold flow buffer and incubated at 4° C. for 30 min. After incubation, cells were washed 2× with flow buffer and then labeled with anti-rat Alexa 647 secondary antibodies for 30 min at 4° C. Unbound secondary antibodies were removed by washing the cells 2× with flow buffer. Cells were then resuspended in 200 µL of flow buffer containing PI to identify dead cells and remove from analysis. This procedure was replicated when evaluating anti-macaque ILT3 reactivity with the HEK293 system. Cells were run on a MACSQuant Analyzer 10™ flow cytometer (Miltenyi Biotec, Bergisch Gladbach, Germany) and analysis was performed with FlowJo™ software (FlowJo, Ashland, OR).

Recombinant ILT3 Cloning

Ectodomains of human and cynomolgus monkey were cloned by synthetic genes. The synthetic genes were based on GenBank sequences: human (AAH26309.1) (SEQ ID NO: 149) and monkey (XP_015297200). All DNA sequences were cloned into appropriate CMV-based expression vectors with non-native signal peptides and C-terminal histidine tags for purification.

Cloning VH and VL Sequences from Hybridomas

For determination of CDR sequences, total RNA was isolated from hybridoma cells using an RNeasy® kit (Qiagen, Hilden, Germany). First and second-strand cDNA synthesis was performed using a One Taq® One-Step RT-PCR kit (New England BioLabs, Ipswich, MA). Several primer sets were used (see Table 1). PCR products were separated by agarose electrophoresis and fragments were excised and purified by a QIAquick® gel extraction kit (Qiagen, Hilden, Germany). Fragments were cloned directly into expression vectors with BspQI (New England BioLabs, Ipswich, MA) by Golden Gate cloning techniques. Four colonies from each reaction were scaled up for miniprep-scale plasmid purification by SequeMid® DNA Purification Kit (Aline Biosciences, Woburn, MA).

TABLE 1

Oligonucleotide Sequences

| SEQ ID NO | Oligonucleotide Sequence | Oligonucleotide Purpose |
|---|---|---|
| 150 | ATAGCTCTTCAGGGaccATGAARCAYCTGTGGTTCTTCCT | IGHV4 leader |
| 151 | ATAGCTCTTCAGGGaccATGGACATACTTTGTTCCACGC | IGHV2 leader |
| 152 | ATAGCTCTTCAGGGaccATGGACACACTTTGCTACACAC | IGHV2-26 leader |
| 153 | ATAGCTCTTCAGGGaccATGTCTGTCTCCTTCCTCATCT | IGHV6 leader |
| 154 | ATAGCTCTTCAGGGaccATGGACTGGACCTGGAGVATC | IGHV1 leader |
| 155 | ATAGCTCTTCAGGGaccATGGACTGGATTTGGAGGRTC | IGHV1-58 leader |
| 156 | ATAGCTCTTCAGGGaccATGGACTGCACCTGGAGGATC | IGHV1-24 leader |
| 157 | ATAGCTCTTCAGGGaccATGGACTGGACCTGGAGGKTC | IGHV1-69/1-46/7-4-1 leader |
| 158 | ATAGCTCTTCAGGGaccATGGAGTTKGGRCTGAGCTGG | IGHV3 leader |
| 159 | ATAGCTCTTCAGGGaccATGGAGTTTKGGCTKAGCTGG | IGHV3-53/3-49 leader |
| 160 | ATAGCTCTTCAGGGaccATGGAACTGGGGCTCCGCTGG | IGHV3-21 leader |
| 161 | ATAGCTCTTCAGGGaccATGGARTTGGGGCTGWGCTGG | IGHV3-48/3-7 leader |
| 162 | ATAGCTCTTCAGGGaccATGGGGTCAACCGCCATCCTC | IGHV5 leader |
| 163 | ATAGCTCTTCAGGGaccATGGACATGAGGGTSCCYGCTCAGCTC | IgkV1a leader |
| 164 | ATAGCTCTTCAGGGaccATGGACATGAGRGTCCTCGCTCAGCTC | IgkV1b leader |
| 165 | ATAGCTCTTCAGGGaccATGGAAGCCCCAGCDCAGCTTCTC | IgkV3 leader |
| 166 | ATAGCTCTTCAGGGaccATGGAAACCCCAGCGCAGCTTCTC | IgkV3-20 leader |
| 167 | ATAGCTCTTCAGGGaccATGGTGTTGCAGACCCAGGTCTTC | IgkV4 leader |
| 168 | ATAGCTCTTCAGGGaccATGGGGTCCCAGGTTCACCTCCTC | IgkV5 leader |
| 169 | ATAGCTCTTCAGGGaccATGAGGCTCCYTGCTCAGCTCCTG | IgkV2 leader |
| 170 | ATAGCTCTTCTTCGTTTGATCTCCASCTTGGTC | Kappa FW4 |
| 171 | ATAGCTCTTCTTCGTTTAATCTCCAGTCGTGTC | Kappa FW4 |
| 172 | ATAGCTCTTCTGGCTGAGGAGACGGTGACC | Heavy FW4 |
| 173 | ATAGCTCTTCATGTGACGCTGTTGTGACTCAGGA | VL-FOR L1 |
| 174 | ATAGCTCTTCATGTGACCYTGTGCTCACTCAGTC | VL-FOR L2 |
| 175 | GATGCTCTTCTGGGCTGGCCTAGGACAGTCAMCYTGG | VL-REV L |

Identification of Functional, Recombinant VH and VL Sequences

For each hybridoma, each plasmid was sent for Sanger Sequencing. These plasmids were subjected to DNA sequence determination and analysis.

For each hybridoma, unique recombinant heavy chains were paired with unique recombinant light chains. These plasmid pairs were transfected into CHO cells in 24-well plates. Ten days later conditioned medium from each pairing was screened by Flow cytometric analysis or Octet for binding to the target.

Transient Expression System

The ILT3 recombinant proteins and anti-ILT3 antibodies were expressed in Chinese hamster ovary (CHO) cells using recommended transfection and media components of the ExpiCHO™ system (Invitrogen, Carlsbad, CA). Cell culture supernatants were harvested 14 days post-transfection, centrifuged, and filtered (0.22 um).

Purification of Recombinant His-Tagged Proteins

Conditioned medium from CHO cell cultures was clarified, filtered, and loaded onto an ÄKTAprime Plus™ system with a 5 mL HisTrap™ FF column (GE Healthcare). Fractions were collected, analyzed by SDS-PAGE, pooled, and dialyzed against PBS.

Antibody Purification

Conditioned medium from CHO cell cultures was clarified, filtered, and purified by loading onto an AKTA pure system with a 5 mL MabSelect SuRe® column (GE Healthcare). Antibodies were eluted with 100 mM glycine, pH 3.5 and neutralized with 1 M Tris-C1, pH 8.5.

Recombinant Antibody Analyses

Concentration: Concentration of recombinant antibodies was determined on a Fortebio Octet using Protein A tips and a human IgG1 antibody for the standard curve.

Purity testing by SDS-PAGE: Purity testing was performed by sodium dodecyl sulfate polyacrylamide gel electrophoresis (SDS-PAGE) of reduced and non-reduced samples. Samples (10 µg) were mixed with loading buffer (+/−β-mercaptoethanol), heated, and electrophoresed on a 4-20% gel (Invitrogen). Bands were visualized by Coomassie InstantBlue™ (Expedeon) staining.

Purity testing by Endotoxin: Endotoxin concentrations were measured by the Limulus amoebocyte lysate (LAL) kinetic turbidometric method using the Endosafe-PTS™ system (Charles River Laboratories).

Purity testing by HPLC-SEC: Samples were screened for aggregation or other forms of antibody on a 1260 Infinity System™ (Agilent) with a TSKgel UltraSW Aggregate Guard™ column and HPLC column (Tosoh Bioscience). Samples and standards were detected by absorbance at 280 nm. Comparison against the standard curve provided the molar mass of sample components.

Affinity: The affinity of antibodies to recombinant ILT3 was determined on an Octet Red™ (Pall, ForteBio) instrument. After loading reagents into a 96-well plate, the Octet Red™ with Protein A-conjugated biosensors was programmed as follows: 30 seconds for baseline #1; 45 seconds to immobilize the antibody; 30 seconds for baseline #2; 300 seconds for association of antibody to recombinant ILT3; and 300 seconds for dissociation of recombinant ILT3 from the antibody. In some cases, the antibody affinity was estimated against cynomolgus ILT3 using a flow based method. Briefly, the assay uses 3-5 fold dilutions from 100 nM to 0.1 nM of a stock antibody concentration (100 nM) diluted in flow buffer. Serial diluted antibodies were incubated with live cells on ice for 30 minutes, after 2 washes, cells were incubated with Alexa Fluro® 647-conjugated anti-human IgG secondary antibodies diluted 1:100, or 15 ug/ml (cat #709-606-149, Jackson ImmunoResearch). Acquisition of the MFI (Median Fluorescent Intensity) was performed on a MACSQuant® Flow Cytometers (Miltenyi Biotec).

EC50 was calculated using Dose-response EC50 shift by global fitting from GraphPad Prism.

Binding competition: Binding competition among different antibodies was determined using a real-time, interferometry assay on an Octet Red™ (Pall, ForteBio) instrument with Protein A-conjugated biosensors. To assess whether two antibodies competed for binding to a recombinant ILT3 protein, the assay was performed as follows. Protein A biosensors were first submerged into wells containing 20 µg/mL of individual monoclonal antibodies for 1 minute. Following the capture step, the biosensors were dipped briefly (30 seconds) into buffer and then any unoccupied sites on the biosensor were saturated by submerging them for 5 minutes into wells containing 200 µg/mL of an irrelevant polyclonal antibody. The Octet™ biosensors were then dipped briefly (30 seconds) in buffer before immersion for 1 minute into wells containing recombinant ILT3. The biosensors were dipped briefly (30 seconds) in buffer before immersion for 1 minute into wells containing a second recombinant antibody.

For the control case where the second antibody was the same as the first, there was no increase in signal, because there was no additional binding to the recombinant target.

For the control case where buffer was used instead of the first antibody, no recombinant target bound the non-quenching antibody on the biosensor and no second antibody bound the biosensor. For cases where a boost in signal was seen with the second antibody, the two antibodies were determined not to compete. For cases where no boost in signal was seen with the second antibody, the two antibodies were determined to compete for binding.

Results

Fully human antibodies against the extracellular domain (ECD) of ILT3 were generated by standard hybridoma procedures as described above. Primary screens of hybridoma supernatants revealed wells that contained antibodies specifically recognizing human ILT3 and the macaque ILT3 homologue. Fused cells in these wells were subcloned to yield monoclonal antibodies that were then sequenced and cloned into heavy and light chain expression plasmids.

Twenty-one human antibodies were identified. Complete amino acid sequences of the variable heavy and light chains from these twenty-one antibodies are set forth in Table 2, below. Nucleic acid sequences of the variable heavy and light chains are set forth below in Table 3. Note that antibodies 3D8D11, 3H3_24B2, 6B6_24B5, 8C7_24B1 and 4F4_27D3 share the same variable light chain sequence (the amino acid sequence set forth in SEQ ID NO:100).

TABLE 2

Variable Region Amino Acid Sequences of Human Antibodies

| SEQ ID NO: | Clone Name | Protein Domain | Protein Sequence |
|---|---|---|---|
| 1 | 1E2F12H8_3D2 | VH | EVQLLESGGGLVQPGGSLRLSCAASGFTFSSYAMSWVRQAPGKGLE WVSIISGSGGDTYYADSVKGRFTISRDNSKNTLYLQMNSLRAEDTA VYYCAKTDDHGDFFDYWGQGTLVTVSS |
| 2 | 1E2F12H8_3D2 | CDR-H1 | GFTFSSYAMS |
| 3 | 1E2F12H8_3D2 | CDR-H2 | IISGSGGDTYYADSVKG |
| 4 | 1E2F12H8_3D2 | CDR-H3 | TDDHGDFFDY |
| 5 | 1E2F12H8_3D2 | VL | DIQMTQSPSTLSASVGDRVTITCRASQSISSWLAWYQQKPGKAPKL LIYKASSLESGVPSRFSGSGSGTEFTLTISSLQPDDFATYYCQQYN SYWTFGQGTKVEIK |
| 6 | 1E2F12H8_3D2 | CDR-L1 | RASQSISSWLA |
| 7 | 1E2F12H8_3D2 | CDR-L2 | KASSLES |
| 8 | 1E2F12H8_3D2 | CDR-L3 | QQYNSYWT |

TABLE 2-continued

Variable Region Amino Acid Sequences of Human Antibodies

| SEQ ID NO: | Clone Name | Protein Domain | Protein Sequence |
|---|---|---|---|
| 9 | 1E12H10_7A1 | VH | QVQLVESGGGVVQPGRSLRLSCATSGFTFSSYGMHWVRQAPGKGLEWVALIWFDGGNQYYADSVKGRFTISRDNSKNTLYLQLNSLRAEDTAVYFCARDVISMVRGVPFDYWGQGTLVTVSS |
| 10 | 1E12H10_7A1 | CDR-H1 | GFTFSSYGMH |
| 11 | 1E12H10_7A1 | CDR-H2 | LIWFDGGNQYYADSVKG |
| 12 | 1E12H10_7A1 | CDR-H3 | DVISMVRGVPFDY |
| 13 | 1E12H10_7A1 | VL | DAVVTQESALTTSPGETVTLTCRSSTGAVTTGNYANWVQEKPDHLFTGLIGGIKNRVPGVPARFSGSLIGDRAALTITGAQTEDEAIYFCALWYSNHWVFGGGTKLTVLG |
| 14 | 1E12H10_7A1 | CDR-L1 | RSSTGAVTTGNYAN |
| 15 | 1E12H10_7A1 | CDR-L2 | GIKNRVP |
| 16 | 1E12H10_7A1 | CDR-L3 | ALWYSNHWV |
| 17 | 3C4A3_7C5 | VH | EVQLLESGGGLVQPGGSLRLSCAASGFTESSYAMSWVRQAPGKGLEWVSVISGSGGSTYYADSVKGRFTISRDNSKNTLDLQMNSLRAEDTAVYYCAKLGDYYYGMDVWGQGTTVTVSS |
| 2 | 3C4A3_7C5 | CDR-H1 | GFTFSSYAMS |
| 18 | 3C4A3_7C5 | CDR-H2 | VISGSGGSTYYADSVKG |
| 19 | 3C4A3_7C5 | CDR-H3 | LGDYYYGMDV |
| 20 | 3C4A3_7C5 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQAPWTFGQGTKLEIK |
| 21 | 3C4A3_7C5 | CDR-L1 | RSSQSLLHSNGYNYLD |
| 22 | 3C4A3_7C5 | CDR-L2 | LGSNRAS |
| 23 | 3C4A3_7C5 | CDR-L3 | MQALQAPWT |
| 24 | 8E11B6 | VH | QVQLEESGGGVVQPGRSLRLSCAASGFTFSSYGMHWVRQAPGKGLEWVAVIWYDGSNTYYADSVKGRFTISRDNSKNTLYLQMNSLRAEDTAVYYCARERETFFYVMDAWGQGASVTVSS |
| 10 | 8E11B6 | CDR-H1 | GFTFSSYGMH |
| 25 | 8E11B6 | CDR-H2 | VIWYDGSNTYYADSVKG |
| 26 | 8E11B6 | CDR-H3 | ERETFFYVMDA |
| 27 | 8E11B6 | VL | DIQMTQSPSTLSASVGDRVTITCRASQSISSWLAWYQQKPGKAPKLLIYKASSLESGVPSRFSGSGSGTEFTLTISSLQPDDFAIYYCQQFNRFITFGQGTRLEIK |
| 6 | 8E11B6 | CDR-L1 | RASQSISSWLA |
| 7 | 8E11B6 | CDR-L2 | KASSLES |
| 28 | 8E11B6 | CDR-L3 | QQFNRFIT |
| 29 | 17E8_27C5 | VH | QVQLVESGGGVVQPGRSLRLSCAASGFTFSNYGMHWVRQAPGKGLEWMAGIWFDGTNKYYIDSVKGRFTISRDNSKNTLYLQMNNLRAEDTAVYYCARDVISMVRGVPFDYWGQGTLVTVSS |
| 30 | 17E8_27C5 | CDR-H1 | GFTFSNYGMH |
| 31 | 17E8_27C5 | CDR-H2 | GIWFDGTNKYYIDSVKG |
| 12 | 17E8_27C5 | CDR-H3 | DVISMVRGVPFDY |
| 32 | 17E8_27C5 | VL | DAVVTQESALTTSPGETVTLTCRSSTGAVTTSNYANWVQEKPDHLFTGLIGGINNRAPGVPARFSGSLIGDKAALTITGAQTEDEAIYFCALWYSNHWVFGGGTKLTVLGQPKA |

TABLE 2-continued

Variable Region Amino Acid Sequences of Human Antibodies

| SEQ ID NO: | Clone Name | Protein Domain | Protein Sequence |
|---|---|---|---|
| 33 | 17E8_27C5 | CDR-L1 | RSSTGAVTTSNYAN |
| 34 | 17E8_27C5 | CDR-L2 | GINNRAP |
| 16 | 17E8_27C5 | CDR-L3 | ALWYSNHWV |
| 35 | 17E8_27C5 | VH | QVQLVESGGGVVQPGRSLRLSCAASGFTFSTYGIHWVRQAPGKGLE WVAVIWFDGSNKYYADSVKGRFTISRDNSKNTLYLQMNSLRAEDTA VYYCARDVISMVRGVPFDYWGQGTLVTVSS |
| 36 | 17F4_27C6 | CDR-H1 | GFTFSTYGIH |
| 37 | 17F4_27C6 | CDR-H2 | VIWFDGSNKYYADSVKG |
| 12 | 17F4_27C6 | CDR-H3 | DVISMVRGVPFDY |
| 38 | 17F4_27C6 | VL | DAVVTQESALTTSPGETVTLTCRSSTGAVTTSNYANWVQEKPDHLF TGLIGGINNRVPGVPARFSGSLIGDKAALTITGAQTEDEAIYFCAL WYSNHWVFGGGTKVTVLGQPKA |
| 33 | 17F4_27C6 | CDR-L1 | RSSTGAVTTSNYAN |
| 39 | 17F4_27C6 | CDR-L2 | GINNRVP |
| 16 | 17F4_27C6 | CDR-L3 | ALWYSNHWV |
| 40 | 11H10_27D4 | VH | QVQLVESGGGVVQPGRSLRLSCAASGFTFSNYGIHWVRQAPGKGLE WVAVIWFDGNNKYYADSVKGRFTISRDNSKNTLYLQMNSLRAEDTA VYYCARDVITLVRGVPFDYWGQGTLVTVSS |
| 41 | 11H10_27D4 | CDR-H1 | GFTFSNYGIH |
| 42 | 11H10_27D4 | CDR-H2 | VIWFDGNNKYYADSVKG |
| 43 | 11H10_27D4 | CDR-H3 | DVITLVRGVPFDY |
| 44 | 11H10_27D4 | VL | DAVVTQESALTTSPGETVTVTCRSSTGAVTTSNYANWVQEKPDHLF TGLIGGINNRAPGVPARFSGSLIGDKAALTITGAQTEDEAIYFCAL WYSNHWVFGGGTKLTVLGQPK |
| 33 | 11H10_27D4 | CDR-L1 | RSSTGAVTTSNYAN |
| 34 | 11H10_27D4 | CDR-L2 | GINNRAP |
| 16 | 11H10_27D4 | CDR-L3 | ALWYSNHWV |
| 45 | 1C4_24B3 | VH | QVQLQEAGPGLVNPSKTLSLTCTVSGGSISSYFWSWIRQPPGKGLE WIGYIYNSGSTNYNPSLQSRVTISVDMSKNHFSLKLSSVTAADTAV YYCARRGGYYGSGNYGGMDVWGQGTTVTVSS |
| 46 | 1C4_24B3 | CDR-H1 | GGSISSYFWS |
| 47 | 1C4_24B3 | CDR-H2 | YIYNSGSTNYNPSLQS |
| 48 | 1C4_24B3 | CDR-H3 | RGGYYGSGNYGGMDV |
| 49 | 1C4_24B3 | VL | DIQMTQSPSSLSASAGDRVTITCRASQGISNYLAWYQQKPGKVPKL LMYAASALQSGVPSRFSGSGSGTDFTLTISSLQPEDVATYYCQKYD SAPWTFGQGTKVEIK |
| 50 | 1C4_24B3 | CDR-L1 | RASQGISNYLA |
| 51 | 1C4_24B3 | CDR-L2 | AASALQS |
| 52 | 1C4_24B3 | CDR-L3 | QKYDSAPWT |
| 53 | 20H6_24C3 | VH | QVQLQESGPGLLKPSETLSLTCTVSGGSISPYYWSWIRQPPGKGLE WIGYIYYSGNTNYNPSLQSRLTISVDTSKNQFSLKLSSVTAADTAV YYCARRGYSFGFYYGLDVWGQGTTVTVSS |
| 54 | 20H6_24C3 | CDR-H1 | GGSISPYYWS |
| 55 | 20H6_24C3 | CDR-H2 | YIYYSGNTNYNPSLQS |
| 56 | 20H6_24C3 | CDR-H3 | RGYSFGFYYGLDV |

TABLE 2-continued

Variable Region Amino Acid Sequences of Human Antibodies

| SEQ ID NO: | Clone Name | Protein Domain | Protein Sequence |
|---|---|---|---|
| 57 | 20H6_24C3 | VL | DIQMTQSPSSLSASVGDRVTITCRASQDISIYLAWYQQKPGKVPNLLIYLASTLQSGVPSRFSGSGSGTDFTLTISSLQPEDVATYYCQKYNSAPWTFGQGTKLEIK |
| 58 | 20H6_24C3 | CDR-L1 | RASQDISIYLA |
| 59 | 20H6_24C3 | CDR-L2 | LASTLQS |
| 60 | 20H6_24C3 | CDR-L3 | QKYNSAPWT |
| 61 | 14E7_27C1 | VH | QVQLQESGPGLVKPSETLSLTCTVSGGSISSYYWSWIRQPPGKGLEWIGYIYYSGSTNYNPSLKSRLTISVDTSKNQFSLKLSSVTAADTAVYYCARRGYSYGYYYGMDVWGQGTTVTVSS |
| 62 | 14E7_27C1 | CDR-H1 | GGSISSYYWS |
| 63 | 14E7_27C1 | CDR-H2 | YIYYSGSTNYNPSLKS |
| 64 | 14E7_27C1 | CDR-H3 | RGYSYGYYYGMDV |
| 65 | 14E7_27C1 | VL | DIQMTQSPSSLSASVGDRVTITCRASQDISNYLAWYQQKPGKVPKLLISPASTLQSGVPSRFSGSGSGTDFTLTISSLQPEDVATYYCQKYNSAPWTFGQGTKLEIK |
| 66 | 14E7_27C1 | CDR-L1 | RASQDISNYLA |
| 67 | 14E7_27C1 | CDR-L2 | PASTLQS |
| 60 | 14E7_27C1 | CDR-L3 | QKYNSAPWT |
| 68 | 5A2_24A1 | VH | QVQLQESGPGLVNPSKTLSLTCTVSGGSISRYFWSWIRQPPGKGLEWIGYIYDSGSTNYNPSLKSRVTISVDTSKNHFSLKLSSVTAADTAVYYCARRGGYYGSGSYGGMDVWGQGTTVTVSS |
| 69 | 5A2_24A1 | CDR-H1 | GGSISRYFWS |
| 70 | 5A2_24A1 | CDR-H2 | YIYDSGSTNYNPSLKS |
| 71 | 5A2_24A1 | CDR-H3 | RGGYYGSGSYGGMDV |
| 72 | 5A2_24A1 | VL | DIQMTQSPSSLSASVGDRVTITCRASQGISNYLAWYQQKPGKIPKLLISAASTLQSGVPSRFSGSGSGTDFTLTISSLQPEDVATYYCQKYDSAPWTFGQGTKVEIK |
| 50 | 5A2_24A1 | CDR-L1 | RASQGISNYLA |
| 73 | 5A2_24A1 | CDR-L2 | AASTLQS |
| 52 | 5A2_24A1 | CDR-L3 | QKYDSAPWT |
| 74 | 5E3-24B4 | VH | QVQLQESGPGLVKPSETLSLTCTVSGGSISSHYWNWIRQPPGKGLEWIGYIHYSGGTNYNPSQKSRVTISVDTSKNQFSLKLSSVTAADTAVYYCAGRRYYFDSSGYLDYWGQGTLVTVSS |
| 75 | 5E3-24B4 | CDR-H1 | GGSISSHYWN |
| 76 | 5E3-24B4 | CDR-H2 | YIHYSGGTNYNPSQKS |
| 77 | 5E3-24B4 | CDR-H3 | RRYYFDSSGYLDY |
| 78 | 5E3-24B4 | VL | DIQMTQSPSSLSASVGDRVTITCRASQGISNYLAWYQQKPGKIPKLLIYAASTLQSGVPSRFSGSGSGTDFTLTISSLQPEDVATYYCQKYNSAPWTFGQGTKLEIK |
| 50 | 5E3-24B4 | CDR-L1 | RASQGISNYLA |
| 73 | 5E3-24B4 | CDR-L2 | AASTLQS |
| 60 | 5E3-24B4 | CDR-L3 | QKYNSAPWT |
| 79 | 7C12_24A6 | VH | QVQLQESGPGLVNPSKTLSLTCTVSGGSISSYFWSWIRQPPGKGLEWIGYIYDSGSTNYNPSLKSRVTISVDTSKNHFSLKLSSVTAADTAVYYCARRGGYYGSGSYGGMDVWGQGTTVTVSS |

TABLE 2-continued

Variable Region Amino Acid Sequences of Human Antibodies

| SEQ ID NO: | Clone Name | Protein Domain | Protein Sequence |
|---|---|---|---|
| 46 | 7C12_24A6 | CDR-H1 | GGSISSYFWS |
| 70 | 7C12_24A6 | CDR-H2 | YIYDSGSTNYNPSLKS |
| 71 | 7C12_24A6 | CDR-H3 | RGGYYGSGSYGGMDV |
| 80 | 7C12_24A6 | VL | DIQMTQSPSSLSASVGDRVTITCRASQGISNYLAWYQQKPGKVPKLLISAASTLQSGVPSRFSGSGSGTDFTLTISSLQPEDVATYYCQKYNSAPWTFGQGTKLEIK |
| 50 | 7C12_24A6 | CDR-L1 | RASQGISNYLA |
| 73 | 7C12_24A6 | CDR-L2 | AASTLQS |
| 60 | 7C12_24A6 | CDR-L3 | QKYNSAPWT |
| 81 | 6H9_27D5 | VH | QVELQQSGPGLVKPSETLSLTCTVSGGSISTYFWSWTRQPPGKGLEWIGYTNYRGNTNYNPSLESRVTISVDTSKNQFSLKLSSVTAADTAVYYCARRGGYYGSGNYGGMDVWGQGTTVTVSS |
| 82 | 6H9_27D5 | CDR-H1 | GGSISTYFWS |
| 83 | 6H9_27D5 | CDR-H2 | YTNYRGNTNYNPSLES |
| 48 | 6H9_27D5 | CDR-H3 | RGGYYGSGNYGGMDV |
| 84 | 6H9_27D5 | VL | DIQMTQSPSSLSASVGDRVTITCRASQGISNYLAWYQQKPGKVPKLLIYAASTLQSGVPSRFSGSGSGTDFTLTISSLQPEDLATYYCQKYDSAPWTFGQGTKLEIK |
| 50 | 6H9_27D5 | CDR-L1 | RASQGISNYLA |
| 73 | 6H9_27D5 | CDR-L2 | AASTLQS |
| 52 | 6H9_27D5 | CDR-L3 | QKYDSAPWT |
| 85 | 10A5_24A2 | VH | QLQLQESGPGLVNPSKTLSLTCNVSGGSMSNYFWSWIRQPPGKGLEWIGYIYNSGNTNYHPSLQSRVTISVDTSKNLFSLKLTSVTAADTAVYYCARRGGYYGSGNYGGLDVWGHGTTVTVSS |
| 86 | 10A5_24A2 | CDR-H1 | GGSMSNYFWS |
| 87 | 10A5_24A2 | CDR-H2 | YIYNSGNTNYHPSLQS |
| 88 | 10A5_24A2 | CDR-H3 | RGGYYGSGNYGGLDV |
| 89 | 10A5_24A2 | VL | DIQMTQSPSSLSASVGDRVTITCRASQGISNYLAWYQQKPGKVPKLLIYAASTLQSGVPSRFSGTGSGTDFTLTISSLQPEDVATYYCQKYDSAPWTFGQGTKVEIK |
| 50 | 10A5_24A2 | CDR-L1 | RASQGISNYLA |
| 73 | 10A5_24A2 | CDR-L2 | AASTLQS |
| 52 | 10A5_24A2 | CDR-L3 | QKYDSAPWT |
| 90 | 16B10_27D2 | VH | QVQLVESGGGVVQPGRSLRLSCAASGFTFNNYGMHWVRQAPGRGLEWVAIIWNDGSNPYYADSVKGRFTISRDNSKNTLYLQMNSLRAEDTAVYYCVRDSSSWFVNYFDYWGQGTLVTVSS |
| 91 | 16B10_27D2 | CDR-H1 | GFTFNNYGMH |
| 92 | 16B10_27D2 | CDR-H2 | IIWNDGSNPYYADSVKG |
| 93 | 16B10_27D2 | CDR-H3 | DSSSWFVNYFDY |
| 94 | 16B10_27D2 | VL | EIVMTQSPATLSVSPGERATLSCRASQSVNRNLAWYQQKPGQAPRLLIYGASTRATGIPASFSGSGSGTEFTLTISSLQSEDFAVYYCQHYNHWPLTFGGGTKVEIK |
| 95 | 16B10_27D2 | CDR-L1 | RASQSVNRNLA |
| 96 | 16B10_27D2 | CDR-L2 | GASTRAT |
| 97 | 16B10_27D2 | CDR-L3 | QHYNHWPLT |

TABLE 2-continued

Variable Region Amino Acid Sequences of Human Antibodies

| SEQ ID NO: | Clone Name | Protein Domain | Protein Sequence |
|---|---|---|---|
| 98 | 3D8D11 | VH | QVQLQESGPGLVKPSETLSLTCTVSGGSISSYFWSWIRQPPGKGLE WIGYIYYSGSTNYNPSLKSRVTISVDTKNQFSLKLSSVTAADTAV YYCARRGGYSYGYGYYGMDVWGQGTTVTVSS |
| 46 | 3D8D11 | CDR-H1 | GGSISSYFWS |
| 63 | 3D8D11 | CDR-H2 | YIYYSGSTNYNPSLKS |
| 99 | 3D8D11 | CDR-H3 | GGYSYGYGYYGMDV |
| 100 | 3D8D11 | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPWTFGQGTKLEIK |
| 50 | 3D8D11 | CDR-L1 | RASQGISNYLA |
| 73 | 3D8D11 | CDR-L2 | AASTLQS |
| 60 | 3D8D11 | CDR-L3 | QKYNSAPWT |
| 101 | 3H3_24B2 | VH | QIQLQESGPGLVNPSKTLSLTCTVSGGSIRSYFWSWIRQPPGKGLE WIGYIYDSGNTNYNPSLKSRVTISVDTKNHFSLKLSSVTAADTAV YYCARRGGYYGSGNYGGMDVWGQGTTVTVSS |
| 102 | 3H3_24B2 | CDR-H1 | GGSIRSYFWS |
| 103 | 3H3_24B2 | CDR-H2 | YIYDSGNTNYNPSLKS |
| 48 | 3H3_24B2 | CDR-H3 | RGGYYGSGNYGGMDV |
| 100 | 3H3_24B2 | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPWTFGQGTKLEIK |
| 50 | 3H3_24B2 | CDR-L1 | RASQGISNYLA |
| 73 | 3H3_24B2 | CDR-L2 | AASTLQS |
| 60 | 3H3_24B2 | CDR-L3 | QKYNSAPWT |
| 104 | 6B6_24B5 | VH | QVQLQESGPGLVKPSETLSLTCTVSGGSISSYYWSWIRQPPGKGLE WIGYIHYSGSTNYNPSLKSRVTISEDTSKNQFSLKLSSVTAADTAV FYCAGRRYYFDSSGYFDYWGQGTLVTVSS |
| 62 | 6B6_24B5 | CDR-H1 | GGSISSYYWS |
| 105 | 6B6_24B5 | CDR-H2 | YIHYSGSTNYNPSLKS |
| 106 | 6B6_24B5 | CDR-H3 | RRYYFDSSGYFDY |
| 100 | 6B6_24B5 | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPWTFGQGTKLEIK |
| 50 | 6B6_24B5 | CDR-L1 | RASQGISNYLA |
| 73 | 6B6_24B5 | CDR-L2 | AASTLQS |
| 60 | 6B6_24B5 | CDR-L3 | QKYNSAPWT |
| 107 | 8C7_24B1 | VH | QVQLQESGPGLVKPSETLSLTCTVSGGSISSYYWSWIRQPPGKGLE WIGYIHYSGSTNYNPSLKSRVTISEDTSKNQFSLKLSSVTAADTAV FYCAGRRYYYDSSGYLDYWGQGTLVTVSS |
| 62 | 8C7_24B1 | CDR-H1 | GGSISSYYWS |
| 105 | 8C7_24B1 | CDR-H2 | YIHYSGSTNYNPSLKS |
| 106 | 8C7_24B1 | CDR-H3 | RRYYYDSSGYLDY |
| 100 | 8C7_24B1 | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPWTFGQGTKLEIK |

TABLE 2-continued

Variable Region Amino Acid Sequences of Human Antibodies

| SEQ ID NO: | Clone Name | Protein Domain | Protein Sequence |
|---|---|---|---|
| 50 | 8C7_24B1 | CDR-L1 | RASQGISNYLA |
| 73 | 8C7_24B1 | CDR-L2 | AASTLQS |
| 60 | 8C7_24B1 | CDR-L3 | QKYNSAPWT |
| 108 | 4F4_27D3 | VH | QVQLQESGPGLVKPSETLSLTCTVSGGSISSHYWSWIRQPPGKGLE WIGYIYYNGGTNYKPSLKSRVTISVDTSKNQFSLKLTSVTAADTAV YYCAGRRYYYDSSGYLDYWGQGTLVTVSS |
| 109 | 4F4_27D3 | CDR-H1 | GGSISSHYWS |
| 110 | 4F4_27D3 | CDR-H2 | YIYYNGGTNYKPSLKS |
| 106 | 4F4_27D3 | CDR-H3 | RRYYYDSSGYLDY |
| 100 | 4F4_27D3 | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPWTFGQGTKLEIK |
| 50 | 4F4_27D3 | CDR-L1 | RASQGISNYLA |
| 73 | 4F4_27D3 | CDR-L2 | AASTLQS |
| 60 | 4F4_27D3 | CDR-L3 | QKYNSAPWT |

TABLE 3

Nucleic Acid Variable Region Sequences of Human Antibodies

| SEQ ID NO: | Clone Name | Protein Domain | DNA Sequence |
|---|---|---|---|
| 111 | 1E2F12H8_3D2 | VH | GAGGTGCAGCTGTTGGAGTCTGGGGGAGGCTTGGTACAGCCTGGGGGGT CCCTGAGACTCTCCTGTGCAGCCTCTGGATTCACCTTTAGCAGCTATGC CATGAGTTGGGTCCGCCAGGCTCCAGGGAAGGGGCTGGAGTGGGTCTCA ATTATTAGTGGTAGTGGTGGTGACACATACTACGCAGACTCCGTGAAGG GCCGGTTCACCATCTCCAGAGACAATTCCAAGAACACGCTGTATCTGCA GATGAACAGCCTGAGAGCCGAGGACACGGCCGTATATTACTGTGCGAAA ACCGATGACCACGGTGACTTCTTTGACTACTGGGGCCAGGGAACCCTGG TCACCGTCTCCTCA |
| 112 | 1E2F12H8_3D2 | VL | GACATCCAGATGACCCAGTCTCCTTCCACCCTGTCTGCATCTGTAGGAG ACAGAGTCACCATCACTTGCCGGGCCAGTCAGAGTATTAGTAGCTGGTT GGCCTGGTATCAGCAGAAACCAGGGAAAGCCCCTAAGCTCCTGATCTAT AAGGCGTCTAGTTTAGAAAGTGGGGTCCCATCAAGGTTCAGCGGCAGTG GATCTGGGACAGAATTCACTCTCACCATCAGCAGCCTGCAGCCTGATGA TTTTGCAACTTATTACTGCCAACAGTATAATAGTTATTGGACGTTCGGC CAAGGGACCAAGGTGGAGATCAAA |
| 113 | 1E12H10_7A1 | VH | CAGGTGCAGCTGGTGGAGTCTGGGGGAGGCGTGGTCCAGCCTGGGAGGT CCCTGAGACTCTCCTGTGCAACGTCTGGATTCACCTTCAGTAGCTATGG CATGCACTGGGTCCGCCAGGCTCCAGGCAAGGGGCTGGAGTGGGTGGCA CTTATATGGTTTGATGGAGGTAATCAATACTATGCGGACTCCGTGAAGG GCCGATTCACCATCTCCAGAGACAATTCCAAGAACACGCTGTATTTGCA ATTGAACAGTCTGAGAGCCGAAGACACGGCTGTGTATTTCTGTGCGAGA GATGTGATCAGTATGGTTCGGGGAGTCCCTTTTGACTACTGGGGCCAGG GAACCCTGGTCACCGTCTCCTCA |
| 114 | 1E12H10_7A1 | VL | GACGCTGTTGTGACTCAGGAATCTGCACTCACCACATCACCTGGTGAAA CAGTCACACTCACTTGTCGCTCAAGTACTGGGGCTGTTACAACTGGTAA CTATGCCAACTGGGTCCAAGAAAAACCAGATCATTTATTCACTGGTCTA ATAGGTGGTATTAAGAACCGAGTTCCAGGTGTTCCTGCCAGATTCTCAG GCTCCCTGATTGGAGACAGGGCTGCCCTCACCATCACAGGGGCACAGAC TGAGGATGAGGCAATATATTTCTGTGCTCTATGGTACAGTAATCATTGG GTGTTCGGTGGAGGAACCAAACTGACTGTCCTAGGC |
| 115 | 3C4A3_7C5 | VH | GAGGTGCAGCTATTGGAGTCTGGGGGAGGCTTGGTACAGCCTGGGGGGT CCCTGAGACTCTCCTGTGCAGCCTCTGGATTCACCTTTAGCAGCTATGC CATGAGCTGGGTCCGCCAGGCTCCAGGGAAGGGGCTGGAGTGGGTCTCA GTTATTAGTGGTAGTGGTGGTAGCACATACTACGCAGACTCCGTGAAGG |

TABLE 3-continued

Nucleic Acid Variable Region Sequences of Human Antibodies

| SEQ ID NO: | Clone Name | Protein Domain | DNA Sequence |
|---|---|---|---|
| | | | GCCGGTTCACCATCTCCAGAGACAATTCCAAGAACACGCTGGATCTGCA AATGAACAGCCTGAGAGCCGAGGACACGGCCGTATATTACTGTGCGAAA TTGGGGGACTACTACTACGGTATGGACGTCTGGGGCCAAGGGACCACGG TCACCGTCTCCTCA |
| 116 | 3C4A3_7C5 | VL | GATATTGTGATGACTCAGTCTCCACTCTCCCTGCCCGTCACCCCTGGAG AGCCGGCCTCCATCTCCTGCAGGTCTAGTCAGAGCCTCCTGCATAGTAA TGGATACAACTATTTGGATTGGTACCTGCAGAAGCCAGGGCAGTCTCCA CAGCTCCTGATCTATTTGGGTTCTAATCGGGCCTCCGGGGTCCCTGACA GGTTCAGTGGCAGTGGATCAGGCACAGATTTTACACTGAAAATCAGCAG AGTGGAGGCTGAGGATGTTGGGGTTTATTACTGCATGCAAGCTCTACAA GCTCCGTGGACGTTCGGCCAAGGGACCAAGCTGGAGATCAAA |
| 117 | 8E11B6 | VH | CAGGTGCAGCTGGAGGAGTCTGGGGGAGGCGTGGTCCAGCCTGGGAGGT CCCTGAGACTCTCCTGTGCAGCGTCTGGATTCACCTTCAGTAGCTATGG CATGCACTGGGTCCGCCAGGCTCCAGGCAAGGGGCTGGAGTGGGTGGCA GTTATATGGTATGATGGAAGTAATACATACTATGCAGACTCCGTGAAGG GCCGATTCACCATCTCCAGAGACAATTCCAAGAACACGCTGTATCTGCA AATGAACAGCCTGAGAGCCGAGGACACGGCTGTGTATTATTGTGCGAGA GAGAGGGAAACTTTTTTTTATGTTATGGATGCCTGGGGTCAAGGAGCTC GGTCACCGTCTCCTCA |
| 118 | 8E11B6 | VL | GACATCCAGATGACCCAGTCTCCTTCCACCCTGTCTGCATCTGTAGGAG ACAGAGTCACCATCACTTGCCGGGCCAGTCAGAGTATTAGTAGCTGGTT GGCCTGGTATCAGCAGAAACAGGGAAAGCCCCTAAGCTCCTGATCTAT AAGGCGTCTAGTTTAGAAAGTGGGGTCCCATCAAGGTTCAGCGGCAGTG GATCTGGGACAGAATTCACTCTCACCATCAGCAGCCTGCAGCCTGATGA TTTTGCAATTTATTACTGCCAACAGTTTAATCGTTTTATCACCTTCGGC CAAGGGACACGACTGGAGATTAAA |
| 119 | 17E8_27C5 | VH | CAGGTGCAGCTGGTGGAGTCTGGGGGAGGCGTGGTCCAGCCTGGGAGGT CCCTGAGACTCTCCTGTGCAGCGTCTGGATTCACCTTTAGTAACTATGG CATGCACTGGGTCCGCCAGGCTCCAGGCAAGGGGCTGGAGTGGATGGCA GGCATATGGTTTGATGGAACTAACAAATACTATATAGACTCCGTGAAGG GCCGATTCACCATTTCCAGAGACAACTCCAAGAACACGCTGTATCTGCA AATGAACAACCTGAGAGCCGAGGACACGGCTGTGTATTATTGTGCGAGA GATGTAATTAGTATGGTTCGGGGAGTCCCCTTTGACTACTGGGGCCAGG GAACCCTGGTCACCGTCTCCTCA |
| 120 | 17E8_27C5 | VL | GACGCTGTTGTGACTCAGGAATCTGCACTCACCACATCACCTGGTGAAA CAGTCACACTCACTTGTCGCTCAAGTACTGGGGCTGTTACAACTAGTAA CTATGCCAACTGGGTCCAAGAAAAACCAGATCATTTATTCACTGGTCTA ATAGGTGGTATCAACAACCGAGCTCCAGGTGTTCCTGCCAGATTCTCAG GCTCCCTGATTGGAGACAAGGCTGCCCTCACCATCACAGGGGCACAGAC TGAGGATGAGGCAATATATTTCTGTGCTCTATGGTACAGCAACCATTGG GTGTTCGGTGGAGGAACCAAACTGACTGTCCTAGGCCAGCCCAAGGCT |
| 121 | 17F4_27C6 | VH | CAGGTGCAGCTGGTGGAGTCTGGGGGAGGCGTGGTCCAGCCTGGGAGGT CCCTGAGACTCTCCTGTGCAGCGTCTGGATTCACCTTCAGTACCTATGG CATTCACTGGGTCCGCCAGGCTCCAGGCAAGGGGCTGGAGTGGGTGGCA GTTATATGGTTTGATGGAAGTAATAAATACTATGCAGACTCCGTGAAGG GCCGATTCACCATCTCCAGAGACAATTCCAAGAACACGCTGTATCTGCA AATGAACAGCCTGAGAGCCGAGGACACGGCTGTGTATTACTGTGCGAGA GATGTAATTAGTATGGTTCGGGGAGTCCCCTTTGACTACTGGGGCCAGG GAACCCTGGTCACCGTCTCCTCA |
| 122 | 17F4_27C6 | VL | GACGCTGTTGTGACTCAGGAATCTGCACTCACCACATCACCTGGTGAAA CAGTCACACTCACTTGTCGCTCAAGTACTGGGGCTGTTACAACTAGTAA CTATGCCAACTGGGTCCAAGAAAAACCAGATCATTTATTCACTGGTCTA ATAGGTGGTATCAACAACCGAGTTCCAGGTGTTCCTGCCAGATTCTCAG GCTCCCTGATTGGAGACAAGGCTGCCCTCACCATCACAGGGGCACAGAC TGAGGATGAGGCAATATATTCTGTGCTCTATGGTACAGCAACCATTGG GTGTTCGGTGGAGGAACCAAGGTGACTGTCCTAGGCCAGCCCAAGGCT |
| 123 | 11H10_27D4 | VH | CAGGTGCAGCTGGTGGAGTCTGGGGGAGGCGTGGTCCAGCCTGGGAGGT CCCTGAGACTCTCCTGTGCAGCGTCTGGATTCACCTTCAGTAACTATGG CATTCACTGGGTCCGCCAGGCTCCAGGCAAGGGGCTGGAGTGGGTGGCA GTTATATGGTTTGATGGAAATAATAAATACTATGCAGACTCCGTGAAGG GCCGATTCACCATCTCCAGAGACAATTCCAAGAACACGCTGTATCTGCA AATGAACAGCCTGAGAGCCGAGGACACGGCTGTGTATTACTGTGCGAGA GACGTCATTACTTTGGTTCGGGGAGTCCCTTTTGACTACTGGGGCCAGG GAACCCTGGTCACCGTCTCCTCA |

TABLE 3-continued

Nucleic Acid Variable Region Sequences of Human Antibodies

| SEQ ID NO: | Clone Name | Protein Domain | DNA Sequence |
|---|---|---|---|
| 124 | 11H10_27D4 | VL | GACGCTGTTGTGACTCAGGAATCTGCACTCACCACATCACCTGGTGAAA CAGTCACAGTCACTTGTCGCTCAAGTACTGGGGCTGTTACAACTAGTAA CTATGCCAATTGGGTCCAAGAAAAACCAGATCATTTATTCACTGGTCTA ATAGGTGGTATCAACAACCGAGCTCCAGGTGTTCCTGCCAGATTCTCAG GCTCCCTGATTGGAGACAAGGCTGCCCTCACCATCACAGGGGCACAGAC TGAGGATGAGGCAATATATTTCTGTGCTCTCTGGTACAGCAACCATTGG GTGTTCGGTGGAGGAACCAAGTTGACTGTCCTAGGCCAGCCCAAG |
| 125 | 1C4_24B3 | VH | CAGGTGCAACTGCAGGAGGCGGGCCCAGGACTGGTGAACCCTTCGAAGA CCCTGTCCCTCACCTGCACTGTCTCTGGTGGCTCCATCAGTAGTTACTT CTGGAGCTGGATCCGGCAGCCCCAGGAAAGGGACTGGAGTGGATTGGT ATATCTATAACAGTGGGAGCACCAACTACAACCCCTCCCTCCAGAGTCG AGTCACCATATCAGTAGACATGTCCAAGAACCACTTCTCCCTGAAGCTG AGCTCTGTGACCGCTGCGGACACGGCCGTATATTACTGTGCGAGAAGGG GGGGTTACTATGGTTCGGGGAATTATGGTGGTATGGACGTCTGGGGCCA AGGGACCACGGTCACCGTCTCCTCA |
| 126 | 1C4_24B3 | VL | GACATCCAGATGACCCAGTCTCCATCCTCCCTGTCTGCATCTGCAGGAG ACAGAGTCACCATCACTTGCCGGGCGAGTCAGGGCATTAGCAATTATTT AGCCTGGTACCAGCAGAAACCAGGGAAAGTTCCTAAGCTCCTGATGTAT GCTGCATCCGCTTTGCAATCAGGGGTCCCATCTCGGTTCAGTGGCAGTG GATCTGGGACAGATTTCACTCTCACCATCAGCAGCCTGCAGCCTGAAGA TGTCGCAACTTATTACTGTCAAAAGTATGACAGTGCCCCGTGGACGTTC GGCCAAGGGACCAAGGTGGAGATCAAA |
| 127 | 20H6_24C3 | VH | CAGGTGCAGCTGCAGGAGTCGGGCCCAGGACTGCTGAAGCCTTCGGAGA CCCTGTCCCTCACCTGCACTGTCTCTGGTGGCTCCATCAGTCCTTACTA CTGGAGCTGGATCCGGCAGCCCCCAGGGAAGGGACTGGAGTGGATTGGG TATATCTATTACAGTGGGAACACCAACTACAACCCCTCCCTCCAGAGCC GACTCACCATATCAGTAGACACGTCCAAGAACCAGTTCTCCCTGAAGCT GAGCTCTGTGACCGCTGCGGACACGGCCGTATATTACTGTGCGAGACGT GGATACAGTTTTGGTTTCTACTACGGTTTGGACGTCTGGGGCCAAGGGA CCACGGTCACCGTCTCCTCA |
| 128 | 20H6_24C3 | VL | GACATCCAGATGACCCAGTCTCCATCCTCCCTGTCTGCATCTGTAGGAG ACAGAGTCACCATCACTTGCCGGGCGAGTCAGGACATTAGCATTTATTT AGCCTGGTATCAGCAGAAACCAGGGAAAGTTCCTAACCTCCTGATCTAT CTTGCTTCCACTTTGCAATCAGGGGTCCCATCTCGGTTCAGTGGCAGTG GATCTGGGACAGATTTCACTCTCACCATCAGCAGCCTGCAGCCTGAAGA TGTTGCAACTTATTACTGTCAAAAGTATAACAGTGCCCCGTGGACGTTC GGCCAAGGGACCAAGCTGGAGATCAAA |
| 129 | 14E7_27C1 | VH | CAGGTGCAGCTGCAGGAGTCGGGCCCAGGACTGGTGAAGCCTTCGGAGA CCCTGTCCCTCACCTGCACTGTCTCTGGTGGCTCCATCAGTAGTTACTA CTGGAGCTGGATCCGGCAGCCCCCAGGGAAGGGACTGGAGTGGATTGGG TATATCTATTACAGTGGGAGCACCAACTACAACCCCTCCCTCAAGAGCC GACTCACCATATCAGTAGACACGTCCAAGAACCAGTTCTCCCTGAAGCT GAGCTCTGTGACCGCTGCGGACACGGCCGTATATTACTGTGCGAGACGT GGATACAGCTATGGTTACTACTACGGTATGGACGTCTGGGGCCAAGGGA CCACGGTCACCGTCTCCTCA |
| 130 | 14E7_27C1 | VL | GACATCCAGATGACCCAGTCTCCATCCTCCCTGTCTGCATCTGTAGGAG ACAGAGTCACCATCACTTGCCGGGCGAGTCAGGACATTAGCAATTATTT AGCCTGGTATCAGCAGAAACCAGGGAAAGTTCCTAAGCTCCTGATCTCT CCTGCATCCACTTTGCAATCAGGGGTCCCATCTCGGTTCAGTGGCAGTG GATCTGGGACAGATTTCACTCTCACCATCAGCAGCCTGCAGCCTGAAGA TGTTGCAACTTATTACTGTCAAAAGTATAACAGTGCCCCGTGGACGTTC GGCCAAGGGACCAAGCTGGAGATCAAA |
| 131 | 5A2_24A1 | VH | CAGGTGCAACTGCAGGAGTCGGGCCCAGGACTGGTGAACCCTTCGAAGA CCCTGTCCCTCACCTGCACTGTCTCTGGTGGCTCCATCAGTAGGTACTT CTGGAGCTGGATCCGGCAGCCCCCAGGGAAGGGACTGGAGTGGATTGGG TATATCTATGACAGTGGGAGCACCAACTACAACCCCTCCCTCAAGAGTC GAGTCACCATATCAGTAGACACGTCCAAGAACCACTTCTCCCTGAAGCT GAGCTCTGTGACCGCTGCGGACACGGCCGTGTATTACTGTGCGAGAAGG GGGGGTTACTATGGTTCGGGGAGTTATGGTGGTATGGACGTCTGGGGCC AAGGGACCACGGTCACCGTCTCCTCA |
| 132 | 5A2_24A1 | VL | GACATCCAGATGACCCAGTCTCCATCCTCCCTGTCTGCATCTGTAGGAG ACAGAGTCACCATCACTTGCCGGGCGAGTCAGGGCATTAGCAATTATTT AGCCTGGTATCAGCAGAAACCAGGGAAAATTCCTAAGCTCCTGATCTCT GCTGCATCCACTTTGCAATCAGGGGTCCCATCTCGGTTCAGTGGCAGTG GATCTGGGACAGATTTCACTCTCACCATCAGCAGCCTGCAGCCTGAAGA |

TABLE 3-continued

Nucleic Acid Variable Region Sequences of Human Antibodies

| SEQ ID NO: | Clone Name | Protein Domain | DNA Sequence |
|---|---|---|---|
| | | | TGTTGCAACTTATTACTGTCAAAAGTATGACAGTGCCCCGTGGACGTTG<br>GCCAAGGGACCAAGGTGGAGATCAAA |
| 133 | 5E3-24B4 | VH | CAGGTGCAGCTGCAGGAGTCGGGCCCAGGACTGGTGAAGCCTTCGGAGA<br>CCCTGTCCCTCACCTGCACTGTCTCTGGTGGCTCCATCAGTAGTCACTA<br>CTGGAACTGGATCCGGCAGCCCCCAGGGAAGGGACTGGAGTGGATTGGG<br>TACATCCATTACAGTGGGGGCACCAACTACAACCCCTCCCAAAAGAGTC<br>GAGTCACCATATCAGTAGACACGTCCAAGAACCAGTTCTCCCTGAAGCT<br>GAGCTCTGTGACCGCTGCGGACACGGCCGTGTATTACTGTGCGGGGAGG<br>AGGTATTACTTTGATAGTAGTGGTTATCTTGACTACTGGGGCCAGGGAA<br>CCCTGGTCACCGTCTCCTCA |
| 134 | 5E3-24B4 | VL | GACATCCAGATGACCCAGTCTCCATCCTCCCTGTCTGCATCTGTAGGAG<br>ACAGAGTCACCATCACTTGCCGGGCGAGTCAGGGGATTAGCAATTATTT<br>AGCCTGGTATCAGCAGAAACCAGGGAAAATTCCTAAGCTCCTGATCTAT<br>GCTGCATCCACTTTGCAATCAGGGGTCCCATCTCGGTTCAGTGGCAGTG<br>GATCTGGGACAGATTTCACTCTCACCATCAGCAGCCTGCAGCCTGAAGA<br>TGTTGCAACTTATTACTGTCAAAAGTATAACAGTGCCCCGTGGACGTTC<br>GGCCAAGGGACCAAGCTGGAGATCAAA |
| 135 | 7C12_24A6 | VH | CAGGTGCAACTGCAGGAGTCGGGCCCAGGACTGGTGAACCCTTCGAAGA<br>CCCTGTCCCTCACCTGCACTGTCTCTGGTGGCTCCATCAGTAGTTACTT<br>CTGGAGCTGGATCCGGCAGCCCCCAGGGAAGGGACTGGAGTGGATTGGG<br>TATATCTATGACAGTGGGAGCACCAACTACAACCCCTCCCTCAAGAGTC<br>GAGTCACCATATCAGTAGACACGTCCAAGAACCACTTCTCCCTGAAGCT<br>GAGCTCTGTGACCGCTGCGGACACGGCCGTGTATTACTGTGCGAGAAGG<br>GGGGGTTACTATGGTTCGGGGAGTTATGGTGGTATGGACGTCTGGGGCC<br>AAGGGACCACGGTCACCGTCTCCTCA |
| 136 | 7C12_24A6 | VL | GACATCCAGATGACCCAGTCTCCATCCTCCCTGTCTGCATCTGTAGGAG<br>ACAGAGTCACCATCACTTGCCGGGCGAGTCAGGGCATTAGCAATTATTT<br>AGCCTGGTATCAGCAGAAACCAGGGAAAGTTCCTAAGCTCCTGATCTCT<br>GCTGCATCCACTTTGCAATCAGGGGTCCCATCTCGGTTCAGTGGCAGTG<br>GATCTGGGACAGATTTCACTCTCACCATCAGCAGCCTGCAGCCTGAAGA<br>TGTTGCAACTTATTACTGTCAAAAGTATAACAGTGCCCCGTGGACGTTC<br>GGCCAAGGGACCAAGCTGGAGATCAAA |
| 137 | 6H9_27D5 | VH | CAGGTGGAGCTGCAGCAGTCGGGCCCAGGACTGGTGAAGCCTTCGGAGA<br>CCCTGTCCCTCACCTGCACTGTCTCTGGTGGCTCCATCAGTACTTACTT<br>CTGGAGCTGGACCCGGCAGCCCCCAGGGAAGGGACTGGAGTGGATTGGG<br>TATACCAACTACAGAGGAAACACCAACTACAACCCCTCCCTCGAGAGTC<br>GAGTCACCATATCAGTAGACACGTCCAAGAACCAGTTCTCCCTGAAGCT<br>GAGCTCTGTGACCGCTGCGGACACGGCCGTGTATTACTGTGCGAGAAGG<br>GGGGGTTATTATGGTTCGGGGAATTATGGTGGTATGGACGTCTGGGGCC<br>AAGGGACCACGGTCACCGTCTCCTCA |
| 138 | 6H9_27D5 | VL | GACATCCAGATGACCCAGTCTCCATCCTCCCTGTCTGCATCTGTAGGAG<br>ACAGAGTCACCATCACTTGCCGGGCGAGTCAGGGCATTAGCAATTATTT<br>AGCCTGGTATCAGCAGAAACCAGGGAAAGTTCCTAAACTCCTGATCTAT<br>GCTGCATCCACTTTGCAATCAGGGGTCCCATCTCGATTCAGTGGCAGTG<br>GATCTGGGACAGATTTCACTCTCACCATCAGCAGCCTGCAGCCTGAAGA<br>TCTTGCAACTTATTACTGTCAAAAGTATGACAGTGCCCCGTGGACGTTC<br>GGCCAAGGGACCAAGCTGGAGATCAAA |
| 139 | 10A5_24A2 | VH | CAGTTGCAACTGCAGGAGTCGGGCCCAGGACTGGTGAACCCTTCGAAGA<br>CCCTGTCCCTCACCTGCAATGTCTCTGGTGGCTCCATGAGTAATTACTT<br>CTGGAGCTGGATCCGGCAGCCCCCAGGGAAGGGACTGGAGTGGATTGGG<br>TACATCTATAATTCTGGGAACACCAACTACCACCCCTCCCTCCAGAGTC<br>GAGTCACCATATCAGTAGACACGTCCAAGAACCTCTTCTCCCTGAAGCT<br>GACCTCTGTGACCGCTGCGGACACGGCCGTGTATTATTGTGCGAGAAGG<br>GGGGGTTACTATGGTTCGGGGAATTATGGTGGTTTGGACGTCTGGGGCC<br>ACGGGACCACGGTCACCGTCTCCTCA |
| 140 | 10A5_24A2 | VL | GACATCCAGATGACCCAGTCTCCATCCTCCCTGTCTGCATCTGTAGGAG<br>ACAGAGTCACCATCACTTGCCGGGCGAGTCAGGGCATTAGCAATTATTT<br>AGCCTGGTATCAGCAGAAACCAGGGAAAGTTCCTAAGCTCCTGATCTAT<br>GCTGCATCCACTTTGCAATCAGGGGTCCCATCTCGGTTCAGTGGCACTG<br>GATCTGGGACAGATTTCACTCTCACCATCAGCAGCCTGCAGCCTGAAGA<br>TGTTGCAACTTATTACTGTCAAAAGTATGACAGTGCCCCGTGGACGTTC<br>GGCCAAGGGACCAAGGTGGAGATCAAA |
| 141 | 16B10_27D2 | VH | CAGGTGCAGCTGGTGGAGTCTGGGGGAGGCGTGGTCCAGCCTGGGAGGT<br>CCCTGAGACTCTCCTGTGCAGCGTCTGGATTCACCTTCAATAACTATGG<br>CATGCACTGGGTCCGCCAGGCTCCTGGCAAGGGGCTGGAGTGGGTGGCA |

TABLE 3-continued

Nucleic Acid Variable Region Sequences of Human Antibodies

| SEQ ID NO: | Clone Name | Protein Domain | DNA Sequence |
|---|---|---|---|
| | | | ATTATATGGAATGATGGAAGTAATCCATACTATGCAGACTCCGTGAAGG<br>GCCGATTCACCATCTCCAGAGACAATTCCAAGAACACGCTGTATCTGCA<br>AATGAACAGCCTGAGAGCCGAAGACACGGCTGTATATTACTGTGTGAGA<br>GATAGCAGCAGCTGGTTCGTGAACTACTTTGACTACTGGGGCCAGGGAA<br>CCCTGGTCACCGTCTCCTCA |
| 142 | 16B10_27D2 | VL | GAAATAGTGATGACGCAGTCTCCAGCCACCCTGTCTGTGTCTCCAGGGG<br>AAAGAGCCACCCTCTCCTGCAGGGCCAGTCAGAGTGTTAATAGGAACTT<br>AGCCTGGTACCAGCAGAAACCTGGCCAGGCTCCCAGGCTCCTCATCTAT<br>GGTGCATCCACCAGGGCCACTGGTATCCCAGCCAGTTTCAGTGGCAGTG<br>GGTCTGGGACAGAGTTCACTCTCACCATCAGCAGCCTGCAGTCTGAAGA<br>TTTTGCAGTTTATTACTGTCAGCATTATAATCACTGGCCGCTCACTTTC<br>GGCGGAGGGACCAAGGTGGAGATCAAA |
| 143 | 3D8D11 | VH | CAGGTGCAGCTACAGGAGTCGGGCCCAGGACTGGTGAAGCCTTCGGAGA<br>CCCTGTCCCTCACCTGCACTGTCTCTGGTGGCTCCATCAGTAGTTACTT<br>CTGGAGCTGGATCCGGCAGCCCCCAGGGAAGGGACTGGAGTGGATTGGG<br>TATATCTATTACAGTGGGAGCACCAACTACAACCCCTCCCTCAAGAGTC<br>GAGTCACCATATCAGTAGACACGTCCAAGAACCAGTTCTCCCTGAAGCT<br>GAGTTCTGTGACCGCTGCGGACACGGCCGTGTATTACTGTGCGAGAAGG<br>GGGGGATACAGCTATGGTTACGGCTACTACGGTATGGACGTCTGGGGCC<br>AAGGGACCACGGTCACCGTCTCCTCA |
| 144 | 3D8D11<br>3H3_24B2<br>6B6_24B5<br>8C7_24B1<br>4F4_27D3 | VL | GACATCCAGATGACCCAGTCTCCATCCTCCCTGTCTGCATCTGTAGGAG<br>ACAGAGTCACCATCACTTGCCGGGCGAGTCAGGGCATTAGCAATTATTT<br>AGCCTGGTATCAGCAGAAACAGGGAAAGTTCCTAAGCTCCTGATCTAT<br>GCTGCATCCACTTTGCAATCAGGGGTCCCATCTCGGTTCAGTGGCAGTG<br>GATCTGGGACAGATTTCACTCTCACCATCAGCAGCCTGCAGCCTGAAGA<br>TGTTGCAACTTATTACTGTCAAAAGTATAACAGTGCCCCGTGGACGTTC<br>GGCCAAGGGACCAAGCTGGAGATCAAA |
| 145 | 3H3_24B2 | VH | CAGATACAACTGCAGGAGTCGGGCCCAGGACTGGTGAACCCTTCGAAGA<br>CCCTGTCCCTCACCTGCACTGTCTCTGGTGGCTCCATCAGAAGTTACTT<br>CTGGAGCTGGATCCGGCAGCCCCCAGGGAAGGGACTGGAGTGGATTGGG<br>TATATCTATGACAGTGGGAACACCAACTACAACCCCTCCCTCAAGAGTC<br>GAGTCACCATATCAGTAGACACGTCCAAGAACCACTTCTCCCTGAAGCT<br>GAGTTCTGTGACCGCTGCGGACACGGCCGTGTATTACTGTGCGAGAAGG<br>GGGGGTTACTATGGTTCGGGGAATTATGGTGGTATGGACGTCTGGGGCC<br>AAGGGACCACGGTCACCGTCTCCTCA |
| 146 | 6B6_24B5 | VH | CAGGTGCAGCTGCAGGAGTCGGGCCCAGGACTGGTGAAGCCTTCGGAGA<br>CCCTGTCCCTCACCTGCACTGTCTCTGGTGGCTCCATCAGTAGTTACTA<br>CTGGAGCTGGATCCGGCAGCCCCCAGGGAAGGGACTGGAGTGGATTGGG<br>TATATCCATTACAGTGGGAGCACCAACTACAATCCCTCCCTCAAGAGTC<br>GAGTCACCATATCAGAAGACACGTCCAAGAACCAGTTCTCCCTGAAGCT<br>GAGCTCTGTGACCGCTGCGGACACGGCCGTGTTTTACTGTGCGGGGAGG<br>AGGTATTACTTTGATAGTAGTGGTTATTTTGACTACTGGGGCCAGGGAA<br>CCCTGGTCACCGTCTCCTCA |
| 147 | 8C7_24B1 | VH | CAGGTGCAGCTGCAGGAGTCGGGCCCAGGACTGGTGAAGCCTTCGGAGA<br>CCCTGTCCCTCACCTGCACTGTCTCTGGTGGCTCCATCAGTAGTTACTA<br>CTGGAGCTGGATCCGGCAGCCCCCAGGGAAGGGACTGGAGTGGATTGGG<br>TATATCCATTACAGTGGGAGCACCAACTACAACCCCTCCCTCAAGAGTC<br>GAGTCACCATATCAGAAGACACGTCCAAGAACCAGTTCTCCCTGAAGCT<br>GAGCTCTGTGACCGCTGCGGACACGGCCGTGTTTTACTGTGCGGGGAGG<br>AGGTATTACTATGATAGTAGTGGTTATCTTGACTACTGGGGCCAGGGAA<br>CCCTGGTCACCGTCTCCTCA |
| 148 | 4F4_27D3 | VH | CAGGTGCAGCTGCAGGAGTCGGGCCCAGGACTGGTGAAGCCTTCGGAGA<br>CCCTGTCCCTCACCTGCACCGTCTCTGGTGGCTCCATCAGTAGCCACTA<br>CTGGAGCTGGATCCGGCAGCCCCCAGGGAAGGGACTGGAGTGGATTGGG<br>TATATCTATTACAATGGGGGCACCAACTACAAACCCTCCCTAAAGAGTC<br>GAGTCACCATATCAGTAGACACGTCCAAGAACCAGTTCTCCCTGAAGCT<br>GACCTCTGTGACCGCTGCGGACACGGCCGTGTATTACTGTGCGGGGAGG<br>AGGTATTACTATGATAGTAGTGGCTATCTTGACTATTGGGGCCAGGGAA<br>CCCTGGTCACCGTCTCCTCA |

Binding affinity curves for four antibodies: E2F12H8, E12H10, 3C4A3, and 8E11B6 are set forth in FIG. 1. Competition assay using the Octet™ instrument yielded data demonstrating unique binding to ILT3 between all four antibodies.

Binding kinetic values against human ILT3 (for all antibodies set forth in Table 2) and against cynomolgus monkey ILT3 (for antibodies E2F12H8, E12H10, 3C4A3, and 8E11B6) are set forth in Table 4, below.

TABLE 4

Binding affinities of human anti-human ILT3 antibodies

| Antibody Name | Human ILT3 $K_D$ (nM) | Cynomolgus Monkey ILT3 $K_D$ (nM) |
|---|---|---|
| 1E12H10_7A1 | 3 | 200 |
| 1E2F12H8_3D2 | 6 | 27 |
| 8E11B6 | 10 | >1,000 |
| 3C4A3_7C5 | 21 | 56 |
| 6H9_27D5 | 1 | |
| 20H6_24C3 | 1 | |
| 11H10_27D4 | 1 | |
| 16B10_27D2 | 1 | |
| 5E3-24B4 | 2 | |
| 17E8_27C5 | 2 | |
| 10A5_24A2 | 2 | |
| 17F4_27C6 | 3 | |
| 6B6_24B5 | 8 | |
| 1C4_24B3 | 12 | |
| 5A2_24A1 | 30 | |
| 4F4_27D3 | 30 | |
| 3H3_24B2 | 40 | |
| 7C12_24A6 | 50 | |
| 8C7_24B1 | 60 | |
| 14E7_27C1 | 75 | |
| 3D8D11 | 170 | |

EC50 values of antibodies 5E3, 6B6, 6H9, 20H6, 17E8, 3C4A3, 1E12 (also referred to herein as 1E12H10), 1E2 (also referred to herein as 1E2F12H8), and 3D8, range from 6 to greater than 100 nM affinities (see FIG. 2).

Example 3. In Vitro Target Internalization and Killing Assay

Given that myeloid derived suppressor cells (MDSC) infiltrating solid tumors have been shown to express ILT3 (de Goeje, P. L. et al, OncoImmunology. 2016; 4, e1014242-1-e1014242-11) and that targeting and eliminating MDSCs promotes anti-tumor response by tumor infiltrating lymphocytes (TILS) (Stromnes, I. M. et al, Gut. 2014; 63, 1769-1781), developing antibodies conjugated to a toxin that can promote ILT3 internalization is of interest. Thus, the target internalization and killing ability of ten recombinant antibodies (3D8, 6H9, 20H6, 6B6, 5E3, 17E8, 1E12H10 (also referred to herein as 1E12 or E12H10), 3C4A3, 1E2F12H8 (also referred to herein as 1E2 or E2F12H8), and 8E11 conjugated to the saporin toxin was determined.

Method
In Vitro Killing of Cells Endogenously Expressing ILT3 Using a Secondary ADC Assay ILT3+ THP1 cells were cultured at least 48 hours before seeding at 5,000 cells/well on 96 well flat clear bottom black polystyrene tissue culture treated microplates (Corning Lifescience, Tewksbury, MA) in 60 ul RPMI+10% FBS/well. THP1 is a human acute monocytic leukemia (AML) cell line (see, e.g., Chanput, W., et al. Int Immunopharmacol. 2014 November; 23(1):37-45). Twenty-four hours later, master mix of the anti-ILT3 antibody was prepared by diluting the antibody with complete culture media at a concentration of 0.5 µg/ml (final concentration 0.1 ug/ml). The secondary anti-human IgG antibody conjugated to saporin, Fab-ZAP human IT 51™ (Advanced Targeting Systems, San Diego, CA), was diluted to a concentration of 2 µg/ml (final concentration 0.4 µg/ml) with complete culture media. Twenty microliters per well of the primary antibody or media alone were added onto the cell plates using a multichannel repeater pipet, minimizing the introduction of bubbles to the wells.

Within 5 minutes, 20 µL/well of secondary ADC or media alone were added onto the cell plates. Plates were incubated for 72 hours at 37° C. At 72 hours, the CellTiter Glo™ reagent (Promega, Madison, WI) was thawed and equilibrated to room temperature as well as the plate for 10 min, 100 µL of prepared CellTiter Glo™ was added to each well, followed by a gentle shake with an orbital shaker. The plates were incubated for 30 minutes at room temperature and read with an EnSpire™ multimode plate luminometer (Perkin Elmer, Waltham, MA).

Results

As set forth in FIG. 3B, six antibodies showed some level of ILT3 receptor internalization, resulting in THP1 cell death mediated by the saporin conjugated secondary antibody. Two antibodies, 1E12 and 17E8, showed a slight degree of killing. As also shown in FIG. 3B, the antibody clones 3D8 and 3C4A3 showed no in vitro killing of THP1 cells.

Example 4. In Vitro Effects of Blocking ILT3 in Combination with Other Immune-Oncology Targets on T Cell Activation and Effector Function ILT3 has been shown to directly inhibit T cell activation, proliferation and effector cell function (Kim-Schulze et al., 2006, Journal of Immunology 176, 2790-2798), which is driven by binding of ILT3 to a yet unidentified receptor on T cells. Blockade of ILT3 with antibodies has been shown to reverse T cell tolerization, resulting in T cell activation and IFNγ secretion (Suciu-Foca et al., 2007, Journal of Immunology 178, 7432-7441). This Example describes the effects of blocking ILT3 with an ILT3 antibody in combination with immune-oncology antibodies that target other immunoregulator antigens, such as anti-PD1, anti-PD-L1 and anti-CTLA4 antibodies.

Method
Effects of In Vitro Blockade of ILT3, PD1, PD-L1 and CTLA4 with Monoclonal Antibodies on T Cell Activation Purified monocytes were cultured at a density of 1×10$^6$ cells per mL with 100 ng/mL of human GM-CSF (CST, #8922) and human IL-4 (CST, #8919) for 7 days, media was replaced and replenished with fresh cytokine every 2 days. The differentiation of CD14$^-$CD11$^{high}$CD831 $^{low}$ immature dendritic cells (DC) was confirmed by flow cytometric analysis, which was >98% routinely. DCs were then incubated for an additional day with 100 units/mL of recombinant human IL-10 (R&D Systems) and human IFNα-2b (PBL assay science, #11145-1). Expression of ILT3 was determined after 1 day in culture by flow cytometry. Cytokine treated monocyte derived dendritic cells (MDDC) were cultured with CD25$^-$ peripheral blood allogeneic T cells, from healthy donors, at a 1:10 (MDDC:T cell) ratio for a period of 6 days in the presence of 20 µg/mL of anti-human ILT3 fully human antibodies of the invention (FIG. 4) or mouse anti-human ILT3 antibody control (clone ZM4.1, available from Thermofisher, FIGS. 5 and 6) alone or in combination with the same concentration of anti-human PD1 (Nivolomab); anti-human PD-L1 (Atezolizumab); or anti-CTLA4 (Ipilimumab) all purchased from InvivoGen.

After the 6 days in culture, T cells were stained with antibodies against CD3, CD4 or CD8 and CD25. T cell activation was assessed by the expression of CD25 using flow cytometry. IFNγ levels were determined by enzyme-linked immunosorbent assay (ELISA) using BD Biosciences OptEIA IFNγ kit.

Flow Cytometry to Determine T Cell Activation

Multicolor flow cytometry was used to determine activation status of T cells cultured in mixed lymphocyte reactions in the presence or absence of anti-PD1, anti-PD-L1, anti-CTLA4 or anti-ILT3 antibodies as single agents or in combination studies, whereby anti-ILT3 antibodies were combined with either anti-PD1, anti-PD-L1 or anti-CTLA4 antibodies. T cell subsets were identified by staining with antibodies against CD3, CD4 or CD8. Activation was determined by expression of CD25, using fluorochrome labeled anti-CD25 antibodies. Cells were stained using standard flow cytometry procedure. Briefly, cells were collected from tissue culture plates, washed twice with flow buffer (1×PBS, 0.5% BSA, 2 mM EDTA). After the second wash, the cells were counted and the concentration was adjusted to $1 \times 10^6$ cells per 1 mL. Cells were transferred to 96-V bottom polypropylene plates and spun at 1250 rpm for 5 minutes at 4° C. to pellet the cells. The cell pellets were resuspended with a mix of antibodies against T cell antigens, each at a final concentration of 1 ug/mL diluted in cold flow buffer and incubated at 4° C. for 30 minutes. After incubation, cells were washed 2× with flow buffer and then resuspended in 200 μL of flow buffer containing propidium iodide (PI) to identify dead cells and remove from analysis. Cells were run on a MACSQuant Analyzer 10 flow cytometer (Miltenyi Biotec, Bergisch Gladbach, Germany) and analysis was performed with FlowJo software (FlowJo, Ashland, OR).

Effects of In Vitro Blockade of ILT3 and PD-L1 with Monoclonal Antibodies on T Cell IFNγ Secretion.

IFNγ levels were measured using an ELISA kit purchased from BD Biosciences, following the manufacturer's instructions. Briefly, samples were mixed with provided ELISA diluent and allocated in corresponding pre-coated wells. Standards provided were treated similarly. Samples and standards were incubated for 2 hours at room temperature protected from light. The working detector solution was prepared 15 minutes prior to use. Detection Antibody was added and mixed well into a clean tube along with Enzyme Concentrate (250×). The wells were washed 5 times with wash buffer supplied by manufacturer prior to adding the detection solution for 1 hour at room temperature. The detection solution was decanted and wells were washed 7 times with wash buffer. After the last wash, plates were blotted in absorbent paper to remove any residual buffer and 100 μL of TMB One-Step Substrate Reagent was added to each well and incubated without plate sealer for 30 minutes at room temperature in the dark. Stop solution was added and plates were read on a Perkin Elmer Multimode EnSpire Plate Reader at 450 nm absorbance.

Results

As shown in FIG. 4A, blockade of ILT3 with anti-ILT3 antibodies of the invention alone resulted in an increase in CD25 expression in both CD4 and CD8 positive T cells. As set forth in FIG. 5, a commercially available mouse anti-ILT3 monoclonal antibody, clone ZM4.1 (available from ThermoFisher), alone, also resulted in increased in CD25 expression in both CD4 and CD8 positive T cells.

The addition of anti-CTLA4 antibody Ipilimumab in combination with mouse anti-ILT3 monoclonal antibody clone ZM4.1 did not enhance T cell activation as measured by CD25 expression that was already achieved by ILT3 blockade with mouse anti-ILT3 monoclonal antibody clone ZM4.1 alone (FIGS. 5A and B). However, blockade of ILT3 with mouse anti-ILT3 monoclonal antibody clone ZM4.1 in combination with blockade of PD1 with an anti-PD1 antibody (see FIGS. 5C and D) or blockade of PDL1 with an anti-PDL1 antibody (see FIGS. 5E and F), resulted in a statistically significant increase in activation of CD4 and CD8 positive T cells. Mouse anti-ILT3 monoclonal antibody clone ZM4.1 in combination with an anti-PD-L1 antibody resulted in a better additive response than blocking ILT3 and PD1 (see FIGS. 5E and 5F).

Blockade of both ILT3 with certain human antibodies of the invention in combination with blockade of PD-L1 with anti-PD-L1 antibody Atezolizumab resulted in increased IFNγ levels as compared with Atezolizumab alone (see FIG. 4B). Blockade of both ILT3 with mouse anti-ILT3 monoclonal antibody clone ZM4.1 in combination with blockade of PD-L1 with anti-PD-L1 antibody Atezolizumab resulted in increased IFNγ levels in four donor samples (see FIG. 6).

Thus, these results illustrate that combining an ILT3 antibody with a checkpoint inhibitor antibody, results in an additive effect in increasing activation of T cells.

SEQUENCE SUMMARY

| SEQ ID NO: | Description |
|---|---|
| 1 | E2F12H8 VH amino acid sequence |
| 2 | E2F12H8, 3C4A3 VH CDR1 amino acid sequence |
| 3 | E2F12H8 VH CDR2 amino acid sequence |
| 4 | E2F12H8 VH CDR3 amino acid sequence |
| 5 | E2F12H8 VL amino acid sequence |
| 6 | E2F12H8, 8E11B6 VL CDR1 amino acid sequence |
| 7 | E2F12H8, 8E11B6 VL CDR2 amino acid sequence |
| 8 | E2F12H8 VL CDR3 amino acid sequence |
| 9 | E12H10 VH amino acid sequence |
| 10 | E12H10, 8E11B6 VH CDR1 amino acid sequence |
| 11 | E12H10 VH CDR2 amino acid sequence |
| 12 | E12H10, 17E8_27C5, 17F4_27C6 VH CDR3 amino acid sequence |
| 13 | E12H10 VL amino acid sequence |
| 14 | E12H10 VL CDR1 amino acid sequence |
| 15 | E12H10 VL CDR2 amino acid sequence |
| 16 | E12H10, 17E8_27C5, 17F4_27C6, 11H10_27D4 VL CDR3 amino acid |
| 17 | 3C4A3 VH amino acid sequence |
| 18 | 3C4A3 VH CDR2 amino acid sequence |
| 19 | 3C4A3 VH CDR3 amino acid sequence |
| 20 | 3C4A3 VL amino acid sequence |
| 21 | 3C4A3 VL CDR1 amino acid sequence |
| 22 | 3C4A3 VL CDR2 amino acid sequence |
| 23 | 3C4A3 VL CDR3 amino acid sequence |
| 24 | 8E11B6 VH amino acid sequence |
| 25 | 8E11B6 VH CDR2 amino acid sequence |
| 26 | 8E11B6 VH CDR3 amino acid sequence |
| 27 | 8E11B6 VL amino acid sequence |
| 28 | 8E11B6 VL CDR3 amino acid sequence |
| 29 | 17E8_27C5 VH amino acid sequence |
| 30 | 17E8_27C5 VH CDR1 amino acid sequence |
| 31 | 17E8_27C5 VH CDR2 amino acid sequence |
| 32 | 17E8_27C5 VL amino acid sequence |
| 33 | 17E8_27C5, 17F4_27C6, 11H10_27D4 VL CDR1 amino acid sequence |
| 34 | 17E8_27C5, 11H10_27D4 VL CDR2 amino acid sequence |
| 35 | 17F4_27C6 VH amino acid sequence |
| 36 | 17F4_27C6 VH CDR1 amino acid sequence |
| 37 | 17F4_27C6 VH CDR2 amino acid sequence |
| 38 | 17F4_27C6 VL amino acid sequence |
| 39 | 17F4_27C6 VL CDR2 amino acid sequence |
| 40 | 11H10_27D4 VH amino acid sequence |
| 41 | 11H10_27D4 VH CDR1 amino acid sequence |
| 42 | 11H10_27D4 VH CDR2 amino acid sequence |

SEQUENCE SUMMARY

| SEQ ID NO: | Description |
|---|---|
| 43 | 11H10_27D4 VH CDR3 amino acid sequence |
| 44 | 11H10_27D4 VL amino acid sequence |
| 45 | 1C4_24B3 VH amino acid sequence |
| 46 | 1C4_24B3, 7C12_24A6, 3D8D11 VH CDR1 amino acid sequence |
| 47 | 1C4_24B3 VH CDR2 amino acid sequence |
| 48 | 1C4_24B3, 6H9_27D5, 3H3_24B2 VH CDR3 amino acid sequence |
| 49 | 1C4_24B3 VL amino acid sequence |
| 50 | 1C4_24B3, 5A2_24A1, 5E3_24B4, 7C12_24A6, 6H9_27D5, 10A5_24A2, 3D8D11, 3H3_24B2, 6B6_24B5, 8C7_24B1, 4F4_27D3 VL CDR1 amino acid sequence |
| 51 | 1C4_24B3 VL CDR2 amino acid sequence |
| 52 | 1C4_24B3, 5A2_24A1, 6H9_27D5, 10A5_24A2 VL CDR3 amino acid |
| 53 | 20H6_24C3 VH amino acid sequence |
| 54 | 20H6_24C3 VH CDR1 amino acid sequence |
| 55 | 20H6_24C3 VH CDR2 amino acid sequence |
| 56 | 20H6_24C3 VH CDR3 amino acid sequence |
| 57 | 20H6_24C3 VL amino acid sequence |
| 58 | 20H6_24C3 VL CDR1 amino acid sequence |
| 59 | 20H6_24C3 VL CDR2 amino acid sequence |
| 60 | 20H6_24C3, 14E7_27C1, 5E3_24B4, 7C12_24A6, 3D8D11, 3H3_24B2, 6B6_24B5, 8C7_24B1, 4F4_27D3 VL CDR3 amino acid sequence |
| 61 | 14E7_27C1 VH amino acid sequence |
| 62 | 14E7_27C1, 6B6_24B5, 8C7_24B1 VH CDR1 amino acid sequence |
| 63 | 14E7_27C1 VH CDR2 amino acid sequence |
| 64 | 14E7_27C1 VH CDR3 amino acid sequence |
| 65 | 14E7_27C1 VL amino acid sequence |
| 66 | 14E7_27C1 VL CDR1 amino acid sequence |
| 67 | 14E7_27C1 VL CDR2 amino acid sequence |
| 68 | 5A2_24A1 VH amino acid sequence |
| 69 | 5A2_24A1 VH CDR1 amino acid sequence |
| 70 | 5A2_24A1, 7C12_24A6 VH CDR2 amino acid sequence |
| 71 | 5A2_24A1, 7C12_24A6 VH CDR3 amino acid sequence |
| 72 | 5A2_24A1 VL amino acid sequence |
| 73 | 5A2_24A1, 5E3_24B4, 7C12_24A6, 6H9_27D5, 10A5_24A2, 3D8D11, 3H3_24B2, 6B6_24B5, 8C7_24B1, 4F4_27D3 VL CDR2 amino acid sequence |
| 74 | 5E3_24B4 VH amino acid sequence |
| 75 | 5E3_24B4 VH CDR1 amino acid sequence |
| 76 | 5E3_24B4 VH CDR2 amino acid sequence |
| 77 | 5E3_24B4 VH CDR3 amino acid sequence |
| 78 | 5E3_24B4 VL amino acid sequence |
| 79 | 7C12_24A6 VH amino acid sequence |
| 80 | 7C12_24A6 VL amino acid sequence |
| 81 | 6H9_27D5 VH amino acid sequence |
| 82 | 6H9_27D5 VH CDR1 amino acid sequence |
| 83 | 6H9_27D5 VH CDR2 amino acid sequence |
| 84 | 6H9_27D5 VL amino acid sequence |
| 85 | 10A5_24A2 VH amino acid sequence |
| 86 | 10A5_24A2 VH CDR1 amino acid sequence |
| 87 | 10A5_24A2 VH CDR2 amino acid sequence |
| 88 | 10A5_24A2 VH CDR3 amino acid sequence |
| 89 | 10A5_24A2 VL amino acid sequence |
| 90 | 16B10_27D2 VH amino acid sequence |
| 91 | 16B10_27D2 VH CDR1 amino acid sequence |
| 92 | 16B10_27D2 VH CDR2 amino acid sequence |
| 93 | 16B10_27D2 VH CDR3 amino acid sequence |
| 94 | 16B10_27D2 VL amino acid sequence |
| 95 | 16B10_27D2 VL CDR1 amino acid sequence |
| 96 | 16B10_27D2 VL CDR2 amino acid sequence |
| 97 | 16B10_27D2 VL CDR3 amino acid sequence |
| 98 | 3D8D11 VH amino acid sequence |
| 99 | 3D8D11 VH CDR3 amino acid sequence |
| 100 | 3D8D11, 3H3_24B2, 6B6_24B5, 8C7_24B1, 4F4_27D3 VL amino acid |
| 101 | 3H3_24B2 VH amino acid sequence |
| 102 | 3H3_24B2 VH CDR1 amino acid sequence |
| 103 | 3H3_24B2 VH CDR2 amino acid sequence |
| 104 | 6B6_24B5 VH amino acid sequence |
| 105 | 6B6_24B5, 8C7_24B1 VH CDR 2 amino acid sequence |
| 106 | 6B6_24B5, 8C7_24B1, 4F4_27D3 VH CDR3 amino acid sequence |
| 107 | 8C7_24B1 VH amino acid sequence |
| 108 | 4F4_27D3 VH amino acid sequence |
| 109 | 4F4_27D3 VH CDR1 amino acid sequence |
| 110 | 4F4_27D3 VH CDR2 amino acid sequence |
| 111 | E2F12H8 VH nucleic acid sequence |
| 112 | E2F12H8 VL nucleic acid sequence |
| 113 | E12H10 VH nucleic acid sequence |
| 114 | E12H10 VL nucleic acid sequence |
| 115 | 3C4A3 VH nucleic acid sequence |
| 116 | 3C4A3 VL nucleic acid sequence |
| 117 | 8E11B6 VH nucleic acid sequence |
| 118 | 8E11B6 VL nucleic acid sequence |
| 119 | 17E8_27C5 VH nucleic acid sequence |
| 120 | 17E8_27C5 VL nucleic acid sequence |
| 121 | 17F4_27C6 VH nucleic acid sequence |
| 122 | 17F4_27C6 VL nucleic acid sequence |
| 123 | 11H10_27D4 VH nucleic acid sequence |
| 124 | 11H10_27D4 VL nucleic acid sequence |
| 125 | 1C4_24B3 VH nucleic acid sequence |
| 126 | 1C4_24B3 VL nucleic acid sequence |
| 127 | 20H6_24C3 VH nucleic acid sequence |
| 128 | 20H6_24C3 VL nucleic acid sequence |
| 129 | 14E7_27C1 VH nucleic acid sequence |
| 130 | 14E7_27C1 VL nucleic acid sequence |
| 131 | 5A2_24A1 VH nucleic acid sequence |
| 132 | 5A2_24A1 VL nucleic acid sequence |
| 133 | 5E3-24B4 VH nucleic acid sequence |
| 134 | 5E3-24B4 VL nucleic acid sequence |
| 135 | 7C12_24A6 VH nucleic acid sequence |
| 136 | 7C12_24A6 VL nucleic acid sequence |
| 137 | 6H9_27D5 VH nucleic acid sequence |
| 138 | 6H9_27D5 VL nucleic acid sequence |
| 139 | 10A5_24A2 VH nucleic acid sequence |
| 140 | 10A5_24A2 VL nucleic acid sequence |
| 141 | 16B10_27D2 VH nucleic acid sequence |
| 142 | 16B10_27D2 VL nucleic acid sequence |
| 143 | 3D8D11 VH nucleic acid sequence |
| 144 | 3D8D11, 3H3_24B2, 6B6_24B5, 8C7_24B1, 4F4_27D3 VL nucleic acid |
| 145 | 3H3_24B2 VH nucleic acid sequence |
| 146 | 6B6_24B5 VH nucleic acid sequence |
| 147 | 8C7_24B1 VH nucleic acid sequence |
| 148 | 4F4_27D3 VH nucleic acid sequence |
| 149 | Human ILT3 amino acid sequence (with signal sequence) |
| 150 | Primer |
| 151 | Primer |
| 152 | Primer |
| 153 | Primer |
| 154 | Primer |
| 155 | Primer |
| 156 | Primer |
| 157 | Primer |
| 158 | Primer |
| 159 | Primer |
| 160 | Primer |
| 161 | Primer |
| 162 | Primer |
| 163 | Primer |
| 164 | Primer |
| 165 | Primer |
| 166 | Primer |
| 167 | Primer |
| 168 | Primer |
| 169 | Primer |
| 170 | Primer |

| SEQUENCE SUMMARY | |
|---|---|
| SEQ ID NO: | Description |
| 171 | Primer |
| 172 | Primer |
| 173 | Primer |
| 174 | Primer |
| 175 | Primer |

INCORPORATION BY REFERENCE

The contents of all references, patents, pending patent applications and published patents, and Accession Numbers, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated antibody, or antigen binding portion thereof, that binds to immunoglobulin-like transcript 3 (ILT3), wherein the antibody, or antigen binding portion thereof, comprises:
- a heavy chain variable region that is at least 95% identical to SEQ ID NO: 81 and a light chain variable region that is at least 95% identical to SEQ ID NO: 84;
- a heavy chain variable region that is at least 95% identical to SEQ ID NO: 1 and a light chain variable region that is at least 95% identical to SEQ ID NO: 5;
- a heavy chain variable region that is at least 95% identical to SEQ ID NO: 53 and a light chain variable region that is at least 95% identical to SEQ ID NO: 57;
- a heavy chain variable region that is at least 95% identical to SEQ ID NO: 74 and a light chain variable region that is at least 95% identical to SEQ ID NO: 78; or
- a heavy chain variable region that is at least 95% identical to SEQ ID NO: 104 and a light chain variable region that is at least 95% identical to SEQ ID NO: 100.

2. The isolated antibody, or antigen binding portion thereof, of claim 1, wherein
- the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 52, a CDR2 domain comprising the amino acid sequence of SEQ ID NO: 73, and a CDR1 domain comprising the amino acid sequence of SEQ ID NO: 50;
- the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6;
- the antibody, or antigen binding portion thereof, comprises a heavy chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54, and a light chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58;
- the antibody, or antigen binding portion thereof, comprises a heavy chain variable region comprising a CDR3 domain comprising the amino acid sequence of SEQ ID NO: 77, a CDR2 domain comprising the amino acid sequence of SEQ ID NO: 76, and a CDR1 domain comprising the amino acid sequence of SEQ ID NO: 75, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50; or
- the antibody, or antigen binding portion thereof, comprises a heavy chain variable region comprising a CDR3 domain comprising the amino acid sequence of SEQ ID NO: 106, a CDR2 domain comprising the amino acid sequence of SEQ ID NO: 105, and a CDR1 domain comprising the amino acid sequence of SEQ ID NO: 62, and a light chain variable region comprising a CDR3 domain comprising the amino acid sequence of SEQ ID NO: 60, a CDR2 domain comprising the amino acid sequence of SEQ ID NO: 73, and a CDR1 domain comprising the amino acid sequence of SEQ ID NO: 50.

3. An isolated nucleic acid encoding the antibody, or antigen binding portion thereof, of claim 1 or claim 2.

4. A pharmaceutical composition comprising the antibody, or antigen binding portion thereof, of claim 1 or claim 2, and a pharmaceutically acceptable carrier.

5. An antibody, or antigen binding portion thereof, of claim 1 or claim 2, conjugated to at least one drug.

6. The antibody, or antigen binding portion thereof, of claim 5, wherein the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor.

7. The antibody, or antigen binding portion thereof, of claim 5, wherein the at least one drug is conjugated to the antibody, or antigen-binding portion thereof, via a linker.

8. The antibody, or antigen binding portion thereof, of claim 5, wherein the antibody, or antigen binding portion thereof, is an IgG1 or IgG4 isotype.

9. A method for treating cancer, comprising administering a therapeutically effective amount of the antibody, or antigen binding portion thereof, of claim 1 or claim 2 to a subject in need thereof.

10. The method of claim 9, wherein the cancer is triple negative breast cancer (TNBC), acute myeloid leukemia, prostate cancer, breast cancer, lung cancer, colon cancer, colorectal cancer, melanomas, bladder cancer, brain/CNS cancer, cervical cancer, esophageal cancer, gastric cancer, head and neck cancer, kidney cancer, liver cancer, lymphomas, ovarian cancer, pancreatic cancer, or sarcomas.

11. The method of claim 9, wherein the antibody, or antigen binding portion thereof, is administered in combination with an immune checkpoint inhibitor.

12. A method for inhibiting or decreasing solid tumor growth in a subject having a solid tumor, said method comprising administering an effective amount of the antibody or antigen binding portion thereof of claim 1 or claim 2, to the subject having the solid tumor, such that the solid tumor growth is inhibited or decreased.

13. The method of claim 12, wherein the antibody or antigen binding portion thereof is administered in combination with an additional agent or an additional therapy.

14. The method of claim 13, wherein the additional agent is an immune checkpoint inhibitor.

15. A method for upregulating an immune response in a subject, comprising administering a therapeutically effective amount of the antibody or antigen binding portion thereof of claim 1 or claim 2 to the subject, thereby upregulating the immune response in the subject.

16. The method of claim 15, wherein the antibody, or antigen binding portion thereof, is administered in combination with an additional agent or an additional therapy.

17. The method of claim 16, wherein the additional agent is an immune checkpoint inhibitor.

18. The method of claim 15, wherein the subject has cancer.

19. A method for increasing T cell activation in a subject, comprising administering a therapeutically effective amount of the antibody, or antigen binding portion thereof, of claim 1 or claim 2 to the subject, thereby increasing T cell activation in the subject.

20. The method of claim 19, wherein the antibody, or antigen binding portion thereof, is administered in combination with an additional agent or an additional therapy.

21. The method of claim 20, wherein the additional agent is an immune checkpoint inhibitor.

22. The method of claim 19, wherein the subject has cancer.

* * * * *